United States Patent
Yu et al.

(10) Patent No.: US 10,246,481 B2
(45) Date of Patent: Apr. 2, 2019

(54) BILE ACID DERIVATIVES AND METHODS FOR SYNTHESIS AND USE

(71) Applicant: City of Hope, Duarte, CA (US)

(72) Inventors: Donna Yu, Arcadia, CA (US); Barry Forman, Irvine, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 15/983,859

(22) Filed: May 18, 2018

(65) Prior Publication Data

US 2018/0319836 A1 Nov. 8, 2018

Related U.S. Application Data

(62) Division of application No. 15/436,589, filed on Feb. 17, 2017, now abandoned.

(60) Provisional application No. 62/296,400, filed on Feb. 17, 2016.

(51) Int. Cl.
C07J 9/00 (2006.01)

(52) U.S. Cl.
CPC .................................... C07J 9/005 (2013.01)

(58) Field of Classification Search
CPC ....................................................... C07J 9/005
See application file for complete search history.

(56) References Cited

U.S. PATENT DOCUMENTS

| 2008/0182832 A1* | 7/2008 | Pellicciari | C07J 9/00 514/182 |
|---|---|---|---|
| 2017/0233431 A1 | 8/2017 | Hui et al. | |

FOREIGN PATENT DOCUMENTS

| EP | 1568706 | 8/2005 |
|---|---|---|
| ES | 489661 | 4/1981 |
| ES | 499525 | 2/1982 |

OTHER PUBLICATIONS

Akwabi-Ameyaw, A. et al. (Aug. 1, 2008, e-published Jun. 28, 2008). "Conformationally constrained farnesoid X receptor (FXR) agonists: Naphthoic acid-based analogs of GW 4064," *Bioorg Med Chem Lett* 18(15):4339-4343.

Andrali, S.S. e al. (Nov. 11, 2005). "Ataxin-10 interacts with O-GlcNAc transferase OGT in pancreatic beta cells," *Biochem Biophys Res Commun* 337(1):149-153.

Bhattacharyya, P. K. et al. (1978). "Determination of chenodeoxycholic acid and ursodeoxycholic acid by nuclear magnetic resonance spectrometry," *Analytical Chem.*, 50:1462-1465.

Bissell, D.M et al. (1980). "Phenotypic stability of adult rat hepatocytes in primary monolayer culture," *Ann N Y Acad Sci.* 349:85-98.

Campana, G. et al. (Jun. 15, 2005). "Regulation of ileal bile acid-binding protein expression in Caco-2 cells by ursodeoxycholic acid: role of the farnesoid X receptor," *Biochem Pharmacol* 69(12):1755-1763.

D'Amore, C. et al. (Feb. 13, 2014, e-published Jan. 17, 2014). "Design, synthesis, and biological evaluation of potent dual agonists of nuclear and membrane bile acid receptors," *J Med Chem* 57(3):937-954.

(Continued)

*Primary Examiner* — San Ming R Hui
(74) *Attorney, Agent, or Firm* — Mintz Levin Cohn Ferris Glovsky and Popeo, P.C.

(57) ABSTRACT

Provided herein, inter alia, are methods for the preparation of modulators of farnesoid X receptor (FXR), and compositions and uses of the modulators of FXR.

24 Claims, 9 Drawing Sheets

Specification includes a Sequence Listing.

(56) References Cited

OTHER PUBLICATIONS

Fieser, L.F. et al. (1950). "Oxidation of steroid. III. Selective oxidation and acylations in bile acid series," *J Am Chem Soc* 72:5530-5536.

Forman, B.M. et al. (Jun. 2, 1995). "Identification of a nuclear receptor that is activated by farnesol metabolites," *Cell* 81(5):687-693.

Heathcote, E.J. (Apr. 2000). "Management of primary biliary cirrhosis. The American Association for the Study of Liver Diseases practice guidelines," *Hepatology* 31(4):1005-1013.

Hofmann, A.F. (1994). "Pharmacology of ursodeoxycholic acid, an enterohepatic drug," *Scand J Gastroenterol* 29:1-15.

Hsai, S.L. et al. (Apr. 1957). "Bile acids. V. Chemical studies on new bile acids from the rat and the hog," *J Biol Chem* 225(2):811-823.

Iida, T. et al. (1982). "Potential Bile Acid metabolites. 6. Stereoisomeric 3,7-Dihydroxy-5β-Cholanic Acids," *J.Org. Chem.* 47:2966-2972.

Kanazawa, T. et al. (1954). Syntheses of Ursodesoxycholic Acid and Its Conjugated Bile Acid, *Proc Japan Acad* 30:391-392.

Li, T. et al. (Sep. 29, 2006, e-published Aug. 2, 2006). "Insulin regulation of cholesterol 7alpha-hydroxylase expression in human hepatocytes: roles of forkhead box O1 and sterol regulatory element-binding protein 1c," *J Biol Chem* 281(39):28745-28754.

Liu, Z. et al. "Advance in methods for preparation of ursodeoxycholic acid," Yaoxue Tongbao. 1988, 23, 583-86, Chem Abstr. 1989, 110, 115167s.

Maloney, P.R. et al. (Aug. 10, 2000). "Identification of a chemical tool for the orphan nuclear receptor FXR," *J Med Chem* 43(16):2971-2974.

Meerwein, H. et al. (1925). "A new method for reducing aldehydes and ketones," *Justus Liebigs Ann. Chem.* 444:221. (with English Translation).

Miyashita, N. et al. (1977). "Pyridinium p-toluenesulfonate. A mild and efficient catalyst for the tetrahydropyranylation of alcohols," *J. Org. Chem.* 42:3772-3774.

Moschetta, A. et al. (Dec. 2004, e-published Nov. 21, 2004). "Prevention of cholesterol gallstone disease by FXR agonists in a mouse model," *Nat Med* 10(12):1352-1358.

Nam, S. et al. (Jun. 2013). "Dual inhibition of Janus and Src family kinases by novel indirubin derivative blocks constitutively-activated Stat3 signaling associated with apoptosis of human pancreatic cancer cells," *Mol Oncol* 7(3):369-378.

Pellicciari, R. et al. (Aug. 15, 2002). "6alpha-ethyl-chenodeoxycholic acid (6-ECDCA), a potent and selective FXR agonist endowed with anticholestatic activity," *J Med Chem* 45(17):3569-3572.

Piatkowski, W. et al. (1999). "The oxidation technology of hydroxycholanic acids to the corresponding oxo- derivatives," Polish Journal of Applied Chemistry 43, 85-93.

Ponndorf, W. (1926). "The reversible exchange of oxygen between aldehydes or ketones on the one hand and primary or secondary alcohols on the other hand," *Angew Chem* 39:138. (with English Translation).

Salen, G. et al. (Jun. 1980). "Effect of high and low doses of ursodeoxycholic acid on gallstone dissolution in humans," *Gastroenterology* 78(6):1412-1418.

Samuelson, B. (1960). "Preparation of ursodeoxycholic acid and 3α,7β,12α-trihydroxycholanic acid," *Acta Chem Scand* 14:17-20.

Shaffer, E.A. (May 2005). "Epidemiology and risk factors for gallstone disease: has the paradigm changed in the 21st century?" *Curr Gastroenterol Rep* 7(2):132-140.

Sharma, R. et al. (Jan. 13, 2011, e-published Dec. 15, 2010). "Ursodeoxycholic acid amides as novel glucocorticoid receptor modulators," *J Med Chem* 54(1):122-130.

Verley, M. (1925). *Bull. Soc. Chim. Fr.* 37:871-874. (with English Translation).

Wang, H. et al. (May 1999). "Endogenous bile acids are ligands for the nuclear receptor FXR/BAR," *Mol Cell* 3(5):543-553.

Wang, H.H. et al. (Apr. 2013, e-published Feb. 19, 2013). "Prevention of cholesterol gallstones by inhibiting hepatic biosynthesis and intestinal absorption of cholesterol," *Eur J Clin Invest* 43(4):413-426.

Watanabe, M. et al. (Jan. 26, 2006, e-published Jan. 8, 2006). "Bile acids induce energy expenditure by promoting intracellular thyroid hormone activation," Nature 439(7075:484-489.

Wittenburg, H. et al. (Sep. 2003). "FXR and ABCG5/ABCG8 as determinants of cholesterol gallstone formation from quantitative trait locus mapping in mice," *Gastroenterology* 125(3):868-881.

Xu, J.Y. et al. (Oct. 2014). "Recent insights into farnesoid X receptor in non-alcoholic fatty liver disease," *World J Gastroenterol* 20(37):13493-13500.

Yu, D. et al. (Nov. 2012, e-published Sep. 21, 2012). "An improved synthesis of 6α-ethylchenodeoxycholic acid (6ECDCA), a potent and selective agonist for the Farnesoid X Receptor (FXR)," *Steroids* 77(13):1335-1338.

Yu, D.D. et al. (Jul. 15, 2013, e-published May 7, 2013). "Development of time resolved fluorescence resonance energy transfer-based assay for FXR antagonist discovery," *Bioorg Med Chem* 21(14):4266-4278.

Yu, D.D. et al. (Apr. 1, 2015, e-published Feb. 11, 2015). "Stereoselective synthesis, biological evaluation, and modeling of novel bile acid-derived G-protein coupled bile acid receptor 1 (GP-BAR1, TGR5) agonists," *Bioorg Med Chem* 23(7):1613-1628.

\* cited by examiner

BILE ACID DERIVATIVES AND METHODS FOR SYNTHESIS AND USE

CROSS-REFERENCES TO RELATED APPLICATIONS

This application is a divisional of U.S. non-provisional application Ser. No. 15/436,589, filed Feb. 17, 2017, which claims the benefit of U.S. Provisional Application No. 62/296,400, filed Feb. 17, 2016, which are incorporated herein by reference in their entireties and for all purposes.

REFERENCE TO A "SEQUENCE LISTING," A TABLE, OR A COMPUTER PROGRAM LISTING APPENDIX SUBMITTED ON A COMPACT DISK

The contents of the text file named "048440-591D01US Sequence Listing_ST25.txt," which was created on May 14, 2018, and is 1.30 KB in size, are hereby incorporated by reference in their entirety.

BACKGROUND OF THE INVENTION

Cholesterol gallstone disease (CGD) is one of the most prevalent digestive diseases, leading to considerable financial and social burden worldwide. Ursodeoxycholic acid (UDCA) is the only bile acid drug approved by FDA for the non-surgical treatment of gallstones. However, a molecular link between UDCA and CGD is unclear. Data suggest that farnesoid X receptor (FXR), a bile acid nuclear receptor, could protect against the development of CGD. Thus, the identification of selective and potent modulators for FXR with enhanced efficacy is of crucial and significant value. Provided herein are solutions to these and other problems in the art.

BRIEF SUMMARY OF THE INVENTION

Disclosed herein, inter alia, are bile acid derivatives and methods of making bile acid derivatives. Also disclosed are compositions that include a bile acid derivative. Further disclosed herein are methods of treating diseases or conditions using the bile acid derivatives.

In a first aspect is provided a method of synthesizing a compound having the following structure,

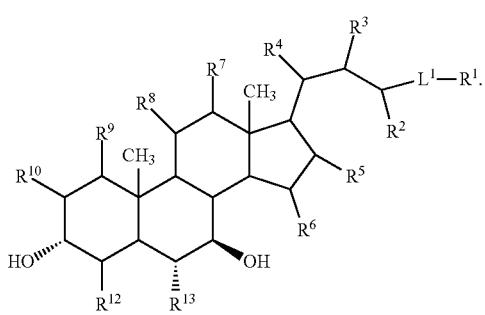

(I)

$L^1$ is —C(O)—, —C(O)O—, —C(O)NH—, or —CH$_2$—.
$R^1$ is hydrogen, halogen, —N$_3$, —CF$_3$, —CCl$_3$, —CBr$_3$, —CI$_3$, —CN, —CHO, —OR$^{1A}$, —NHR$^{1A}$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a carboxylate protecting group.

$R^2$ is independently hydrogen or unsubstituted alkyl.
$R^3$ is independently hydrogen, unsubstituted alkyl, or —OR$^{3A}$.
$R^4$ is independently hydrogen, unsubstituted alkyl, or —OR$^{4A}$.
$R^5$ is independently hydrogen, unsubstituted alkyl, or —OR$^{5A}$.
$R^6$ is independently hydrogen, unsubstituted alkyl, or —OR$^{6A}$.
$R^7$ is independently hydrogen, unsubstituted alkyl, or —OR$^{7A}$.
$R^8$ is independently hydrogen, unsubstituted alkyl, or —OR$^{8A}$.
$R^9$ is independently hydrogen, unsubstituted alkyl, or —OR$^{9A}$.
$R^{10}$ is independently hydrogen, unsubstituted alkyl, or —OR$^{10A}$.
$R^{12}$ is independently hydrogen, unsubstituted alkyl, or —OR$^{12A}$.
$R^{13}$ is independently unsubstituted alkyl.
$R^{1A}$, $R^{3A}$, $R^{4A}$, $R^{5A}$, $R^{6A}$, $R^{7A}$, $R^{8A}$, $R^{9A}$, $R^{10A}$, $R^{12A}$ and $R^{13A}$ are independently hydrogen, unsubstituted alkyl, or an alcohol protecting group.

In another aspect is a compound according to Formula (I), or a pharmaceutically acceptable salt thereof.

In another aspect is an insulin peptide hormone covalently bonded to a compound according to Formula (I), or a pharmaceutically acceptable salt thereof.

In another aspect is a compound according to Formula (I-1), comprising an insulin peptide hormone, or a pharmaceutically acceptable salt thereof.

In another aspect is a pharmaceutical composition comprising a compound, or a pharmaceutically acceptable salt thereof, as provided herein, including embodiments thereof, and a pharmaceutically acceptable excipient.

In another aspect is a method of treating or preventing diabetes (e.g., Type 1 or Type 2 diabetes), obesity, insulin resistance, or liver disease in a subject in need thereof. The method includes administering to said subject a therapeutically effective amount of a compound as provided herein, including embodiments thereof. In embodiments, the method relates to treating or preventing Type 1 or Type 2 diabetes.

In another aspect is a method of treating or preventing a disorder or condition mediated by farnesoid X receptor (FXR) activity in a subject in need thereof. The method includes administering to said subject a therapeutically effective amount of a compound as provided herein, including embodiments thereof. In embodiments, the disorder or condition is cholestasis, diabetes, liver disease, or cholesterol gallstone disease (CGD).

In another aspect is a method of treating or preventing cancer. The method includes administering to said subject in need thereof, a therapeutically effective amount of a compound as provided herein, including embodiments thereof.

BRIEF DESCRIPTION OF THE DRAWINGS

FIG. 8A shows All-Around Docking poses of UDCA and GW4064 molecule on FXR. FIG. 8B shows the binding pocket of FXR bound by 6EUDCA. FIG. 8C shows two hydrogen bonds are formed between UDCA and residues H447 and M365 on FXR. FIG. 8D shows eight hydrogen bonds are formed between 6EUDCA and residues S332, R331, V325, F329, M328, H447 and M290.

DETAILED DESCRIPTION OF THE INVENTION

I. Definitions

Figure 1:
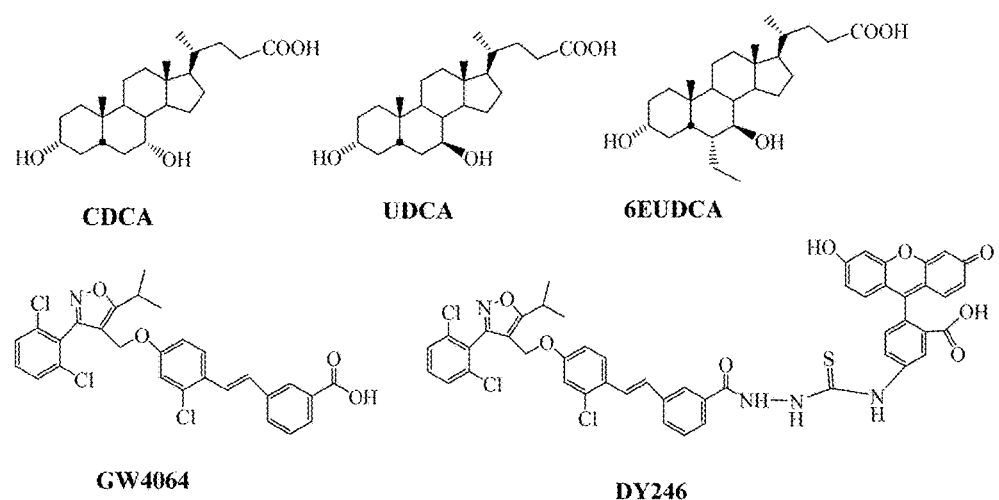
FIG. 1 shows the chemical structures of CDCA, UDCA, 6EUDCA, GW4064, and DY246.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH2O— is equivalent to —OCH2-.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). An alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present invention. An alkylene is au uncyclized chain. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g. selected from the group consisting of O, N, P, Si, and S), and wherein the nitrogen and sulfur atoms may optionally be oxidized, and the nitrogen heteroatom may optionally be quaternized. A heteroalkyl is an uncyclized chain. The heteroatom(s) O, N, P, S, B, As, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to eight optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. A heteroalkylene is an uncyclized chain. As described above, heteroalkyl groups, as used herein, include those groups that are attached to the remainder of the molecule through a heteroatom, such as —C(O)R', —C(O) NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. A cycloalkyl or heteroalkyl is not aromatic. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isox-azolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be a —O— bonded to a ring heteroatom nitrogen.

A "fused ring aryl-heterocycloalkyl" is an aryl fused to a heterocycloalkyl. A "fused ring heteroaryl-heterocycloalkyl" is a heteroaryl fused to a heterocycloalkyl. A "fused ring heterocycloalkyl-cycloalkyl" is a heterocycloalkyl fused to a cycloalkyl. A "fused ring heterocycloalkyl-heterocycloalkyl" is a heterocycloalkyl fused to another heterocycloalkyl. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be unsubstituted or substituted with one or more of the substitutents described herein. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be named according to the size of each of the fused rings. Thus, for example, 6,5 aryl-heterocycloalkyl fused ring describes a 6 membered aryl moiety fused to a 5 membered heterocycloalkyl. Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substitutents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)N R'R", —NR"C(O)R', —NR'—C(O)NR"R'", —NR"C(O)₂R', —NR—C(NR'R"R''')═NR"", —NR—C(NR'R")═NR'", —S(O)R', —S(O)₂R', —S(O)₂NR'R", —NR'NR"R'", —NRSO₂R', —ONR'R", —NR'C═(O)NR"NR'"R"", —CN, —NO₂, —NR'SO₂R", —NR'C═(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF₃ and —CH₂CF₃) and acyl (e.g., —C(O)CH₃, —C(O)CF₃, —C(O)CH₂OCH₃, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO₂R', —CONR'R", —OC (O)NR'R", —NR"C(O)R', —NR'—C(O)NR"R'", —NR"C(O)₂R', —NR—C(NR'R"R''')═NR"", —NR—C(NR'R")═NR'", —S(O)R', —S(O)₂R', —S(O)₂NR'R", —NRSO₂R', —NR'NR"R'", —ONR'R", —NR'C═(O)NR"NR'"R"", —CN, —NO₂, —R', —N₃, —CH(Ph)₂, fluoro(C₁-C₄)alkoxy, and fluoro(C₁-C₄)alkyl, —NR'SO₂R", —NR'C═(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one or more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH₂)$_r$—B—, wherein A and B are independently —CRR'—, —O—, —NR—, —S—, —S(O)—, —S(O)₂—, —S(O)₂NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —NR'—, —S—, —S(O)—, —S(O)₂—, or —S(O)₂NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), Boron (B), Arsenic (As), and silicon (Si).

A "substituent group," as used herein, means a group selected from the following moieties:

(A) oxo, halogen, —CF₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC═(O)NHNH₂, —NHC═(O) NH₂, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:
  (i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, and heteroaryl, substituted with at least one substituent selected from:
    (a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, or heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, and unsubstituted heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, and/or each substituted or unsubstituted heterocycloalkyl is a substituted or unsubstituted 3 to 8 membered heterocycloalkyl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, and/or each substituted or unsubstituted heterocycloalkylene is a substituted or unsubstituted 3 to 8 membered heterocycloalkylene.

In some embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, and/or each substituted or unsubstituted heterocycloalkyl is a substituted or unsubstituted 3 to 7 membered heterocycloalkyl. In some embodiments, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted C$_3$-C$_7$ cycloalkylene, and/or each substituted or unsubstituted heterocycloalkylene is a substituted or unsubstituted 3 to 7 membered heterocycloalkylene.

Certain compounds of the present invention possess asymmetric carbon atoms (optical or chiral centers) or double bonds; the enantiomers, racemates, diastereomers (e.g., epimers), tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "epimer," as used herein, refers to one of two stereoisomers, each of which has two or more stereogenic carbon centers and where the two stereoisomers differ in configuration at one and only one stereogenic carbon center.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

The term "silyl ether" as used herein, refers to a chemical compound containing a silicon atom covalently bonded to an alkoxy group generally having the structure R$^w$R$^x$R$^y$Si—O—R$^z$, wherein R$^w$, R$^x$, R$^y$, and R$^z$ are independently alkyl or aryl groups.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of salts include mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. The term salt also refers to formation of a salt between two compounds.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present invention, whether radioactive or not, are encompassed within the scope of the present invention.

The symbol "⌇" denotes the point of attachment of a chemical moiety to the remainder of a molecule or chemical formula.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Description of compounds of the present invention is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule viaring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, include prevention of an injury, pathology, condition, or disease.

A "therapeutically effective amount" or "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). A therapeutically effective amount is an amount sufficient to contribute to the treatment, prevention, or reduction of a symptom or symptoms of a disease. A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Patient" or "subject in need thereof" refers to a living organism suffering from or prone to a condition that can be treated by administration of a pharmaceutical composition as provided herein. Non-limiting examples include humans, other mammals (e.g. mice, rats, dogs, monkeys, cows, goats, sheep) and other non-mammalian animals. In some embodiments, a patient or subject in need thereof is a human with a disease or condition.

The term "diabetes" as used herein refers to onset and inducement of diabetes mellitus in any manner and includes type 1, type 2, gestational, steroid-induced, HIV treatment induced and autoimmune diabetes. Diabetes is recognized as a complex, chronic disease in which 60% to 70% of all case fatalities among diabetic patients are a result of cardiovascular complications. Diabetes is not only considered a coronary heart disease risk equivalent but is also identified as an independent predictor of adverse events, including recurrent myocardial infarction, congestive heart failure, and death following a cardiovascular incident. The adoption of tighter glucose control and aggressive treatment for cardiovascular risk factors would be expected to reduce the risk of coronary heart disease complications and improve overall survival among diabetic patients. Yet, diabetic patients are two to three times more likely to experience an acute myocardial infarction than non-diabetic patients, and diabetic patients live eight to thirteen years less than non-diabetic patients.

As used herein, the term "liver disease" refers to any symptoms related to liver dysfunction including physical signs and symptoms related to digestive problems, blood sugar disorders, immune disorders, and abnormal fat absorption and metabolism. Liver disease as used herein refers to all types of liver dysfunction including hepatitis, alcoholic liver disease, fatty liver disease, non-alcoholic fatty liver disease, inflammatory liver disease, cirrhosis, hereditary diseases, and cancers associated with the liver.

As used herein, the term "cancer" refers to all types of cancer, neoplasm, benign or malignant tumors found in mammals, including. Exemplary cancers include liver, colon, kidney, and stomach cancers. Additional examples include lung, non-small cell lung, brain, breast, pancreas, prostate, ovary, sarcoma, melanoma, cervix, head & neck, and uterus cancers, as well as leukemia, carcinomas and sarcomas, mesothelioma, metastatic bone cancer, Medulloblastoma, Hodgkin's Disease, Non-Hodgkin's Lymphoma, multiple myeloma, neuroblastoma, rhabdomyosarcoma, primary thrombocytosis, primary macroglobulinemia, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, and neoplasms of the endocrine and exocrine pancreas. In embodiments, the cancer may be liver cancer.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "linker" as described herein is a divalent chemical group that covalently joins one chemical moiety to another. Specific examples of linkers are described herein. Linkers may be polyethylene (PEG) linkers or bioconjugate linkers.

As used herein, the term "bioconjugate" or "bioconjugate linker" refers to the resulting association between atoms or molecules of bioconjugate reactive groups. The association can be direct or indirect. For example, a conjugate between a first bioconjugate reactive group (e.g., —NH$_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g. a first linker of second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, bioconjugates or bioconjugate linkers are formed using bioconjugate chemistry (i.e. the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g. a sulfhydryl). In embodiments, the first bioconjugate reactive group (e.g., haloacetyl moiety) is covalently attached to the second bioconjugate reactive group (e.g. a sulfhydryl). In embodiments, the first bioconjugate reactive group (e.g., pyridyl moiety) is covalently attached to the second bioconjugate reactive group (e.g. a sulfhydryl). In embodiments, the first bioconjugate reactive group (e.g., —N-hydroxysuccinimide moiety) is covalently attached to the second bioconjugate reactive group (e.g. an amine). In embodiments, the first bioconjugate reactive group (e.g., maleimide moiety) is covalently attached to the second bioconjugate reactive group (e.g. a sulfhydryl). In embodiments, the first bioconjugate reactive group (e.g., -sulfo-N-hydroxysuccinimide moiety) is covalently attached to the second bioconjugate reactive group (e.g. an amine).

Useful bioconjugate reactive groups used for bioconjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido or maleimide groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold, or react with maleimides;

(h) amine or sulfhydryl groups (e.g., present in cysteine), which can be, for example, acylated, alkylated or oxidized;

(i) alkenes, which can undergo, for example, cycloadditions, acylation, Michael addition, etc;

(j) epoxides, which can react with, for example, amines and hydroxyl compounds;

(k) phosphoramidites and other standard functional groups useful in nucleic acid synthesis;

(l) metal silicon oxide bonding; and (m) metal bonding to reactive phosphorus groups (e.g. phosphines) to form, for example, phosphate diester bonds.

(n) azides coupled to alkynes using copper catalyzed cycloaddition click chemistry.

(o) biotin conjugate can react with avidin or strepavidin to form a avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

As described herein, an insulin peptide hormone may be covalently bonded to a compound of Formula (I), Formula (I-C), Formula (I-D), Formula (I-E), or Formula (I-F). As a non-limiting example, an insulin peptide hormone covalently bonded to a compound of Formula (I) may have the Formulae:

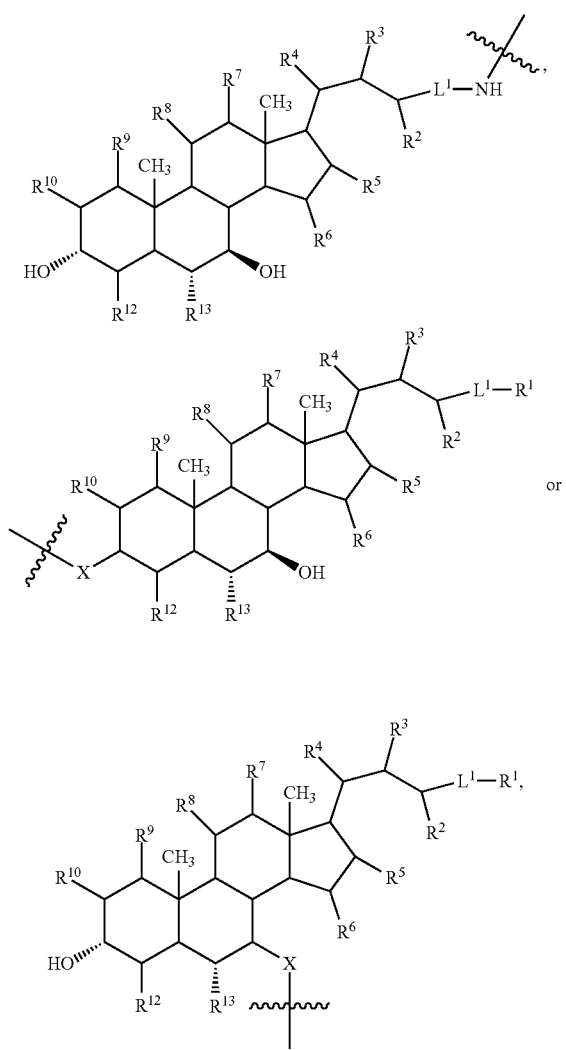

wherein —NH— and X are the nitrogen of an amino acid residue of an insulin peptide hormone or X is the hydroxyl of a compound of Formula (I), which is bonded to the remainder of the insulin peptide hormone and $L^1$, $R^2$, $R^3$, $R^4$, $R^5$, $R^6$, $R^7$, $R^8$, $R^9$, $R^{10}$, $R^{12}$ and $R^{13}$ are as described herein. An insulin peptide hormone may be covalently bonded to a compound of Formula (I), Formula (I-C), Formula (I-D), Formula (I-E), or Formula (I-F) through the reacted residue of an electrophilic group (e.g., carboxyl group) of the insulin peptide hormone. An insulin peptide hormone may be covalently bonded to a compound of Formula (I), Formula (I-C), Formula (I-D), Formula (I-E), or Formula (I-F) through the reacted residue of a nucleophilic group (e.g., lysine (including but not limited to B29 lysine of an insulin peptide) or terminal amino group) of the insulin peptide hormone.

The term "electrophilic group" is used in accordance with its plain ordinary meaning and refers to a chemical group, e.g., a moiety, ion or atom that is electron deficient and is attracted to electrons. Electron deficiency can include a formal positive charge or a partial positive charge. By way of example, carbon bonded to one or more electronegative atoms (or groups), such as oxygen, nitrogen, sulfur or a halogen, can become electron deficient and in combination with the electronegative atoms to which it is bonded forms an electrophilic group. Electrophilic groups include but are not limited to alkyl halides, acyl halides, alkyl sulfonates, aldehydes or ketones.

The term "nucleophilic group" is used in accordance with its plain ordinary meaning and refers to a chemical group, e.g., a moiety, ion or atom that is electron rich or electron dense and is attracted to electron poor or electron deficient (i.e., electrophilic) groups. Electron density can include a formal negative charge or a partial negative charge. Nucleophilic groups include but are not limited to amines, alcohols, isothiocyanates and/or thiols.

Figure 9:
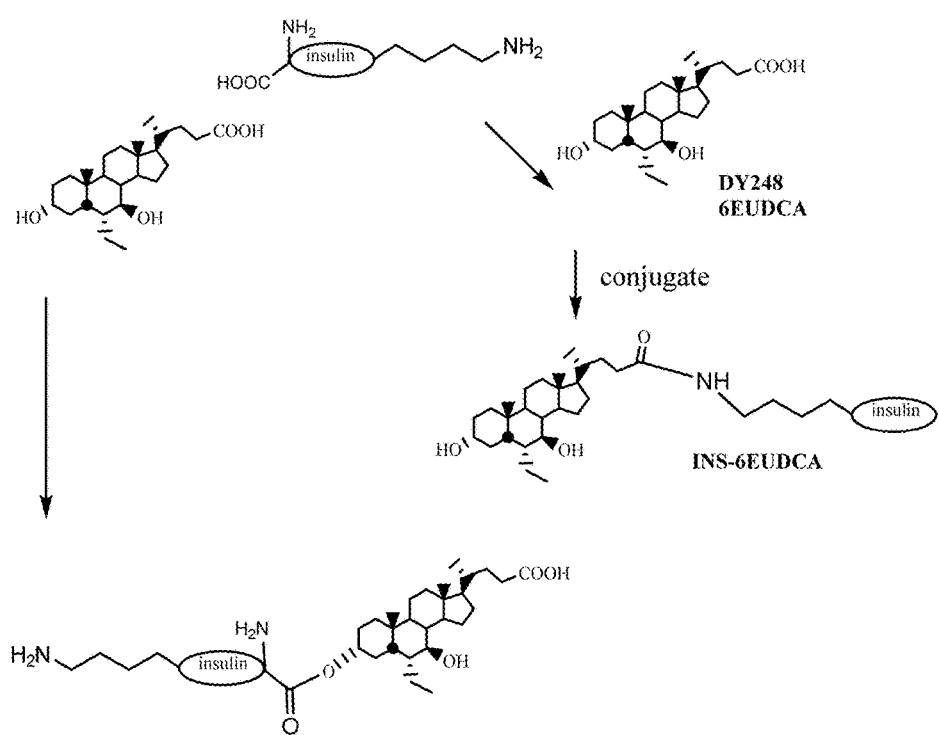
FIG. 9 is a schematic diagram illustrating exemplary conjugation of 6EUDCA to insulin.

In another non-limiting example, carboxylic acid-containing 6EUDCA may be conjugated to the native human insulin protein through the e-amine of the lysine at the B29 position of insulin. Alternatively, hydroxyl-containing 6EUDCA may be conjugated to the native human insulin protein through the carboxylic acid terminus of insulin (FIG. 9).

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

The term "modulator" refers to a composition that increases or decreases the level of a target molecule or the function of a target molecule or the physical state of the target of the molecule.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

The term "sterically hindered base" refers to a chemical base that reacts with a carbon atom within a separate molecule in a preferred stereochemical orientation due to spatial constraints caused by its attached chemical moieties, which are typically bulky chemically moieties. Sterically hindered bases useful in the present methods include: tBuO; PhO; MeO; EtO; bis(trimethylsilyl)amide (HMDS); 2,2,6,6-tetramethylpiperidine (TMP); 1,8-Diazabicyclo[5.4.0]undec-7-ene (DBU); 1,4-Diazabicyclo[2.2.2]octane (Dabco); 1,5-Diazabicyclo[4.3.0]non-5-ene (DBN); N,N-dichlorohexylmethylamine; N,N-diisopropyl-2-ethylbutylamine; 2,6-di-tert-butyl-4-methylpyridine; 7-Methyl-1,5,7-triazabicyclo(4.4.0)dec-5-ene (MTBD); 3,3,6,9,9-Pentamethyl-2,10-diazabicyclo-(4.4.0)dec-1-ene (PMDBD); 1,2,2,6,6-Pentamethylpiperidine (PMP); 1,5,7-Triazabicyclo(4.4.0)dec-5-ene (TBD); or tri-tert-butylpyridine. Bases may be complexed with $M^{+1}$ charged metals such as K, Na, or Li.

As used herein, the term "carboxylate protecting group" is a monovalent chemical moiety covalently bound to a monovalent carboxylate moiety oxygen atom that functions to prevent the carboxylate moiety from reacting with reagents used in the chemical synthetic methods described herein (commonly referred to as "protecting" the carboxylate group) and may be removed under conditions that do not degrade the molecule of which the carboxylate moiety forms a part (commonly referred to as "deprotecting" the carboxylate group) thereby yielding a free carboxylic acid. A carboxylate protecting group can be acid labile, base labile, or can be labile in the presence of other reagents. Carboyxlate protecting groups include but are not limited to: methyl ester; t-butyl ester; 2,2,2-trichloroethyl ester; 4-nitrobenzyl ester; cyanoethyl ester; 4-methyl-2,6,7-trioxabicyclo[2.2.2]octane; iminoethers; or lactones.

As used herein, the term "carboxylate deprotecting agent" is a chemical compound or element that functions to remove a carboxylate protecting group, thereby yielding a free carboxylic acid. Carboxylate deprotecting agents useful in the present methods include: LiOH, diethyl amine, triethyl amine, piperidine, tetrabutylammonium hydroxide, fluoride ion, hydrogenation, or sodium.

As used herein, the term "alcohol protecting group" is a monovalent chemical moiety covalently bound to a monovalent alcohol oxygen atom that functions to prevent the alcohol moiety from reacting with reagents used in the chemical synthetic methods described herein (commonly referred to as "protecting" the alcohol group) and may be removed under conditions that do not degrade the molecule of which the alcohol moiety forms a part (commonly referred to as "deprotecting" the alcohol group) thereby yielding a free hydroxyl. An alcohol protecting group can be acid labile, base labile, or labile in the presence of other reagents. Alcohol protecting groups include but are not limited to: benzyl (Bn); p-methoxybenzyl (PMB); dimethoxybenzyl (DMB), allyl; allyl carbonate, -trityl (Trt); -p-methoxyphenyl (PMP); tetrahydropyranyl (THP); methoxymethyl (MOM); 1-ethoxyethyl (EE); 2-methoxy-2-propyl (MOP); 2,2,2-trichloroethoxymethyl; 2-methoxyethoxymethyl (MEM); 2-trimethylsilylethoxymethyl (SEM); methylthiomethyl (MTM), -trimethylsilyl (TMS); -triethylsilyl (TES); triisopropylsilyl (TIPS); triphenylsilyl (TPS); triphenylmethyl (Tr), t-butyldimethylsilyl (TBDMS); t-butyldiphenylsilyl (TBDPS); acetyl (Ac); benzyloxy (Bz); 2,2,2-trichloroethyl carbonate (Troc); or 2-trimethylsilylthehyl carbonate.

As used herein, the term "alcohol deprotecting agent" is a chemical compound or element that functions to remove an alcohol protecting group, thereby yielding a free hydroxyl. Alcohol deprotecting agents useful in the present methods include: zinc bromide, magnesium bromide, titanium tetrachloride, dimethylboron bromide, trimethylsilyl iodide, silver (Ag+) salts, mercury (Hg+) salts, zinc, samarium diiodide, sodium amalgam, trifluoroacetic acid, hydrofluoric acid, hydrochloric acid, hydrogenation, (TBAF) tetra-n-butylammonium fluoride, boron trifluoride, or silicon tetrafluoride.

The term "reducing agent" is a chemical compound or element that donates electrons to another chemical compound in an oxidation-reduction reaction. Reducing agents are typically used to add a hydrogen to a molecule.

The term "oxidizing agent" is a chemical compound or element that accepts or gains electrons from another chemical compound in an oxidation-reduction reaction.

The term "polar aprotic solvent" refers to a chemical compound used as a solvent having a dipole moment, and therefore polarity, but lacking an ability to hydrogen bond through —OH or —NH bonds with itself or other compounds. Such solvents include but are not limited to: hexamethylphosphoramide (HMPA), hexamethylphosphorous triamide (HMPT), N,N-dimethylformamide (DMF), dimethyl sulfoxide (DMSO), acetonitrile (MeCN), dioxane, acetone, tetrahydrofuran (THF), N-methylpyrrolidone (NMP), N,N'-dimethyl-N,N'-trimethyleneurea (DMPU), or tetra-alkyl ureas.

A "coupling reagent" as used herein is a chemical compound that forms an activated ester used in forming amide bonds, such as non-racemized amide bonds. Coupling reagents useful in the present methods include but are not limited to: EEDQ (N-ethoxy-2-ethoxy-1,2-dihydroquinoline); BOP (Benzotriazole-1-yl-oxy-tris-(dimethylamino)-phosphoniumhexaflurophospate); PyBOP (Benzotriazole-1-yl-oxy-tris-pyrrolidino-phosphonium hexafluorophosphate); DMAP(4-dimethylaminopyridine); HATU (2-(O-(7-azabenzotriazol-1-yl)-1,1,3,3-tetramethyluronium hexafluorophosphate); HBTU (2-(1H-benzotriazole-1-yl)-1,1,3,3-tetramethylaminium hexafluorophosphate); HCTU (2-(6-chloro-1H-benzotriazole-1-yl)-1,1,3,3-tetramethylaminium hexafluorophosphate; or HObt (N-hydroxybenzotriazole); TOTU (O-((ethoxycarbonyl)cyanomethylene amino)-N,N,N'N'-tetramethyluronium tetrafluoroborate); DCC (dicyclohexyl carbodiimide); DIC (diisopropyl carbodiimide); EDC (1-ethyl-3-(3'-dimehtylamino)carbodiimide); (DMTMM) 4-(4,6-dimethoxy-(1,3,5)triazine-2-yl)-4-methyl-morpholinium chloride; 1-Chloro-4,6-dimethoxy-1.3.5-triazine.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A polypeptide, or a cell is "recombinant" when it is artificial or engineered, or derived from or contains an artificial or engineered protein or nucleic acid (e.g. non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

The terms "insulin peptide hormone" and "insulin" refer to a protein (including homologs, isoforms, and functional fragments thereof) with insulin action. The term includes any recombinant or naturally-occurring form of insulin or variants thereof that maintain insulin action (e.g. within at least 30%, 40%, 50%, 60%, 70%, 80%, 90%, 95%, or 100% action compared to wildtype insulin). In embodiments, the insulin is human insulin. In embodiments, the insulin has the following 110-residue sequence: MALWMRLLPLLALLALWGPDP AAAFVNQHLCGSHLVEALYLVCGERGFFYTPKTRREAEDLQVGQVELGGGPGAGSLQP LALEGSLQKRGIVEQCCTSICSLYQLENYCN (SEQ ID NO: 1). See NCBI locus AAA59182.1. In embodiments, the insulin is recombinant insulin. As well known in the art, insulin undergoes post-translational processing prior to formation of the biological active species. The terms "biologically active compound" and the like refer in the customary sense to compounds, e.g., polypeptides and the like, which can elicit a biological response.

II. Methods and Compositions

In one aspect is provided a method of synthesizing a compound having the following structure,

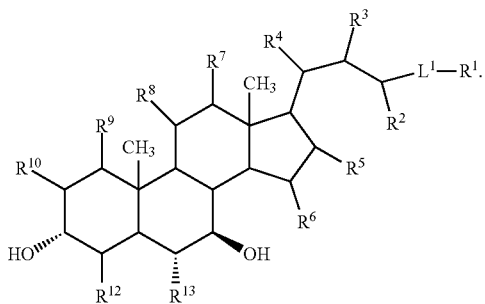

(I)

$L^1$ is —C(O)—, —C(O)O—, —C(O)NH—, or —CH$_2$—.
$R^1$ is hydrogen, halogen, —N$_3$, —CF$_3$, —CCl$_3$, —CBr$_3$, —CI$_3$, —CN, —CHO, —OR$^{1A}$, —NHR$^{1A}$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a carboxylate protecting group.

$R^2$ is independently hydrogen or unsubstituted alkyl.
$R^3$ is independently hydrogen, unsubstituted alkyl, or —OR$^{3A}$.
$R^4$ is independently hydrogen, unsubstituted alkyl, or —OR$^{4A}$.
$R^5$ is independently hydrogen, unsubstituted alkyl, or —OR$^{5A}$.
$R^6$ is independently hydrogen, unsubstituted alkyl, or —OR$^{6A}$.
$R^7$ is independently hydrogen, unsubstituted alkyl, or —OR$^{7A}$.
$R^8$ is independently hydrogen, unsubstituted alkyl, or —OR$^{8A}$.
$R^9$ is independently hydrogen, unsubstituted alkyl, or —OR$^{9A}$.
$R^{10}$ is independently hydrogen, unsubstituted alkyl, or —OR$^{10A}$.
$R^{12}$ is independently hydrogen, unsubstituted alkyl, or —OR$^{12A}$.
$R^{13}$ is independently unsubstituted alkyl.
$R^{1A}$, $R^{3A}$, $R^{4A}$, $R^{5A}$, $R^{6A}$, $R^{7A}$, $R^{8A}$, $R^{9A}$, $R^{10A}$, $R^{12A}$ and $R^{13A}$ are independently hydrogen, unsubstituted alkyl, or an alcohol protecting group.

In embodiments, the method comprises
(i) contacting a compound of formula (II)

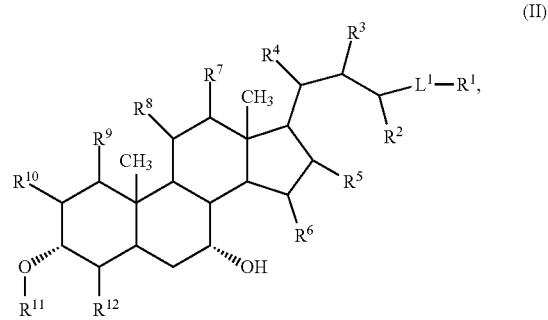

(II)

wherein $R^{11}$ is $R^{11A}$ or $R^{11B}$, with an oxidizing reagent to provide a compound of formula (III-A) or (III-B),

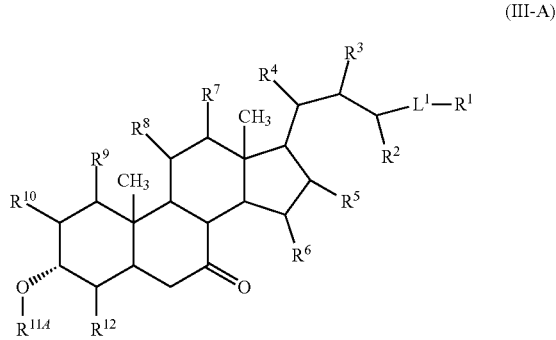

(III-A)

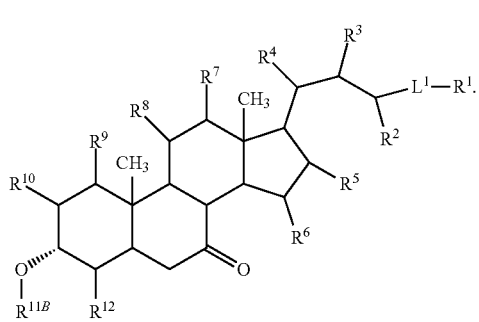

(III-B)

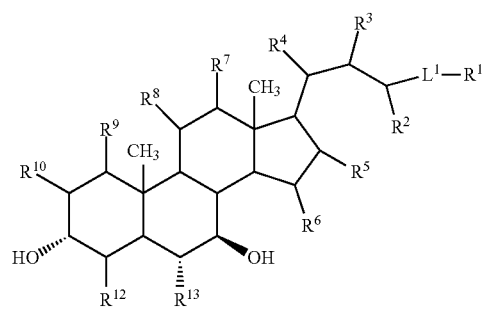

(I)

$R^{11A}$ is hydrogen.
$R^{11B}$ is an alcohol protecting group.

In embodiments, the method further comprises
(ii) when the product of step (i) has a structure according to formula (III-A), contacting the compound of formula (III-A) with an alcohol protecting agent to provide a compound of formula (III-B).

In embodiments, the method further comprises
(iii) contacting a compound of formula (III-B) with an alkylating agent in the presence of a sterically hindered base to provide a compound of formula (IV), or

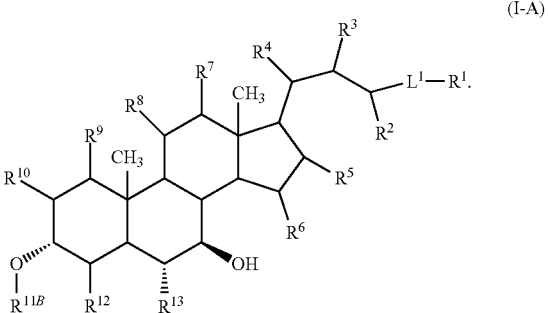

(I-A)

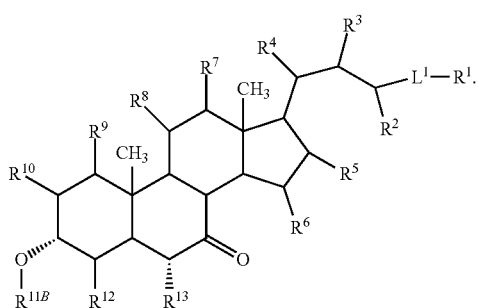

(IV)

In embodiments, the method further comprises
(vi) when the product of step (v) has a structure according to formula (I-A), contacting the compound of formula with an alcohol deprotecting agent to provide a compound of formula (I-A);

In embodiments, the method comprises
(i) contacting a compound of formula (II)

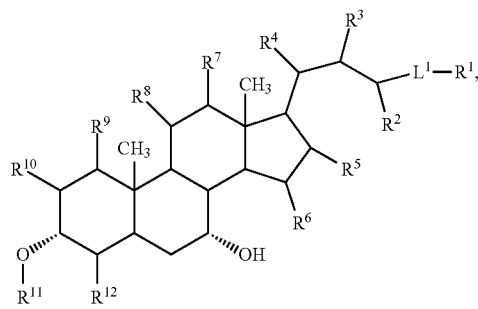

(II)

In embodiments, the method further comprises
(iv) optionally contacting the compound of formula (IV) with an alcohol deprotecting agent to provide a compound of formula (IV-A), wherein $R^{11}$ is $R^{11A}$, with an oxidizing reagent to provide a compound of formula (III-A),

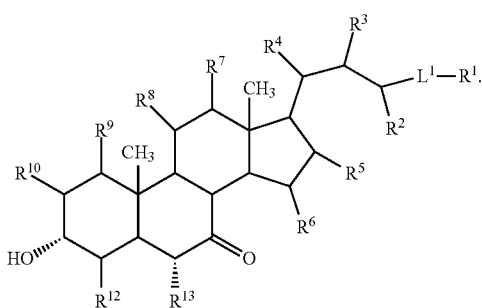

(IV-A)

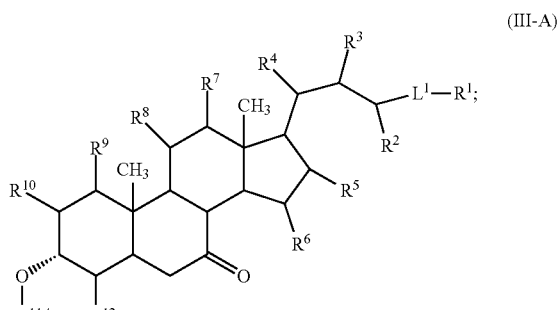

(III-A)

In embodiments, the method further comprises
(v) treatment of the compound of formula (IV) or (IV-A) with a reducing agent to provide a compound of formula (I) or (I-A), (ii) contacting the compound of formula (III-A) with an alcohol protecting agent to provide a compound of formula (III-B), (III-B)

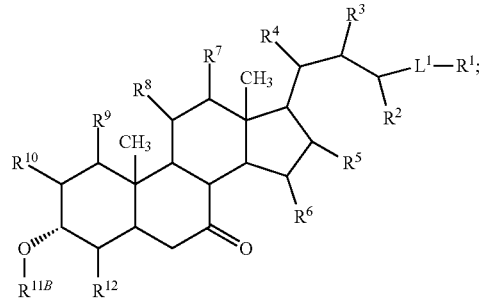

(iii) contacting a compound of formula (III-B) with an alkylating agent in the presence of a sterically hindered base to provide a compound of formula (IV), (IV)

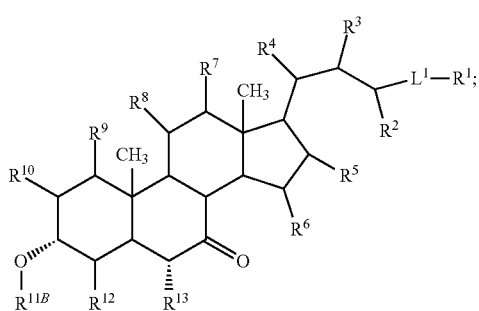

(iv) contacting the compound of formula (IV) with an alcohol deprotecting agent to provide a compound of formula (IV-A), (IV-A)

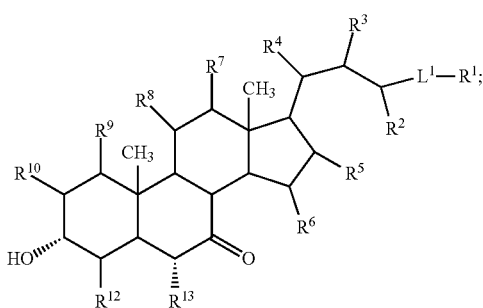

(v) treatment of the compound of formula (IV-A) with a reducing agent to provide a compound of formula (I), (I)

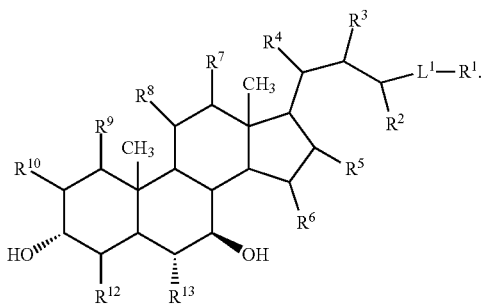

In embodiments, the method comprises,
(i) contacting a compound of formula (II)

(II)

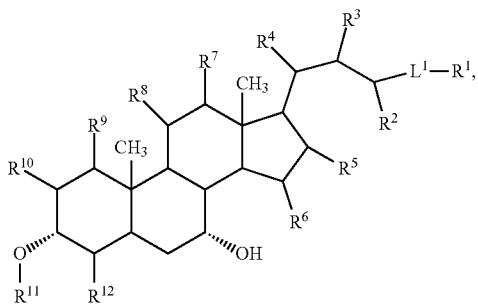

wherein $R^{11}$ is $R^{11B}$, with an oxidizing reagent to provide a compound of formula (III-B), (III-B)

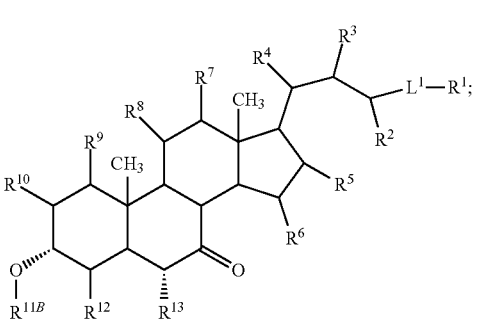

(iii) contacting a compound of formula (III-B) with an alkylating agent in the presence of a sterically hindered base to provide a compound of formula (IV), (IV)

(iv) contacting the compound of formula (IV) with an alcohol deprotecting agent to provide a compound of formula (IV-A),

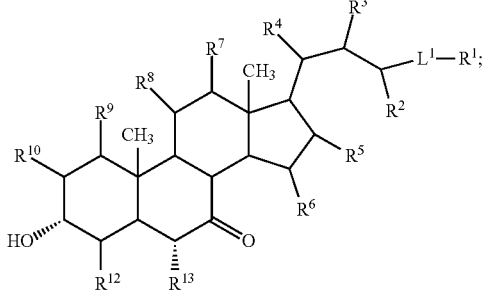

(IV-A)

and (v) treatment of the compound of formula (IV-A) with a reducing agent to provide a compound of formula (I)

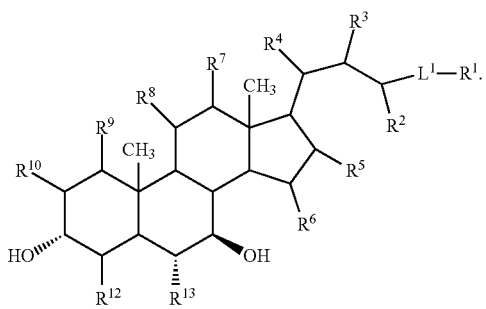

(I)

In embodiments, $R^{11B}$ is substituted or unsubstituted alkyl, substituted or unsubstituted heteroalkyl, substituted or unsubstituted heterocycloalkyl, or —SiR$^{11C}$R$^{11D}$R$^{11E}$, wherein R$^{11C}$, R$^{11D}$, and R$^{11E}$ are independently substituted or unsubstituted alkyl or substituted or unsubstituted aryl.

In embodiments, $R^{11B}$ is tetrahydropyranyl (THP).

In embodiments, the compound of formula (I) has the following structure,

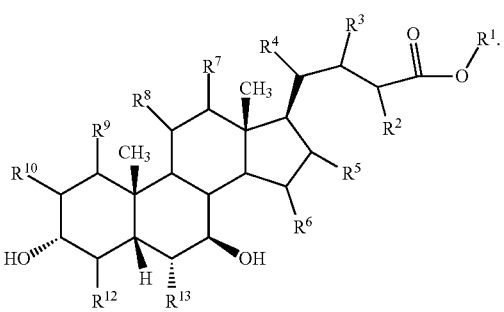

(I-C)

In embodiments, the compound of formula (I) has the following structure,

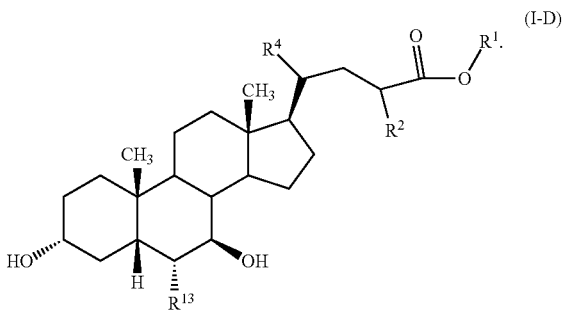

(I-D)

In embodiments, $R^1$ is hydrogen.
In embodiments, $R^2$ is hydrogen or unsubstituted alkyl.
In embodiments, $R^4$ is hydrogen or unsubstituted alkyl.
In embodiments, the compound of formula (I) has the following structure,

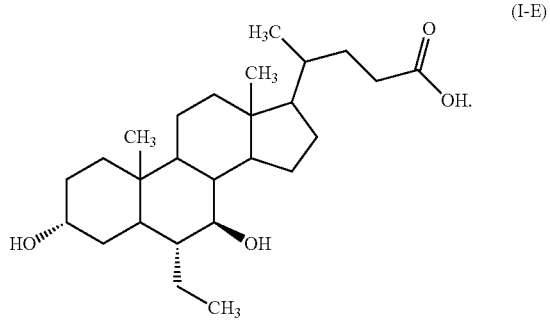 [SMILES: CC[C@@H]1C2C[C@H](O)CCC2(C)C2CCC3(C)C(C(C)CCC(=O)O)CCC3C2[C@H]1O]

(I-E)

In embodiments, the compound of formula (I) is 6-α-ethyl-ursodeoxycholic acid (6-EUDCA) having the following structure,

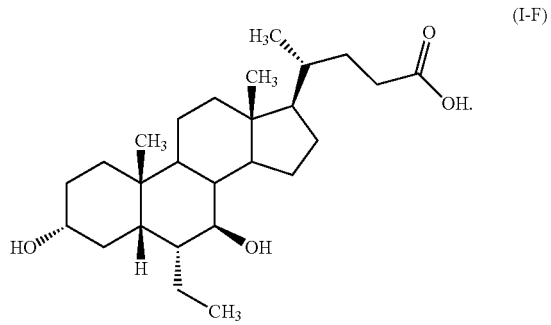

(I-F)

In embodiments, the oxidizing reagent of step (a) is a chromium oxidant, a ruthenium oxidant, a manganese oxidant, an activated dimethylsulfoxide oxidant, or a hypervalent iodine oxidant.

In embodiments, the oxidizing reagent is pyridinium chlorochromate (PCC).

In embodiments, the alcohol oxidation proceeds with greater than about 5:1, 6:1, 7:1, 8:1, 9:1, or 10:1 regioselectivity.

In embodiments, the sterically hindered base of step (iii) is lithium diisopropylamide (LDA), (M$^{+1}$)HMDS, (M$^{+1}$)tBuO, (M$^{+1}$)TMP, (M$^{+1}$)PhO, (M$^{+1}$)MeO, (M$^{+1}$)EtO, DBU, DABCO, N,N-dichlorohexylmethylamine, N,N-diisopropyl-2-ethylbutylamine, 2,6-di-tert-butyl-4-methylpyridine, pentamethylpiperidine, MTBD, PMDBD, TBD, or tri-tert-butylpyridine, wherein (M$^{+1}$) is Na, K, or Li.

In embodiments, the sterically hindered base is lithium diisopropylamide (LDA).

In embodiments, step (iii) comprises a second base.

In embodiments, the base is an alkyllithium reagent.

In embodiments, the alkylation agent of step (iii) is an alkyl halide.

In embodiments, the alkylation agent is an alkyl iodide.

In embodiments, step (iii) is performed in the presence of a polar aprotic solvent.

In embodiments, the polar aprotic solvent is HMPA, HMPT, DMF, DMSO, MeCN, dioxane, methylpyrrolidone, DMPU, or a tetra-alkyl urea.

In embodiments, the reducing agent of step (v) comprises an aluminum alkoxide and an alcohol.

In embodiments, the reducing agent comprises aluminium isopropoxide and isopropyl alcohol.

In embodiments, step (v) proceeds with greater than about 5:1, 6:1, 7:1, 8:1, 9:1, 10:1, 15:1, or 20:1 stereoselectivity.

In an aspect, the invention features a compound having a structure according to Formula (I) (e.g., Formula (I-C), (I-D), (I-E), or (I-F)), or a pharmaceutically acceptable salt thereof.

In an aspect, the invention features a pharmaceutical composition comprising a compound having a structure according to Formula (I) (e.g., Formula (I-C), (I-D), (I-E), or (I-F)), or a pharmaceutically acceptable salt thereof. In embodiments, the compound is 6-α-ethyl-ursodeoxycholic acid (6-EUDCA) having the following structure,

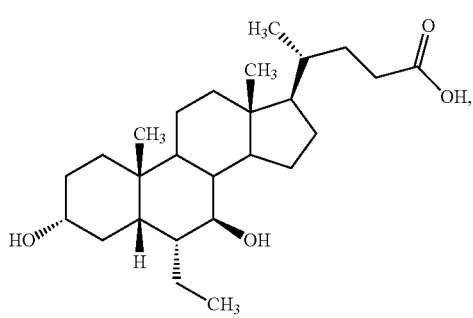

(I-F)

or a pharmaceutically acceptable salt thereof, and a pharmaceutically acceptable excipient.

In an aspect, the invention features an insulin peptide hormone covalently bonded to a compound of Formula (I), or a pharmaceutically acceptable salt thereof. In embodiments, the insulin peptide hormone is human insulin. In embodiments, the insulin peptide hormone has a sequence of SEQ ID NO: 1. In embodiments, lysine B29 of the insulin peptide hormone is covalently bonded to a compound of Formula (I). In embodiments, the compound of Formula (I) is a compound of Formula (I-C), Formula (I-D), Formula (I-E), or Formula (I-F). In embodiments, the compound of Formula (I) is 6-α-ethyl-ursodeoxycholic acid (6-EUDCA) having the following structure,

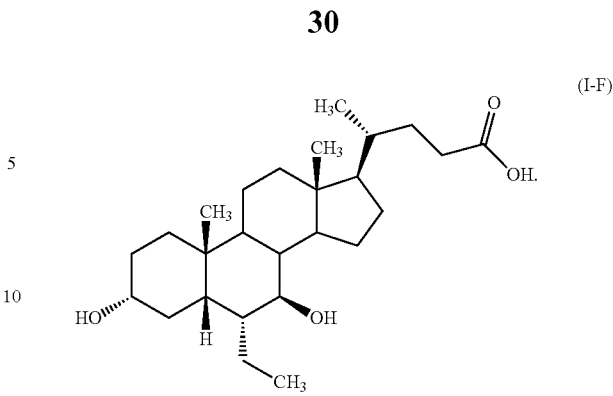

(I-F)

In an aspect, the invention features a compound having the following structure,

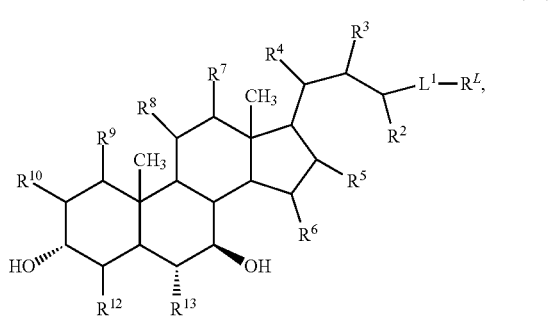

(I-1)

or a pharmaceutically acceptable salt thereof.

$L^1$ is —C(O)—, —C(O)O—, —C(O)NH—, or —CH$_2$—.

$R^L$ is $L^2$-$R^{L2}$.

$R^2$ is hydrogen or unsubstituted alkyl.

$R^3$ is hydrogen, unsubstituted alkyl, or —OR$^{3A}$.

$R^4$ is hydrogen, unsubstituted alkyl, or —OR$^{4A}$.

$R^5$ is hydrogen, unsubstituted alkyl, or —OR$^{5A}$.

$R^6$ is hydrogen, unsubstituted alkyl, or —OR$^{6A}$.

$R^7$ is hydrogen, unsubstituted alkyl, or —OR$^{7A}$.

$R^8$ is hydrogen, unsubstituted alkyl, or —OR$^{8A}$.

$R^9$ is hydrogen, unsubstituted alkyl, or —OR$^{9A}$.

$R^{10}$ is hydrogen, unsubstituted alkyl, or —OR$^{10A}$.

$R^{11A}$ is hydrogen.

$R^{11B}$ is an alcohol protecting group.

$R^{12}$ is hydrogen, unsubstituted alkyl, or —OR$^{12A}$.

$R^{13}$ is unsubstituted alkyl.

$R^{1A}$, $R^{3A}$, $R^{4A}$, $R^{5A}$, $R^{6A}$, $R^{7A}$, $R^{8A}$, $R^{9A}$, $R^{10A}$, $R^{12A}$ and $R^{13A}$ are independently hydrogen, unsubstituted alkyl, or an alcohol protecting group.

$L^2$ is a bond, —NR$^{L1}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

$R^{L1}$ is hydrogen or unsubstituted alkyl.

$R^{L2}$ is an amino acid of an insulin peptide hormone.

In embodiments, the compound of Formula (I-1) has the following structure,

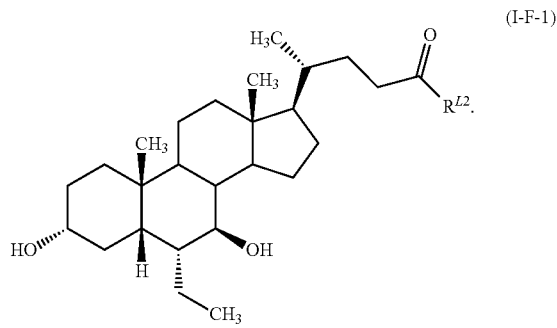

(I-F-1)

In embodiments, L² is a bond. In embodiments, $R^{L2}$ is lysine B29 of the insulin peptide hormone.

In embodiments, the insulin peptide hormone is human insulin. In embodiments, the insulin peptide hormone has the sequence of SEQ ID NO: 1.

In an aspect, the invention features a pharmaceutical composition comprising any of the compounds described herein (e.g., a compound of Formula (I) such as Formula (I-C), (I-D), (I-E), or (I-F); a compound of Formula (I-1); or an insulin peptide hormone as described herein), or a pharmaceutically acceptable salt thereof, and a pharmaceutically acceptable excipient. In embodiments, the pharmaceutical composition is formulated for oral administration. In embodiments, the compound is 6-α-ethyl-ursodeoxycholic acid (6-EUDCA) having the following structure,

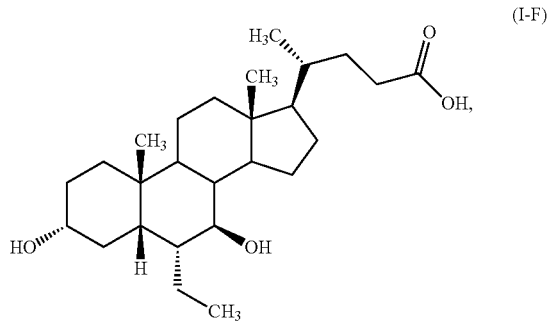 [SMILES: CC[C@H]1[C@H](O)C2C3CC[C@H]([C@H](C)CCC(=O)O)[C@@]3(C)CCC2[C@@]2(C)CC[C@@H](O)C[C@@H]12]

(I-F)

or a pharmaceutically acceptable salt thereof.

In another aspect is a method of treating or preventing diabetes, obesity, insulin resistance, or liver disease in a subject in need thereof. The method includes administering to the subject a therapeutically effective amount of a compound as described herein (e.g., a compound of Formula (I) such as Formula (I-C), (I-D), (I-E), or (I-F); a compound of Formula (I-1); or an insulin peptide hormone as described herein), including embodiments thereof. In embodiments, the method for treating includes administering to a subject in need thereof, a pharmaceutical composition of a compound as provided herein (e.g., a compound of Formula (I) such as Formula (I-C), (I-D), (I-E), or (I-F); a compound of Formula (I-1); or an insulin peptide hormone as described herein), including embodiments thereof. The pharmaceutical composition may include a pharmaceutically acceptable excipient. The administration may be performed intravenously or orally. The subject may be administered the compound for treating or preventing diabetes. In embodiments, the diabetes is type 2 (T2) diabetes. The subject may be administered the compound for treating or preventing obesity. The subject may be administered the compound for treating or preventing insulin resistance. In embodiments, the compound is 6-α-ethyl-ursodeoxycholic acid (6-EUDCA) having the following structure,

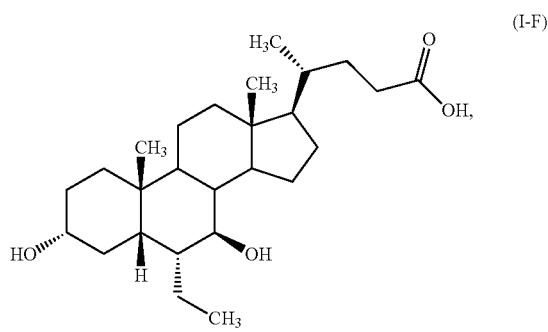 [SMILES: CC[C@H]1[C@H](O)C2C3CC[C@H]([C@H](C)CCC(=O)O)[C@@]3(C)CCC2[C@@]2(C)CC[C@@H](O)C[C@@H]12]

(I-F)

or a pharmaceutically acceptable salt thereof.

In another aspect is a method of treating or preventing cancer. The method includes administering to a subject in need thereof a therapeutically effective amount of a compound as described herein (e.g., a compound of Formula (I) such as Formula (I-C), (I-D), (I-E), or (I-F); a compound of Formula (I-1); or an insulin peptide hormone as described herein), including embodiments thereof. In embodiments, cancer is liver cancer. In embodiments, the compound is 6-α-ethyl-ursodeoxycholic acid (6-EUDCA) having the following structure,

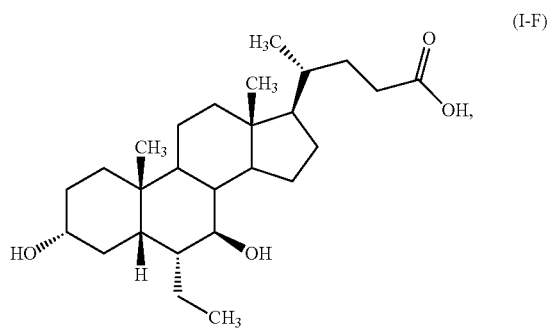 [SMILES: CC[C@H]1[C@H](O)C2C3CC[C@H]([C@H](C)CCC(=O)O)[C@@]3(C)CCC2[C@@]2(C)CC[C@@H](O)C[C@@H]12]

(I-F)

or a pharmaceutically acceptable salt thereof.

In an aspect, the invention features a method of modulating farnesoid X receptor (FXR) activity, said method comprising contacting the farnesoid X receptor (FXR) with an effective amount of a compound as described herein (e.g., a compound of Formula (I) such as Formula (I-C), (I-D), (I-E), or (I-F); a compound of Formula (I-1); or an insulin peptide hormone as described herein), including embodiments thereof. In embodiments, the compound is 6-α-ethyl-ursodeoxycholic acid (6-EUDCA) having the following structure,

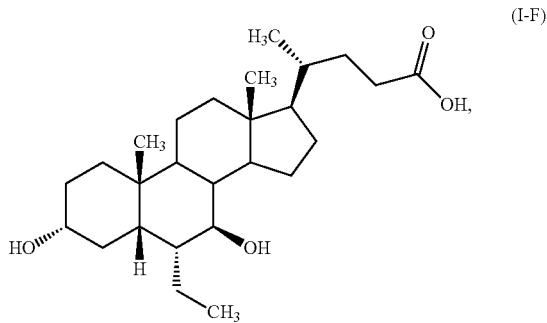 [SMILES: CC[C@H]1[C@H](O)C2C3CC[C@H]([C@H](C)CCC(=O)O)[C@@]3(C)CCC2[C@@]2(C)CC[C@@H](O)C[C@@H]12]

(I-F)

or a pharmaceutically acceptable salt thereof.

In an aspect, the invention features a method of treating a disorder or condition mediated by farnesoid X receptor (FXR) activity, said method comprising administering to a subject in need thereof an effective amount of a compound as described herein (e.g., a compound of Formula (I) such as Formula (I-C), (I-D), (I-E), or (I-F); a compound of Formula (I-1); or an insulin peptide hormone as described herein), including embodiments thereof. In embodiments, the compound is 6-α-ethyl-ursodeoxycholic acid (6-EUDCA) having the following structure,

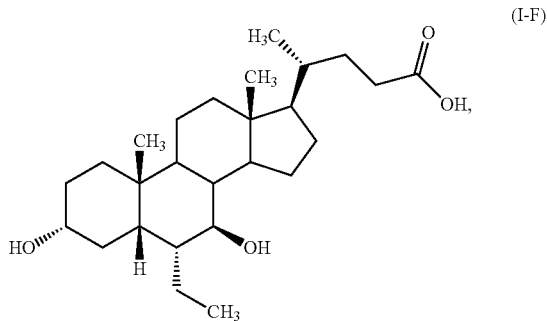 [SMILES: CC[C@H]1[C@H](O)C2C3CC[C@H]([C@H](C)CCC(=O)O)[C@@]3(C)CCC2[C@@]2(C)CC[C@@H](O)C[C@@H]12]

(I-F)

or a pharmaceutically acceptable salt thereof.

In embodiments, the disorder or condition mediated by farnesoid X receptor (FXR) activity is cardiovascular disease, atherosclerosis, arteriosclerosis, hypercholesteremia, or hyperlipidemiachronic liver disease, gastrointestinal disease, renal disease, cardiovascular disease, metabolic disease, cancer (i.e., colorectal cancer), or neurological indications such as stroke. In certain embodiments, the chronic liver disease is primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, or alpha 1-antitrypsin deficiency. In certain embodiments, the gastrointestinal disease is inflammatory bowel disease (IBD) (including Crohn's disease and ulcerative colitis), irritable bowel syndrome (IBS), bacterial overgrowth, malabsorption, post-radiation colitis, or microscopic colitis. In certain embodiments, the renal disease is diabetic nephropathy, focal segmental glomerulosclerosis (FSGS), hypertensive nephrosclerosis, chronic glomerulonephritis, chronic transplant glomerulopathy, chronic interstitial nephritis, or polycystic kidney disease. In certain embodiments, the cardiovascular disease is atherosclerosis, arteriosclerosis, dyslipidemia, hypercholesterolemia, or hypertriglyceridemia. In certain embodiments, the metabolic disease is insulin resistance, Type I and Type II diabetes, or obesity.

In embodiments, the disorder or condition is cholestasis, diabetes, or liver disease.

In embodiments, the disorder or condition is cholesterol gallstone disease (CGD).

In embodiments, the liver disease is nonalcoholic steatohepatitis (NASH).

In embodiments, the invention features a compound, method for preparing a compound, or use of a compound that is an epimer (e.g., a C7-epimer) of any of the compounds described herein. In embodiments, the invention features a C7-epimeric compound of any one of Formula (I), Formula (I-C), Formula (I-D), Formula (I-E), and Formula (I-F), respectively referred to as epi-Formula (I), epi-Formula (I-C), epi-Formula (I-D), epi-Formula (I-E), and epi-Formula (I-F). In embodiments, the invention features the use of a compound of epi-Formula (I) (e.g., epi-Formula (I-C), epi-Formula (I-D), epi-Formula (I-E), or epi-Formula (I-F)) in any of the embodiments described herein for the sue of a compound of Formula (I). In embodiments, the invention features a compound or use of a C7-epimeric compound that has the following structure,

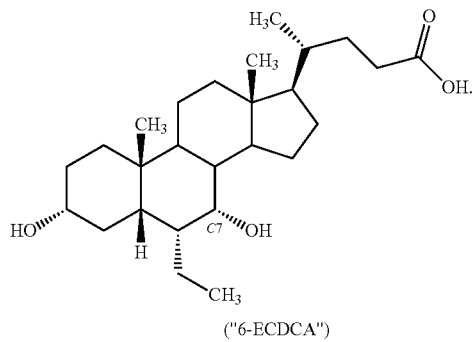

("6-ECDCA")

In embodiments, $L^1$ is —C(O)—. In embodiments, $L^1$ is —C(O)O—. In embodiments, $L^1$ is —C(O)NH—. In embodiments, $L^1$ is —CH$_2$—.

In embodiments, $R^1$ is hydrogen. In embodiments, $R^1$ is halogen. In embodiments, $R^1$ is —N$_3$. In embodiments, $R^1$ is —CF$_3$. In embodiments, $R^1$ is —CCl$_3$. In embodiments, $R^1$ is —CBr$_3$. In embodiments, $R^1$ is —CI$_3$. In embodiments, $R^1$ is —CN. In embodiments, $R^1$ is —CHO. In embodiments, $R^1$ is —OR$^{14}$. In embodiments, $R^1$ is —NHR$^{14}$. In embodiments, $R^1$ is —COOH, —CONH$_2$. In embodiments, $R^1$ is —NO$_2$. In embodiments, $R^1$ is —SH. In embodiments, $R^1$ is —SO$_2$Cl. In embodiments, $R^1$ is —SO$_3$H. In embodiments, $R^1$ is —SO$_4$H. In embodiments, $R^1$ is —SO$_2$NH$_2$. In embodiments, $R^1$ is —NHNH$_2$. In embodiments, $R^1$ is —ONH$_2$. In embodiments, $R^1$ is —NHC(O)NHNH$_2$. In embodiments, $R^1$ is substituted or unsubstituted alkyl. In embodiments, $R^1$ is substituted or unsubstituted heteroalkyl. In embodiments, $R^1$ is substituted or unsubstituted cycloalkyl. In embodiments, $R^1$ is substituted or unsubstituted heterocycloalkyl. In embodiments, $R^1$ is substituted or unsubstituted aryl. In embodiments, $R^1$ is substituted or unsubstituted heteroaryl, or a carboxylate protecting group. In embodiments, $R^1$ is independently substituted alkyl. In embodiments, $R^1$ is independently substituted heteroalkyl. In embodiments, $R^1$ is independently substituted cycloalkyl. In embodiments, $R^1$ is independently substituted heterocycloalkyl. In embodiments, $R^1$ is independently substituted aryl. In embodiments, $R^1$ is substituted heteroaryl. In embodiments, $R^1$ is independently unsubstituted alkyl. In embodiments, $R^1$ is independently unsubstituted heteroalkyl. In embodiments, $R^1$ is independently unsubstituted cycloalkyl. In embodiments, $R^1$ is independently unsubstituted heterocycloalkyl. In embodiments, $R^1$ is independently unsubstituted aryl. In embodiments, $R^1$ is unsubstituted heteroaryl. In embodiments, $R^1$ is independently substituted or unsubstituted $C_1$-$C_6$ alkyl. In embodiments, $R^1$ is independently substituted or unsubstituted 2 to 6 membered heteroalkyl. In embodiments, $R^1$ is independently substituted or unsubstituted $C_3$-$C_8$ cycloalkyl. In embodiments, $R^1$ is independently substituted or unsubstituted 3 to 8 membered heterocycloalkyl. In embodiments, $R^1$ is independently substituted or unsubstituted $C_6$ aryl. In embodiments, $R^1$ is independently substituted or unsubstituted 5 to 6 membered heteroaryl. In embodiments, $R^1$ is independently substituted $C_1$-$C_6$ alkyl. In embodiments, $R^1$ is independently substituted 2 to 6 membered heteroalkyl. In embodiments, $R^1$ is independently substituted $C_3$-$C_8$ cycloalkyl. In embodiments, $R^1$ is independently substituted 3 to 8 membered heterocycloalkyl. In embodiments, $R^1$ is independently substituted $C_6$ aryl. In embodiments, $R^1$ is independently substituted 5 to 6 membered heteroaryl. In embodiments, $R^1$ is independently unsubstituted $C_1$-$C_6$ alkyl. In embodiments, $R^1$ is independently unsubstituted 2 to 6 membered heteroalkyl. In embodiments, $R^1$ is independently unsubstituted $C_3$-$C_8$ cycloalkyl. In embodiments, $R^1$ is independently unsubstituted 3 to 8 membered heterocycloalkyl. In embodiments, $R^1$ is independently unsubstituted $C_6$ aryl. In embodiments, $R^1$ is independently unsubstituted 5 to 6 membered heteroaryl.

In embodiments, $R^2$ is independently hydrogen. In embodiments, $R^2$ is independently unsubstituted alkyl. In embodiments, $R^2$ is independently unsubstituted $C_1$-$C_6$ alkyl.

In embodiments, $R^3$ is independently hydrogen. In embodiments, $R^3$ is independently unsubstituted alkyl. In embodiments, $R^3$ is independently —$OR^{3A}$. In embodiments, $R^3$ is independently unsubstituted $C_1$-$C_6$ alkyl.

In embodiments, $R^4$ is independently hydrogen. In embodiments, $R^4$ is independently unsubstituted alkyl. In embodiments, $R^4$ is independently —$OR^{4A}$. In embodiments, $R^4$ is independently unsubstituted $C_1$-$C_6$ alkyl.

In embodiments, $R^5$ is independently hydrogen. In embodiments, $R^5$ is independently unsubstituted alkyl. In embodiments, $R^5$ is independently —$OR^{5A}$. In embodiments, $R^5$ is independently unsubstituted $C_1$-$C_6$ alkyl.

In embodiments, $R^6$ is independently hydrogen. In embodiments, $R^6$ is independently unsubstituted alkyl. In embodiments, $R^6$ is independently —$OR^{6A}$. In embodiments, $R^6$ is independently unsubstituted $C_1$-$C_6$ alkyl.

In embodiments, $R^7$ is independently hydrogen. In embodiments, $R^7$ is independently unsubstituted alkyl. In embodiments, $R^7$ is independently —$OR^{7A}$. In embodiments, $R^7$ is independently unsubstituted $C_1$-$C_6$ alkyl.

In embodiments, $R^8$ is independently hydrogen. In embodiments, $R^8$ is independently unsubstituted alkyl. In embodiments, $R^8$ is independently —$OR^{8A}$. In embodiments, $R^8$ is independently unsubstituted $C_1$-$C_6$ alkyl.

In embodiments, $R^9$ is independently hydrogen. In embodiments, $R^9$ is independently unsubstituted alkyl. In embodiments, $R^9$ is independently —$OR^{9A}$. In embodiments, $R^9$ is independently unsubstituted $C_1$-$C_6$ alkyl.

In embodiments, $R^{10}$ is independently hydrogen. In embodiments, $R^{10}$ is independently unsubstituted alkyl. In embodiments, $R^{10}$ is independently —$OR^{10A}$. In embodiments, $R^{10}$ is independently unsubstituted $C_1$-$C_6$ alkyl.

In embodiments, $R^{12}$ is independently hydrogen. In embodiments, $R^{12}$ is independently unsubstituted alkyl. In embodiments, $R^{12}$ is independently —$OR^{12A}$. In embodiments, $R^{12}$ is independently unsubstituted $C_1$-$C_6$ alkyl.

In embodiments, $R^{13}$ is independently unsubstituted alkyl. In embodiments, $R^{13}$ is independently unsubstituted $C_1$-$C_6$ alkyl.

In embodiments, $R^{1A}$ is independently hydrogen. In embodiments, $R^{1A}$ is independently unsubstituted alkyl. In embodiments, $R^{1A}$ is independently unsubstituted $C_1$-$C_6$ alkyl. In embodiments, $R^{1A}$ is independently an alcohol protecting group.

In embodiments, $R^{3A}$ is independently hydrogen. In embodiments, $R^{3A}$ is independently unsubstituted alkyl. In embodiments, $R^{3A}$ is independently unsubstituted $C_1$-$C_6$ alkyl. In embodiments, $R^{3A}$ is independently an alcohol protecting group.

In embodiments, $R^{4A}$ is independently hydrogen. In embodiments, $R^{4A}$ is independently unsubstituted alkyl. In embodiments, $R^{4A}$ is independently unsubstituted $C_1$-$C_6$ alkyl. In embodiments, $R^{4A}$ is independently an alcohol protecting group.

In embodiments, $R^{5A}$ is independently hydrogen. In embodiments, $R^{5A}$ is independently unsubstituted alkyl. In embodiments, $R^{5A}$ is independently unsubstituted $C_1$-$C_6$ alkyl. In embodiments, $R^{5A}$ is independently an alcohol protecting group.

In embodiments, $R^{6A}$ is independently hydrogen. In embodiments, $R^{6A}$ is independently unsubstituted alkyl. In embodiments, $R^{6A}$ is independently unsubstituted $C_1$-$C_6$ alkyl. In embodiments, $R^{6A}$ is independently an alcohol protecting group.

In embodiments, $R^{7A}$ is independently hydrogen. In embodiments, $R^{7A}$ is independently unsubstituted alkyl. In embodiments, $R^{7A}$ is independently unsubstituted $C_1$-$C_6$ alkyl. In embodiments, $R^{7A}$ is independently an alcohol protecting group.

In embodiments, $R^{8A}$ is independently hydrogen. In embodiments, $R^{8A}$ is independently unsubstituted alkyl. In embodiments, $R^{8A}$ is independently unsubstituted $C_1$-$C_6$ alkyl. In embodiments, $R^{8A}$ is independently an alcohol protecting group.

In embodiments, $R^{9A}$ is independently hydrogen. In embodiments, $R^{9A}$ is independently unsubstituted alkyl. In embodiments, $R^{9A}$ is independently unsubstituted $C_1$-$C_6$ alkyl. In embodiments, $R^{9A}$ is independently an alcohol protecting group.

In embodiments, $R^{10A}$ is independently hydrogen. In embodiments, $R^{10A}$ is independently unsubstituted alkyl. In embodiments, $R^{10A}$ is independently unsubstituted $C_1$-$C_6$ alkyl. In embodiments, $R^{10A}$ is independently an alcohol protecting group.

In embodiments, $R^{12A}$ is independently hydrogen. In embodiments, $R^{12A}$ is independently unsubstituted alkyl. In embodiments, $R^{12A}$ is independently unsubstituted $C_1$-$C_6$ alkyl. In embodiments, $R^{12A}$ is independently an alcohol protecting group.

In embodiments, $R^{13A}$ is independently hydrogen. In embodiments, $R^{13A}$ is independently unsubstituted alkyl. In embodiments, $R^{13A}$ is independently unsubstituted $C_1$-$C_6$ alkyl. In embodiments, $R^{13A}$ is independently an alcohol protecting group.

In embodiments, $L^2$ is a bond. In embodiments, $L^2$ is —$NR^{L1}$—. In embodiments, $L^2$ is substituted or unsubstituted alkylene. In embodiments, $L^2$ is substituted or unsubstituted heteroalkylene. In embodiments, $L^2$ is substituted or unsubstituted cycloalkylene. In embodiments, $L^2$ is substituted or unsubstituted heterocycloalkylene. In embodiments, $L^2$ is substituted or unsubstituted arylene. In embodiments, $L^2$ is substituted or unsubstituted heteroarylene. In embodiments, $L^2$ is independently substituted alkylene. In embodiments, $L^2$ is independently substituted heteroalkylene. In embodiments, $L^2$ is independently substituted cycloalkylene. In embodiments, $L^2$ is independently substituted heterocycloalkylene. In embodiments, $L^2$ is independently substituted arylene. In embodiments, $L^2$ is independently substituted heteroarylene. In embodiments, $L^2$ is independently unsubstituted alkylene. In embodiments, $L^2$ is independently unsubstituted heteroalkylene. In embodiments, $L^2$ is independently unsubstituted cycloalkylene. In embodiments, $L^2$ is independently unsubstituted heterocycloalkylene. In embodiments, $L^2$ is independently unsubstituted arylene. In embodiments, $L^2$ is independently unsubstituted heteroarylene. In embodiments, $L^2$ is independently substituted or unsubstituted $C_1$-$C_6$ alkylene. In embodiments, $L^2$ is independently substituted or unsubstituted 2 to 6 membered heteroalkylene. In embodiments, $L^2$ is independently substituted or unsubstituted $C_3$-$C_8$ cycloalkylene. In embodiments, $L^2$ is independently substituted or unsubstituted 3 to 8 membered heterocycloalkylene. In embodiments, $L^2$ is independently substituted or unsubstituted $C_6$ arylene. In embodiments, $L^2$ is independently substituted or unsubstituted 5 to 6 membered heteroarylene. In embodiments, $L^2$ is independently substituted $C_1$-$C_6$ alkylene. In embodiments, $L^2$ is independently substituted 2 to 6 membered heteroalkylene. In embodiments, $L^2$ is independently substituted $C_3$-$C_8$ cycloalkylene. In embodiments, $L^2$ is independently substituted 3 to 8 membered heterocycloalkylene. In embodiments, $L^2$ is independently substituted $C_6$ arylene. In embodiments, $L^2$ is independently substituted 5 to 6 membered heteroarylene. In embodiments, $L^2$ is independently unsubstituted $C_1$-$C_6$ alkylene. In embodiments, $L^2$ is independently unsubstituted 2 to 6 membered heteroalkylene. In embodiments, $L^2$ is independently unsubstituted $C_3$-$C_8$ cycloalkylene. In embodiments, $L^2$ is independently unsubstituted 3 to 8 membered heterocycloalkylene. In embodiments, $L^2$ is independently unsubstituted $C_6$ arylene. In embodiments, $L^2$ is independently unsubstituted 5 to 6 membered heteroarylene.

In embodiments, $R^{L1}$ is hydrogen. In embodiments, $R^{L1}$ is unsubstituted alkyl. In embodiments, $R^{L1}$ is unsubstituted $C_1$-$C_6$ alkyl.

In embodiments, $R^1$ is independently hydrogen, halogen, —$N_3$, —$CF_3$, —$CCl_3$, —$CBr_3$, —$CI_3$, —CN, —CHO, —$OR^{1A}$, —$NHR^{1A}$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, $R^{14}$-substituted or unsubstituted alkyl, $R^{14}$-substituted or unsubstituted heteroalkyl, $R^{14}$-substituted or unsubstituted cycloalkyl, $R^{14}$-substituted or unsubstituted heterocycloalkyl, $R^{14}$-substituted or unsubstituted aryl, or $R^{14}$-substituted or unsubstituted heteroaryl, or a carboxylate protecting group.

$R^{14}$ is independently oxo, halogen, —$CX^{14}_3$, —$CHX^{14}_2$, —$CH_2X^{14}$, —$OCX^{14}_3$, —$OCHX^{14}_2$, —$OCH_2X^{14}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC=(O)NHNH_2$, —$NHC=(O)NH_2$, —$NHSO_2H$, —$NHC=(O)H$, —NHC(O)—OH, —NHOH, $R^{15}$-substituted or unsubstituted alkyl, $R^{15}$-substituted or unsubstituted heteroalkyl, $R^{15}$-substituted or unsubstituted cycloalkyl, $R^{15}$-substituted or unsubstituted heterocycloalkyl, $R^{15}$-substituted or unsubstituted aryl, or $R^{15}$-substituted or unsubstituted heteroaryl. $X^{14}$ is halogen. In embodiments, $X^{14}$ is F.

In embodiments, $L^2$ is a bond, —$NR^{L1}$—, $R^{16}$-substituted or unsubstituted alkylene, $R^{16}$-substituted or unsubstituted heteroalkylene, $R^{16}$-substituted or unsubstituted cycloalkylene, $R^{16}$-substituted or unsubstituted heterocycloalkylene, $R^{16}$-substituted or unsubstituted arylene, or $R^{16}$-substituted or unsubstituted heteroarylene.

$R^{16}$ is independently oxo, halogen, —$CX^{16}_3$, —$CHX^{16}_2$, —$CH_2X^{16}$, —$OCX^{16}_3$, —$OCHX^{16}_2$, —$OCH_2X^{16}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC=(O)NHNH_2$, —$NHC=(O)NH_2$, —$NHSO_2H$, —$NHC=(O)H$, —NHC(O)—OH, —NHOH, $R^{17}$-substituted or unsubstituted alkyl, $R^{17}$-substituted or unsubstituted heteroalkyl, $R^{17}$-substituted or unsubstituted cycloalkyl, $R^{17}$-substituted or unsubstituted heterocycloalkyl, $R^{17}$-substituted or unsubstituted aryl, or $R^{17}$-substituted or unsubstituted heteroaryl. $X^{16}$ is halogen. In embodiments, $X^{16}$ is F.

$R^{15}$ and $R^{17}$ are independently hydrogen, oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC=(O)NHNH_2$, —$NHC=(O)NH_2$, —$NHSO_2H$, —$NHC=(O)H$, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.

The present invention is generally related to compounds having activity as FXR modulators, specifically—UDCA derivatives which are not genomically available, as well as methods of preparing these compounds. The compounds described herein are useful for treatment of, e.g., FXR mediated diseases or conditions, including cholesterol gallstone disease (CGD). Moreover, this invention allows for the first time a pharmacological differentiation of genomic versus non-genomic effects of FXR mediated by UDCA and its derivatives.

Metabolic disorder (including diabetes) is a known high risk factor for developing cholesterol gallstone disease (CGD). Cholesterol gallstone disease (CGD) is one of the most prevalent digestive diseases, leading to considerable financial and social burden worldwide. Ursodeoxycholic acid (UDCA) is the only bile acid drug approved by FDA for the non-surgical treatment of gallstones. However, a molecular link between UDCA and CGD is unclear. Data suggest that farnesoid X receptor (FXR), a bile acid nuclear receptor, could protect against the development of CGD.

In studies aimed at identifying the role of FXR in disease research, we have identified a novel chemical tool, 6EUDCA (6-αethyl-ursodeoxycholic acid), a synthetic derivative of UDCA, for the FXR. We found that 6EUDCA binds FXR better than UDCA. This is supported by computational docking models that suggest 6EUDCA forms a more extensive hydrogen bond network with FXR. Interestingly, neither compound could activate FXR target genes in human and mouse liver cells, indicating that UDCA and 6EUDCA activate non-genomic signals in an FXR-dependent manner. Collectively, these data suggest that a novel mechanism of action for these FXR modulators and 6EUDCA may be an effective targeted CGD therapeutic.

Cholesterol gallstone disease is more prevalent in people consuming western diets (Reference 1). Gallstones are formed in the gallbladder when a super saturation of bile cholesterol precipitates as crystals. In the presence of mucin, cholesterol crystals nucleate and grow to form gallstones, which can cause severe abdominal pain and gallbladder inflammation. Currently, the treatment for gallstones is laproscopic cholecystectomy, which is one of the most commonly performed surgical procedures worldwide. However, cholecystectomy is invasive and can cause surgical complications in terms of morbidity and mortality and not all patients with symptomatic gallstones are candidates for surgery. Earlier studies have provided evidence for dissolution of cholesterol gallstones using ursodeoxycholic acid (UDCA; Reference 2), which is the only bile acid drug that has been approved by the US FDA for treating liver diseases, including primary biliary cirrhosis and CGD (Reference 3).

UDCA (FIG. 1) is a naturally occurring bile acid, derived from cholesterol. It has been shown to alter lipid, glucose and bile acid metabolism (Reference 3). Indeed, for centuries, bile acids have played important roles in elucidating the mechanisms of metabolic disorders (Reference 4). However, the mechanism by which UDCA works on cholesterol gallstones is unknown. Our data indicate that the farnesoid X receptor (FXR, NR1H4) plays a role in protecting against the development of gallstone diseases (Reference 5). Consequently, ligands that bind and activate FXR may be potential therapeutic agents (Reference 6).

FXR is a bile acid nuclear receptor that is highly expressed in the liver and gut (Reference 7). Studies from several laboratories have demonstrated FXR serves as a key metabolic integrator that regulates cholesterol, triglyceride, and glucose homeostasis (Reference 8). Bile acids are endogenous signals that can act as FXR ligands (Reference 9) and have been shown to reduce adiposity and plasma triglycerides as well as promote insulin sensitization (Reference 10). The bile acid chenodeoxycholic acid (CDCA) (FIG. 1) is one of the most potent endogenous agonists for FXR ($EC_{50}$~13 μM). However, CDCA is poorly effective as a therapeutic agent because of its toxicity and its promiscuity in activating the intestine expressed G-protein-coupled receptor TGR5 (Reference 11). In contrast, the hydrophilic bile acid UDCA is a widely used therapeutic agent that has minimal side effects (Reference 12).

The available data suggest that UDCA can treat and protect against gallstones, but its molecular target is unknown. Recent studies indicated that UDCA could be working through a nuclear receptor, the glucocorticoid receptor (GR), but these studies did not show that UDCA directly binds to GR (Reference 12). Others have shown that UDCA binds to FXR expressed in CHOK1 cells, and UDCA may regulate constitutively expressed IBABP (ileal bile acid binding protein) in Caco-2 cells. This suggests that UDCA acts as a partial agonist through an FXR mediated mechanism (Reference 13). Because activation of FXR through its ligands could control the formation of gallstones (Reference 14), it follows that UDCA may have a key role in treating gallstones with distinct molecular signatures via FXR. However, as reported, UDCA is a weak modulator of FXR and has limited clinical efficacy, there is thus a need to develop more potent and higher affinity small molecules that target the FXR for the treatment of diseases and conditions such as, for example, CGD.

EMBODIMENTS

Embodiments contemplated herein include embodiments P1 to P42 following.

Embodiment P1

A method of synthesizing a compound having the following structure,

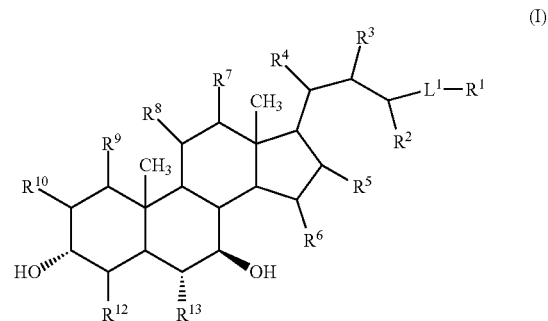

(I)

the method comprising, (i) contacting a compound of formula (II)

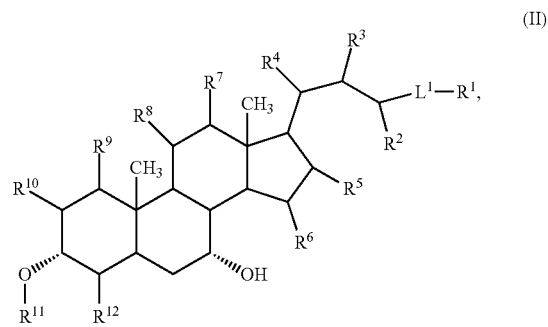

(II)

wherein $R^{11}$ is $R^{11A}$ or $R^{11B}$, with an oxidizing reagent to provide a compound of formula (III-A) or (III-B),

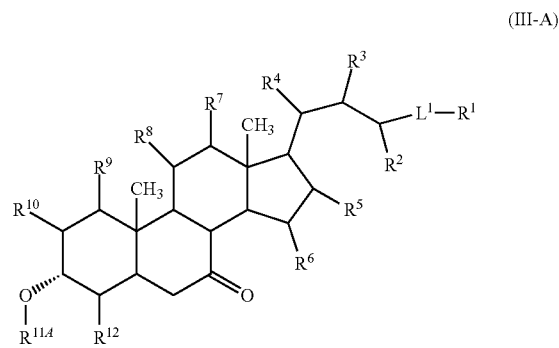

(III-A)

or

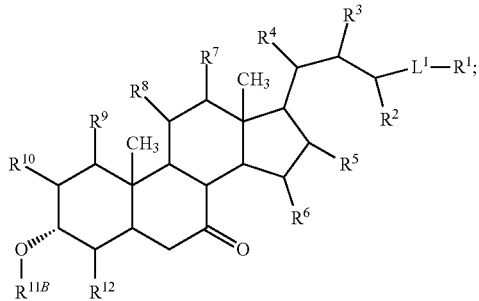
(III-B)

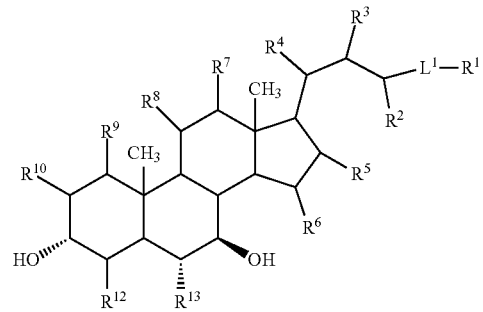
(I)

(ii) when the product of step (i) has a structure according to formula (III-A), contacting the compound of formula (III-A) with an alcohol protecting agent to provide a compound of formula (III-B);

(iii) contacting a compound of formula (III-B) with an alkylating agent in the presence of a sterically hindered base to provide a compound of formula (IV),

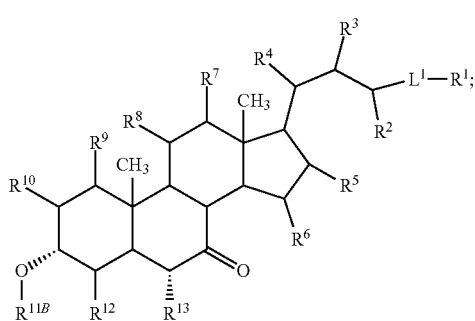
(IV)

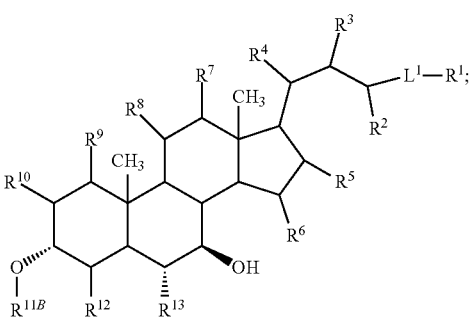
(I-A)

(iv) optionally contacting the compound of formula (IV) with an alcohol deprotecting agent to provide a compound of formula (IV-A),

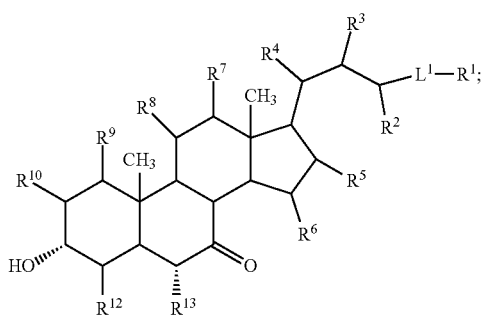
(IV-A)

(v) treatment of the compound of formula (IV) or (IV-A) with a reducing agent to provide a compound of formula (I) or (I-A), and (vi) when the product of step (v) has a structure according to formula (I-A), contacting the compound of formula with an alcohol deprotecting agent to provide a compound of formula (I-A).

$L^1$ is —C(O)—, —C(O)O—, —C(O)NH—, or —CH$_2$—. $R^1$ is hydrogen, halogen, —N$_3$, —CF$_3$, —CCl$_3$, —CBr$_3$, —CI$_3$, —CN, —CHO, —OR$^{1A}$, —NHR$^{1A}$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a carboxylate protecting group. $R^2$ is hydrogen or unsubstituted alkyl. $R^3$ is hydrogen, unsubstituted alkyl, or —OR$^{3A}$. $R^4$ is hydrogen, unsubstituted alkyl, or —OR$^{4A}$. $R^5$ is hydrogen, unsubstituted alkyl, or —OR$^{5A}$. $R^6$ is hydrogen, unsubstituted alkyl, or —OR$^{6A}$. $R^7$ is hydrogen, unsubstituted alkyl, or —OR$^{7A}$. $R^8$ is hydrogen, unsubstituted alkyl, or —OR$^{8A}$. $R^9$ is hydrogen, unsubstituted alkyl, or —OR$^{9A}$. $R^{10}$ is hydrogen, unsubstituted alkyl, or —OR$^{10A}$. $R^{11A}$ is hydrogen. $R^{11B}$ is an alcohol protecting group. $R^{12}$ is hydrogen, unsubstituted alkyl, or —OR$^{12A}$. $R^{13}$ is unsubstituted alkyl. $R^{1A}$, $R^{3A}$, $R^{4A}$, $R^{5A}$, $R^{6A}$, $R^{7A}$, $R^{8A}$, $R^{9A}$, $R^{10A}$, $R^{12A}$, and $R^{13A}$ are independently hydrogen, unsubstituted alkyl, or an alcohol protecting group.

Embodiment P2

The method of embodiment P1, the method comprising,
(i) contacting a compound of formula (II)

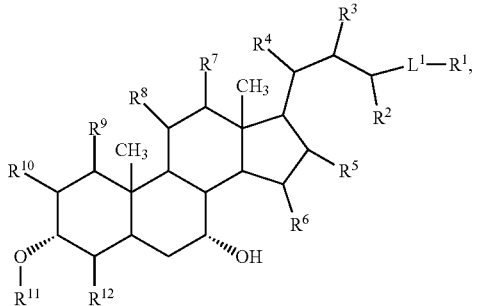
(II)

wherein $R^{11}$ is $R^{11A}$, with an oxidizing reagent to provide a compound of formula (III-A),

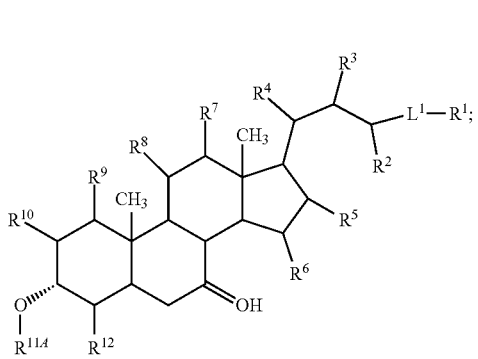
(III-A)

(ii) contacting the compound of formula (III-A) with an alcohol protecting agent to provide a compound of formula (III-B),

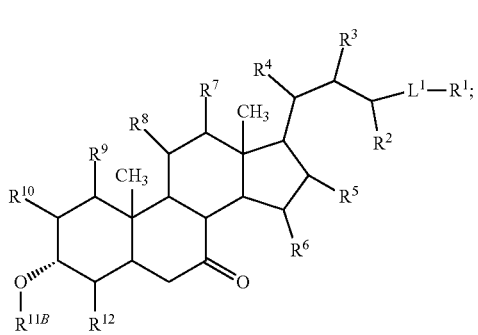
(III-B)

(iii) contacting a compound of formula (III-B) with an alkylating agent in the presence of a sterically hindered base to provide a compound of formula (IV),

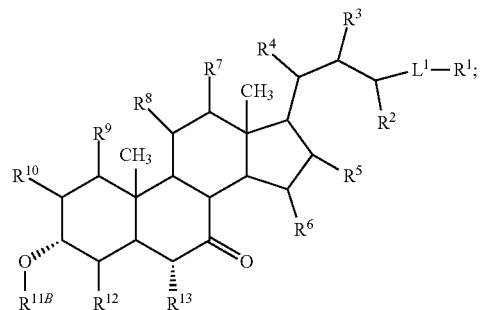
(IV)

(iv) contacting the compound of formula (IV) with an alcohol deprotecting agent to provide a compound of formula (IV-A),

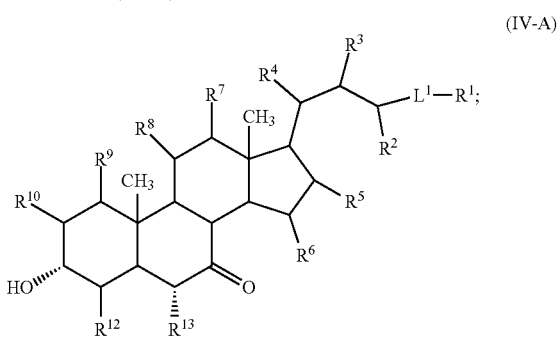
(IV-A)

(v) treatment of the compound of formula (IV-A) with a reducing agent to provide a compound of formula (I),

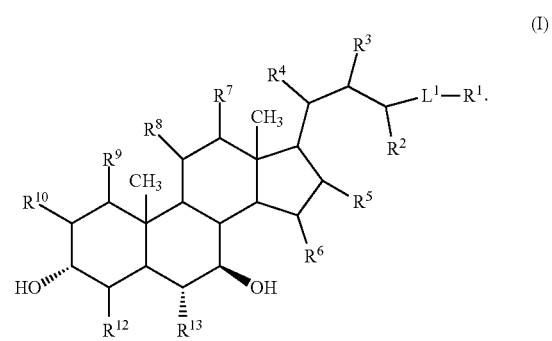
(I)

Embodiment P3

The method of embodiment P1, the method comprising,
(i) contacting a compound of formula (II)

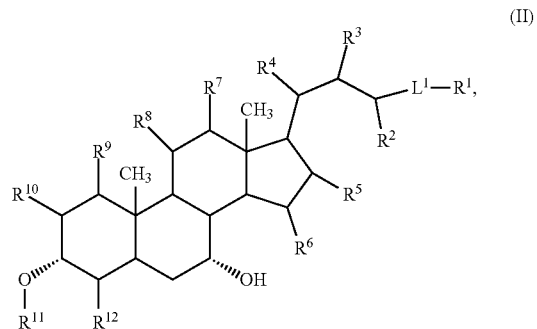
(II)

wherein R¹¹ is R¹¹ᴮ, with an oxidizing reagent to provide a compound of formula (III-B),

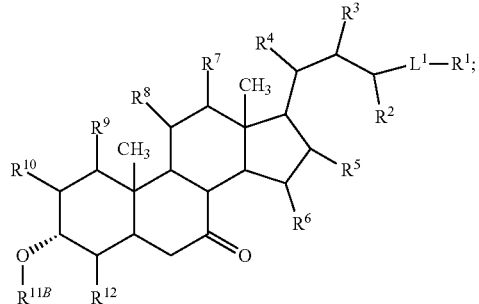
(III-B)

(ii) contacting a compound of formula (III-B) with an alkylating agent in the presence of a sterically hindered base to provide a compound of formula (IV),

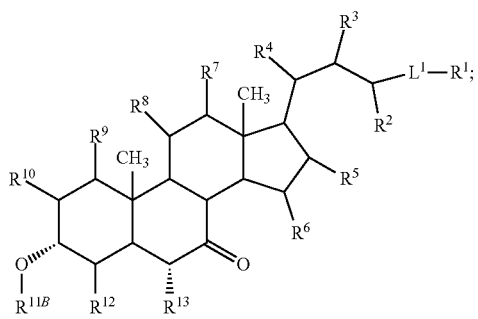
(IV)

(iii) contacting the compound of formula (IV) with an alcohol deprotecting agent to provide a compound of formula (IV-A),

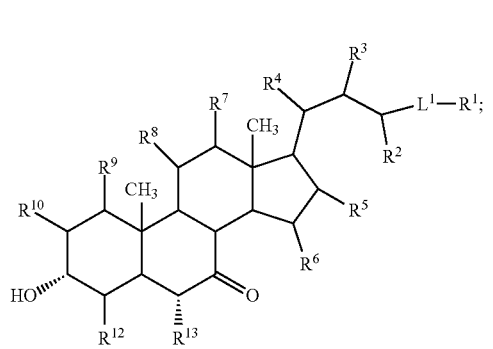
(IV-A)

(iv) treatment of the compound of formula (IV-A) with a reducing agent to provide a compound of formula (I)

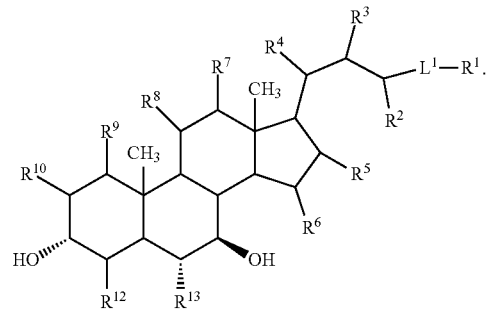
(I)

Embodiment P4

The method of any one of embodiments P1 to P3, wherein $R^{11B}$ is substituted or unsubstituted alkyl, substituted or unsubstituted heteroalkyl, substituted or unsubstituted heterocycloalkyl, or —SiR¹¹ᶜR¹¹ᴰR¹¹ᴱ, wherein $R^{11C}$, $R^{11D}$, and $R^{11E}$ are independently substituted or unsubstituted alkyl or substituted or unsubstituted aryl.

Embodiment P5

The method of embodiment P4, wherein $R^{11B}$ is tetrahydropyranyl (THP).

Embodiment P6

The method of any one of embodiments P1 to P5, wherein the compound of formula (I) has the following structure,

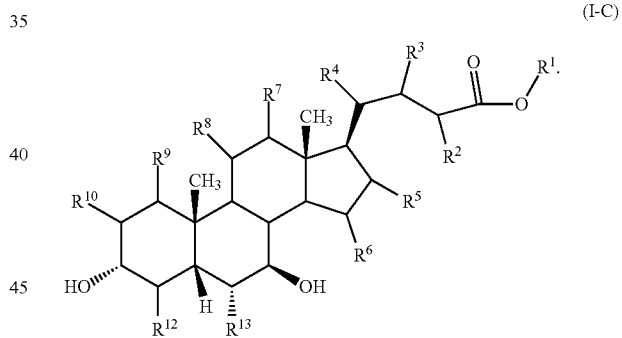
(I-C)

Embodiment P7

The method of any one of embodiments P1 to P5 wherein the compound of formula (I) has the following structure,

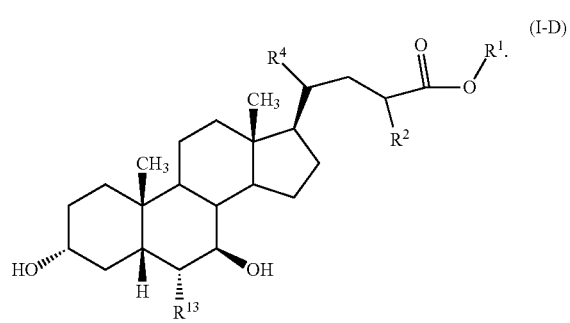
(I-D)

Embodiment P8

The method of embodiment P7, wherein
$R^1$ is hydrogen;
$R^2$ is hydrogen or unsubstituted alkyl; and
$R^4$ is hydrogen or unsubstituted alkyl.

Embodiment P9

The method of any one of embodiments P 1 to P8, wherein the compound of formula (I) has the following structure,

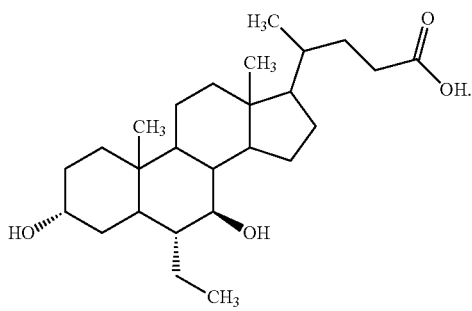

(I-E)

Embodiment P10

The method of embodiment P9, wherein the compound of formula (I) is 6-α-ethyl-ursodeoxycholic acid (6-EUDCA) having the following structure,

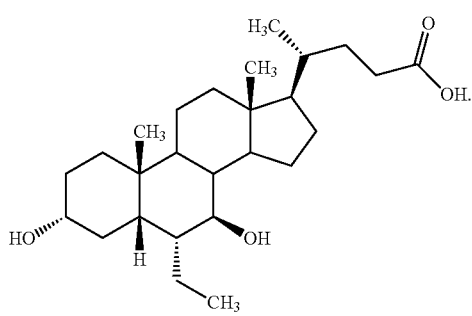

(I-F)

Embodiment P11

The method of any one of embodiments P1 to P10, wherein the oxidizing reagent of step (a) is a chromium oxidant, a ruthenium oxidant, a manganese oxidant, an activated dimethylsulfoxide oxidant, or a hypervalent iodine oxidant.

Embodiment P12

The method of embodiment P11, wherein the oxidizing reagent is pyridinium chlorochromate (PCC).

Embodiment P13

The method of any one of embodiments P1 to P12, wherein the alcohol oxidation proceeds with greater than about 5:1, 6:1, 7:1, 8:1, 9:1, or 10:1 regioselectivity.

Embodiment P14

The method of any one of embodiments P1 to P13, wherein said sterically hindered base of step (iii) is lithium diisopropylamide (LDA), $(M^{+1})$HMDS, $(M^{-1})$tBuO, $(M^{+1})$TMP, $(M^{+1})$PhO, $(M^{+1})$MeO, $(M^{+1})$EtO, DBU, Dabco, N,N-dichlorohexylmethyl amine, N,N-diisopropyl-2-ethylbutylamine, 2,6-di-tert-butyl-4-methylpyridine, pentamethylpiperidine, MTBD, PMDBD, TBD, or tri-tert-butylpyridine, wherein $(M^{+1})$ is Na, K, or Li.

Embodiment P15

The method of embodiment P 14, wherein said sterically hindered base is lithium diisopropylamide (LDA).

Embodiment P16

The method of any one of embodiments P1 to 15, wherein step (iii) comprises a second base.

Embodiment P17

The method of embodiment P 16, wherein said base is an alkyllithium reagent.

Embodiment P18

The method of any one of embodiments P1 to P17, wherein said alkylation agent of step (iii) is an alkyl halide.

Embodiment P19

The method of embodiment P18, wherein said alkylation agent is an alkyl iodide.

Embodiment P20

The method of any one of embodiments P1 to P19, wherein step (iii) is performed in the presence of a polar aprotic solvent.

Embodiment P21

The method of embodiment P20, wherein said polar aprotic solvent is HMPA, HMPT, DMF, DMSO, MeCN, dioxane, methylpyrrolidone, DMPU, or a tetra-alkyl urea.

Embodiment P22

The method of any one of embodiments P1 to P21, wherein the reducing agent of step (v) comprises an aluminum alkoxide and an alcohol.

Embodiment P23

The method of embodiment P22, wherein the reducing agent comprises aluminium isopropoxide and isopropyl alcohol.

Embodiment P24

The method of any one of embodiments P1 to P23, wherein step (v) proceeds with greater than about 5:1, 6:1, 7:1, 8:1, 9:1, 10:1, 15:1, or 20:1 stereoselectivity.

Embodiment P25

An insulin peptide hormone covalently bonded to a compound of Formula (I), Formula (I-C), Formula (I-D), Formula (I-E), or Formula (I-F).

Embodiment P26

The insulin peptide hormone of embodiment P25, wherein the insulin peptide hormone is human insulin.

Embodiment P27

The insulin peptide hormone of embodiment P25 or P26, wherein lysine B29 of the insulin peptide hormone is covalently bonded to a compound of Formula (I), Formula (I-C), Formula (I-D), Formula (I-E), or Formula (I-F).

Embodiment P28

A pharmaceutical composition comprising the insulin peptide hormone of any one of embodiments P25 to P27 and a pharmaceutically acceptable excipient.

Embodiment P29

The pharmaceutical composition of embodiment P28, wherein said pharmaceutical composition is formulated for oral administration.

Embodiment P30

A method of treating or preventing diabetes comprising the administration of the peptide hormone of any one of embodiments P25 to P27, or the pharmaceutical composition of embodiment P28 or embodiment P29.

Embodiment P31

A compound having the following structure, (I-1)

or a pharmaceutically acceptable salt thereof. $L^1$ is —C(O)—, —C(O)O—, —C(O)NH—, or —CH$_2$—. $R^L$ is $L^2$-$R^{L2}$. $R^2$ is hydrogen or unsubstituted alkyl. $R^3$ is hydrogen, unsubstituted alkyl, or —OR$^{3A}$. $R^4$ is hydrogen, unsubstituted alkyl, or —OR$^{4A}$. $R^5$ is hydrogen, unsubstituted alkyl, or —OR$^{5A}$. $R^6$ is hydrogen, unsubstituted alkyl, or —OR$^{6A}$. $R^7$ is hydrogen, unsubstituted alkyl, or —OR$^{7A}$. $R^8$ is hydrogen, unsubstituted alkyl, or —OR$^{8A}$. $R^9$ is hydrogen, unsubstituted alkyl, or —OR$^{9A}$. $R^{10}$ is hydrogen, unsubstituted alkyl, or —OR$^{10A}$. $R^{11A}$ is hydrogen. $R^{11B}$ is an alcohol protecting group. $R^{12}$ is hydrogen, unsubstituted alkyl, or —OR$^{12A}$. $R^{13}$ is unsubstituted alkyl. $R^{1A}$, $R^{3A}$, $R^{4A}$, $R^{5A}$, $R^{6A}$, $R^{7A}$, $R^{8A}$, $R^{9A}$, $R^{10A}$, $R^{12A}$ and $R^{13A}$ are independently hydrogen, unsubstituted alkyl, or an alcohol protecting group. $L^2$ is a bond, —NR$^{L1}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^{L1}$ is hydrogen or unsubstituted alkyl. $R^{L2}$ is an amino acid of an insulin peptide hormone.

Embodiment P32

The compound of embodiment P31, wherein the compound has the structure, (I-F-1)

Embodiment P33

The compound of embodiment P31 or P32, wherein the insulin peptide hormone is human insulin.

Embodiment P34

The compound of any one of embodiments P31 to P33, where $R^{L2}$ is lysine B29 of the insulin peptide hormone.

Embodiment P35

A pharmaceutical composition comprising the insulin peptide hormone of any one of embodiments P31 to P34 and a pharmaceutically acceptable excipient.

Embodiment P36

The pharmaceutical composition of embodiment P35, wherein said pharmaceutical composition is formulated for oral administration.

Embodiment P37

A method of treating or preventing diabetes comprising the administration of the peptide hormone of any one of embodiments P31 to P34, or the pharmaceutical composition of embodiment P35 or embodiment P36.

Embodiment P38

A pharmaceutical composition comprising 6-α-ethyl-ursodeoxycholic acid (6-EUDCA) having the following structure,

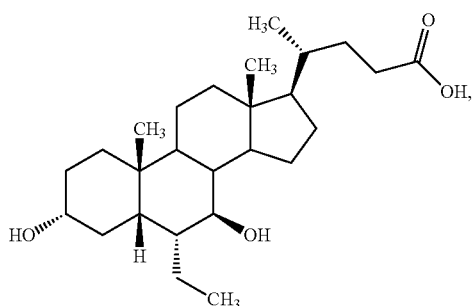
(I-F)

or a pharmaceutically acceptable salt thereof, and a pharmaceutically acceptable excipient.

Embodiment P39

A method of modulating farnesoid X receptor (FXR) activity, said method comprising contacting the farnesoid X receptor (FXR) with 6-α-ethyl-ursodeoxycholic acid (6-EUDCA) having the following structure,

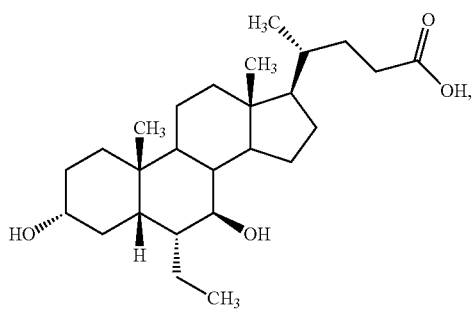
(I-F)

or a pharmaceutically acceptable salt thereof.

Embodiment P40

A method of treating a disorder or condition mediated by farnesoid X receptor (FXR) activity, said method comprising administering to a subject in need thereof an effective amount of 6-α-ethyl-ursodeoxycholic acid (6-EUDCA) having the following structure,

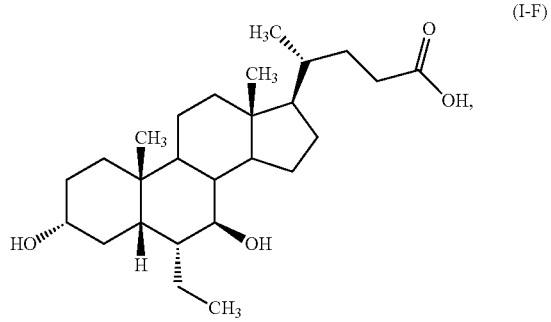 [SMILES: CC[C@H]1[C@H](O)C2C3CC[C@H]([C@H](C)CCC(=O)O)[C@@]3(C)CCC2[C@@]2(C)CC[C@@H](O)C[C@@H]12]
(I-F)

or a pharmaceutically acceptable salt thereof.

Embodiment P41

The method of embodiment P40, wherein said disorder or condition is cholestasis, diabetes, or liver disease.

Embodiment P42

The method of embodiment P40, wherein said disorder or condition is cholesterol gallstone disease (CGD).

Further embodiments contemplated herein include embodiments 1 to 43 following.

Embodiment 1

A method of synthesizing a compound having the following structure,

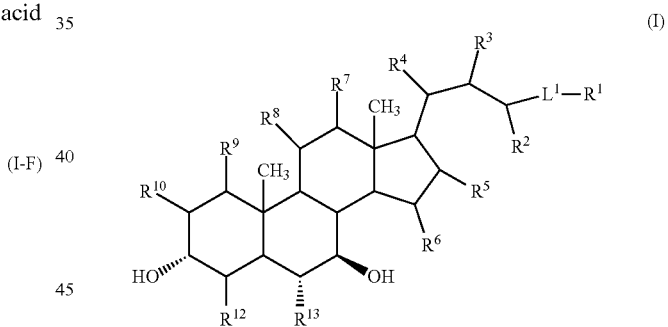
(I)

the method comprising,
(vii) contacting a compound of formula (II)

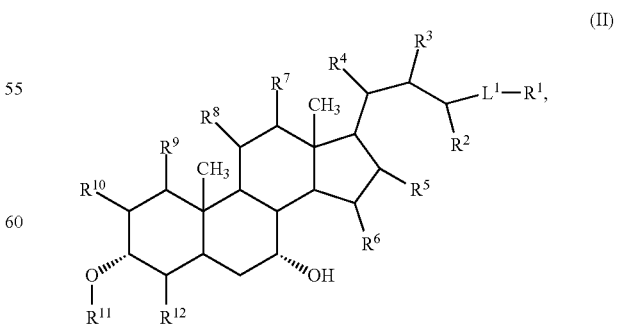
(II)

wherein $R^{11}$ is $R^{11A}$ or $R^{11B}$, with an oxidizing reagent to provide a compound of formula (III-A) or (III-B), (III-A)

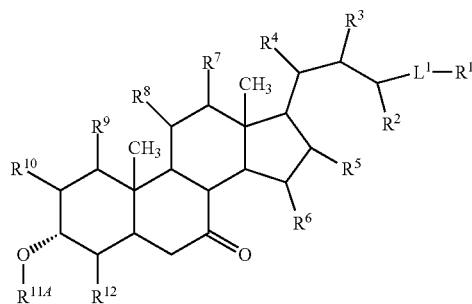

or (III-B)

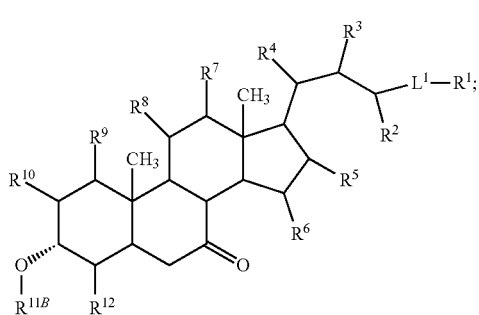

(viii) when the product of step (i) has a structure according to formula (III-A), contacting the compound of formula (III-A) with an alcohol protecting agent to provide a compound of formula (III-B);

(ix) contacting a compound of formula (III-B) with an alkylating agent in the presence of a sterically hindered base to provide a compound of formula (IV), (IV)

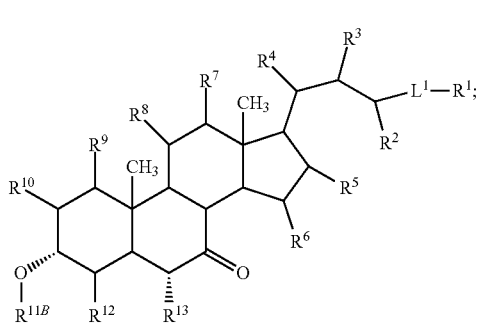

(x) optionally contacting the compound of formula (IV) with an alcohol deprotecting agent to provide a compound of formula (IV-A), (IV-A)

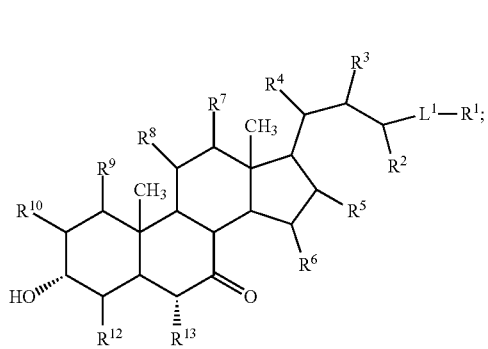

(xi) treatment of the compound of formula (IV) or (IV-A) with a reducing agent to provide a compound of formula (I) or (I-A), (I)

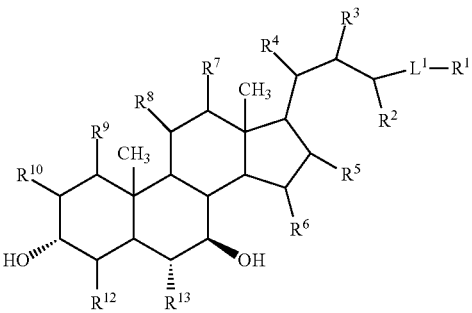

or (I-A)

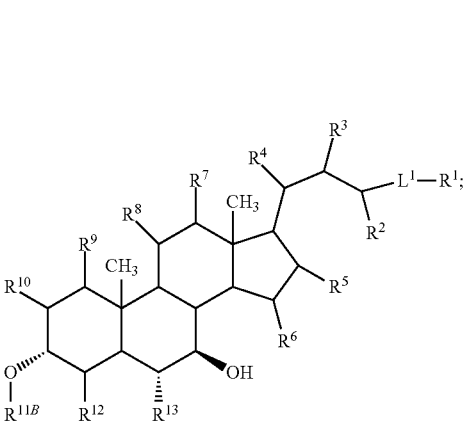

and (xii) when the product of step (v) has a structure according to formula (I-A), contacting the compound of formula with an alcohol deprotecting agent to provide a compound of formula (I-A).

$L^1$ is —C(O)—, —C(O)O—, —C(O)NH—, or —CH$_2$—. $R^1$ is hydrogen, halogen, —N$_3$, —CF$_3$, —CCl$_3$, —CBr$_3$, —CI$_3$, —CN, —CHO, —OR$^{1A}$, —NHR$^{1A}$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a carboxylate protecting group. $R^2$ is hydrogen or unsubstituted alkyl. $R^3$ is hydrogen, unsubstituted alkyl, or —OR$^{3A}$. $R^4$ is hydrogen, unsubstituted alkyl, or —OR$^{4A}$. $R^5$ is hydrogen, unsubstituted alkyl, or —OR$^{5A}$. $R^6$ is hydrogen, unsubstituted alkyl, or —OR$^{6A}$. $R^7$ is hydrogen, unsubstituted alkyl, or —OR$^{7A}$. $R^8$ is hydrogen, unsubstituted alkyl, or —OR$^{8A}$. $R^9$ is hydrogen, unsubstituted alkyl, or —OR$^{9A}$. $R^{10}$ is hydrogen, unsubstituted alkyl, or —OR$^{10A}$. $R^{11A}$ is hydrogen. $R^{11B}$ is an alcohol protecting group. $R^{12}$ is hydrogen, unsubstituted alkyl, or —OR$^{12A}$. $R^{13}$ is unsubstituted alkyl. $R^{1A}$, $R^{3A}$, $R^{4A}$, $R^{5A}$, $R^{6A}$, $R^{7A}$, $R^{8A}$, $R^{9A}$, $R^{10A}$, $R^{12A}$, and $R^{13A}$ are independently hydrogen, unsubstituted alkyl, or an alcohol protecting group.

Embodiment 2

The method of embodiment 1, the method comprising, (vi) contacting a compound of formula (II)

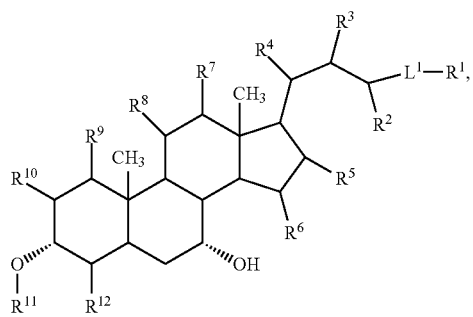

(II)

wherein $R^{11}$ is $R^{11A}$, with an oxidizing reagent to provide a compound of formula (III-A),

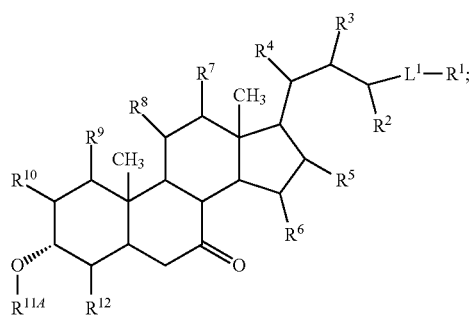

(III-A)

(vii) contacting the compound of formula (III-A) with an alcohol protecting agent to provide a compound of formula (III-B),

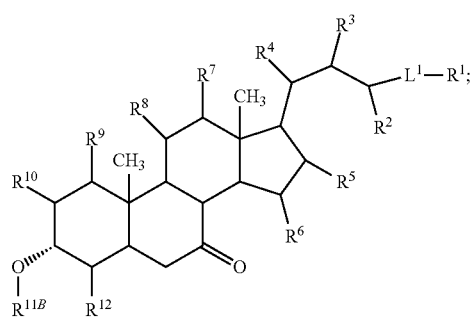

(III-B)

(viii) contacting a compound of formula (III-B) with an alkylating agent in the presence of a sterically hindered base to provide a compound of formula (IV),

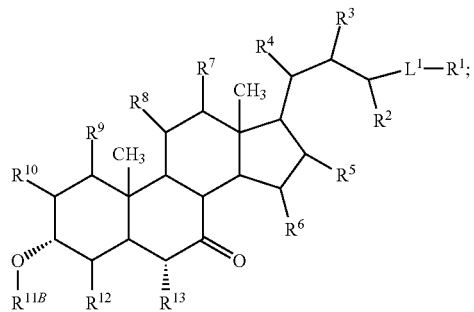

(IV)

(ix) contacting the compound of formula (IV) with an alcohol deprotecting agent to provide a compound of formula (IV-A),

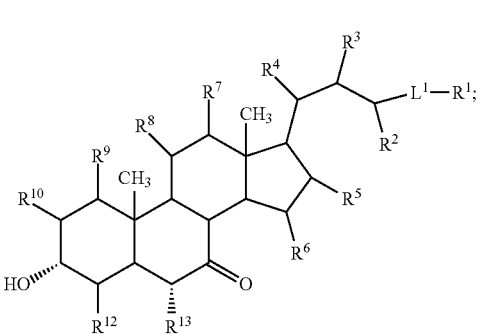

(IV-A)

(x) treatment of the compound of formula (IV-A) with a reducing agent to provide a compound of formula (I),

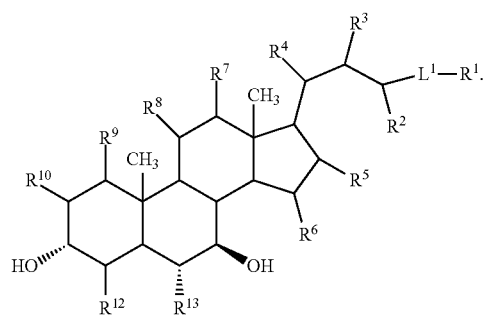

(I)

Embodiment 3

The method of embodiment 1 the method comprising, (ii) contacting a compound of formula (II)

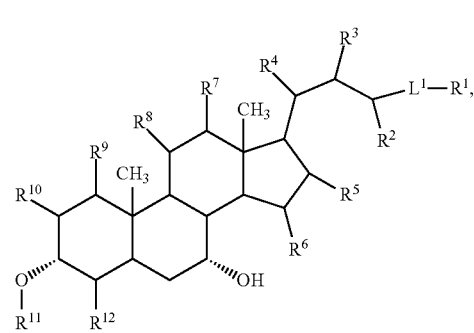

(II)

wherein R[11] is R[11B], with an oxidizing reagent to provide a compound of formula (III-B),

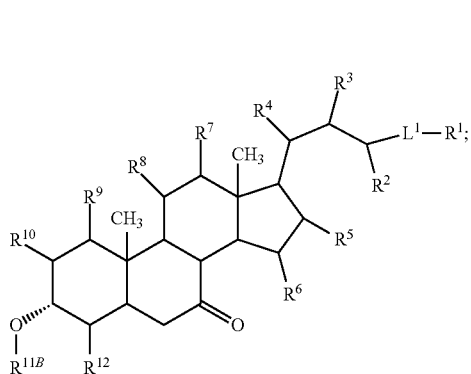

(III-B)

(v) contacting a compound of formula (III-B) with an alkylating agent in the presence of a sterically hindered base to provide a compound of formula (IV),

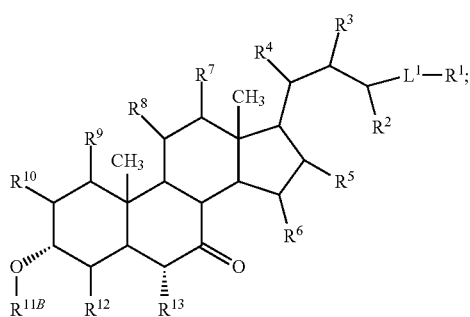

(IV)

(vi) contacting the compound of formula (IV) with an alcohol deprotecting agent to provide a compound of formula (IV-A),

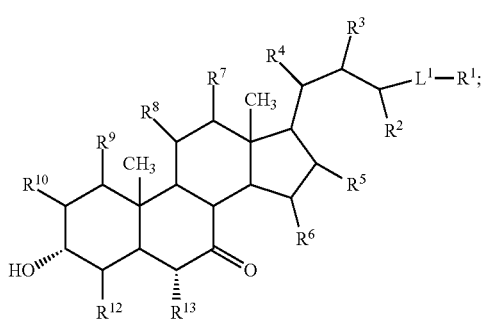

(IV-A)

(vii) treatment of the compound of formula (IV-A) with a reducing agent to provide a compound of formula (I)

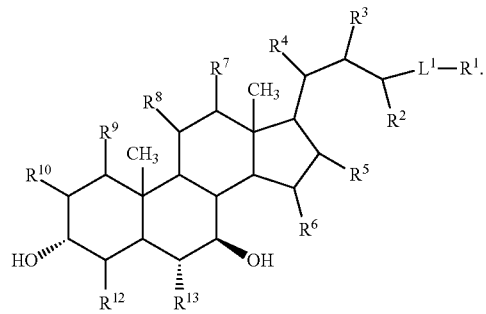

(I)

Embodiment 4

The method of embodiment 1, wherein R[11B] is substituted or unsubstituted alkyl, substituted or unsubstituted heteroalkyl, substituted or unsubstituted heterocycloalkyl, or —SiR[11C]R[11D]R[11E], wherein R[11C], R[11D], and R[11E] are independently substituted or unsubstituted alkyl or substituted or unsubstituted aryl.

Embodiment 5

The method of embodiment 4, wherein R[11B] is tetrahydropyranyl (THP).

Embodiment 6

The method of embodiment 1, wherein the compound of formula (I) has the following structure,

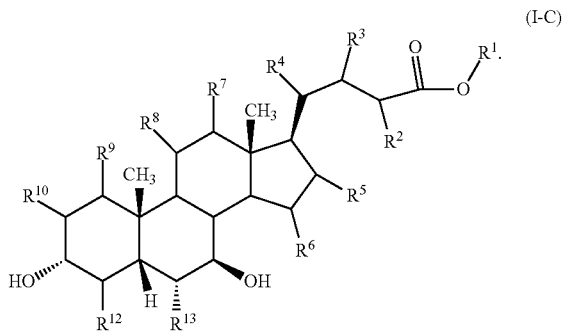

(I-C)

Embodiment 7

The method of embodiment 1, wherein the compound of formula (I) has the following structure,

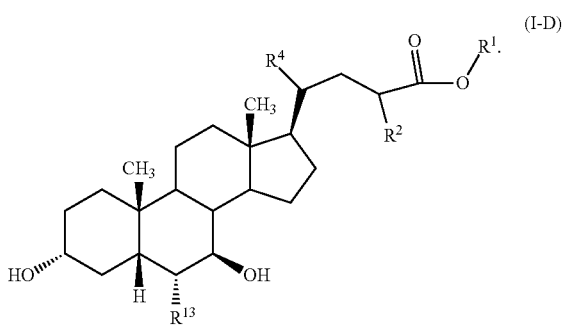

(I-D)

Embodiment 8

The method of embodiment 7, wherein
R$^1$ is hydrogen;
R$^2$ is hydrogen or unsubstituted alkyl; and
R$^4$ is hydrogen or unsubstituted alkyl.

Embodiment 9

The method of embodiment 1, wherein the compound of formula (I) has the following structure,

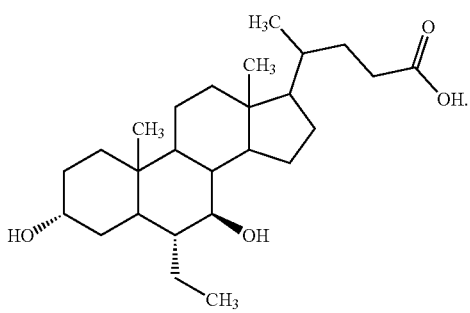

(I-E)

Embodiment 10

The method of embodiment 9 wherein the compound of formula (I) is 6-α-ethyl-ursodeoxycholic acid (6-EUDCA) having the following structure,

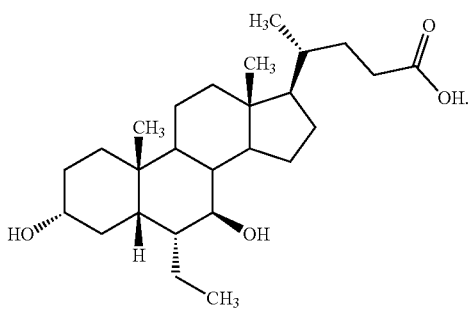

(I-F)

Embodiment 11

The method of embodiment 1, wherein the oxidizing reagent of step (a) is a chromium oxidant, a ruthenium oxidant, a manganese oxidant, an activated dimethylsulfoxide oxidant, or a hypervalent iodine oxidant.

Embodiment 12

The method of embodiment 11, wherein the oxidizing reagent is pyridinium chlorochromate (PCC).

Embodiment 13

The method of embodiment 1, wherein the alcohol oxidation proceeds with greater than about 5:1, 6:1, 7:1, 8:1, 9:1, or 10:1 regioselectivity.

Embodiment 14

The method of embodiment 1, wherein said sterically hindered base of step (iii) is lithium diisopropylamide (LDA), (M$^{+1}$)HMDS, (M$^{+1}$)tBuO, (M$^{+1}$)TMP, (M$^{+1}$)PhO, (M$^{+1}$)MeO, (M$^{+1}$)EtO, DBU, Dabco, N,N-dichlorohexylmethylamine, N,N-diisopropyl-2-ethylbutylamine, 2,6-di-tert-butyl-4-methylpyridine, pentamethylpiperidine, MTBD, PMDBD, TBD, or tri-tert-butylpyridine, wherein (M$^{+1}$) is Na, K, or Li.

Embodiment 15

The method of embodiment 14, wherein said sterically hindered base is lithium diisopropylamide (LDA).

Embodiment 16

The method of embodiment 1, wherein step (iii) comprises a second base.

Embodiment 17

The method of embodiment 16, wherein said base is an alkyllithium reagent.

Embodiment 18

The method of embodiment 1 wherein said alkylation agent of step (iii) is an alkyl halide.

Embodiment 19

The method of embodiment 18, wherein said alkylation agent is an alkyl iodide.

Embodiment 20

The method of embodiment 1, wherein step (iii) is performed in the presence of a polar aprotic solvent.

Embodiment 21

The method of embodiment 20, wherein said polar aprotic solvent is HMPA, HMPT, DMF, DMSO, MeCN, dioxane, methylpyrrolidone, DMPU, or a tetra-alkyl urea.

Embodiment 22

The method of embodiment 1, wherein the reducing agent of step (v) comprises an aluminum alkoxide and an alcohol.

Embodiment 23

The method of embodiment 22, wherein the reducing agent comprises aluminium isopropoxide and isopropyl alcohol.

Embodiment 24

The method of embodiment 1, wherein step (v) proceeds with greater than about 5:1, 6:1, 7:1, 8:1, 9:1, 10:1, 15:1, or 20:1 stereoselectivity.

Embodiment 25

An insulin peptide hormone covalently bonded to a compound of Formula (I), Formula (I-C), Formula (I-D), Formula (I-E), or Formula (I-F).

Embodiment 26

The insulin peptide hormone of embodiment 25, wherein the insulin peptide hormone is human insulin.

Embodiment 27

The insulin peptide hormone of embodiment 25, wherein lysine B29 of the insulin peptide hormone is covalently bonded to a compound of Formula (I), Formula (I-C), Formula (I-D), Formula (I-E), or Formula (I-F).

Embodiment 28

A pharmaceutical composition comprising the insulin peptide hormone of embodiment 25 and a pharmaceutically acceptable excipient.

Embodiment 29

The pharmaceutical composition of embodiment 28, wherein said pharmaceutical composition is formulated for oral administration.

Embodiment 30

A method of treating or preventing diabetes comprising the administration of the peptide hormone of embodiment 25.

Embodiment 31

A compound having the following structure,

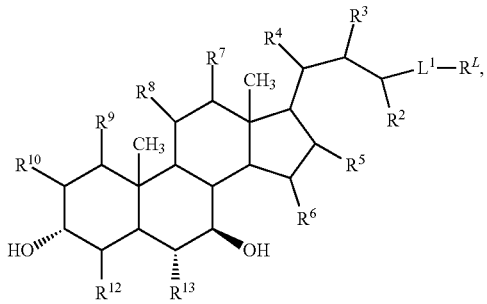

(I-1)

or a pharmaceutically acceptable salt thereof. $L^1$ is —C(O)—, —C(O)O—, —C(O)NH—, or —CH$_2$—. $R^L$ is $L^2$-$R^{L2}$. $R^2$ is hydrogen or unsubstituted alkyl. $R^3$ is hydrogen, unsubstituted alkyl, or —OR$^{3A}$. $R^4$ is hydrogen, unsubstituted alkyl, or —OR$^{4A}$. $R^5$ is hydrogen, unsubstituted alkyl, or —OR$^{5A}$. $R^6$ is hydrogen, unsubstituted alkyl, or —OR$^{6A}$. $R^7$ is hydrogen, unsubstituted alkyl, or —OR$^{7A}$. $R^8$ is hydrogen, unsubstituted alkyl, or —OR$^{8A}$. $R^9$ is hydrogen, unsubstituted alkyl, or —OR$^{9A}$. $R^{10}$ is hydrogen, unsubstituted alkyl, or —OR$^{10A}$. $R^{11A}$ is hydrogen. $R^{11B}$ is an alcohol protecting group. $R^{12}$ is hydrogen, unsubstituted alkyl, or —OR$^{12A}$. $R^3$ is unsubstituted alkyl. $R^{1A}$, $R^{3A}$, $R^{4A}$, $R^{5A}$, $R^{6A}$, $R^{7A}$, $R^{8A}$, $R^{9A}$, $R^{10A}$, $R^{12A}$ and $R^{13A}$ are independently hydrogen, unsubstituted alkyl, or an alcohol protecting group. $L^2$ is a bond, —NR$^{L1}$—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^{L1}$ is hydrogen or unsubstituted alkyl. $R^{L2}$ is an amino acid of an insulin peptide hormone.

Embodiment 32

The compound of embodiment 31 wherein the compound has the structure,

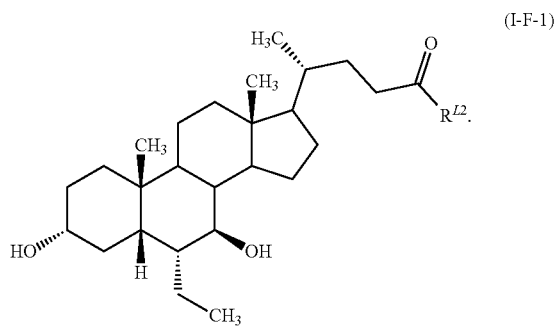

(I-F-1)

Embodiment 33

The compound of embodiment 31, wherein the insulin peptide hormone is human insulin.

Embodiment 34

The compound of embodiment 31, where $R^{L2}$ is lysine B29 of the insulin peptide hormone.

Embodiment 35

A pharmaceutical composition comprising the insulin peptide hormone of embodiment 31 and a pharmaceutically acceptable excipient.

Embodiment 36

The pharmaceutical composition of embodiment 35, wherein said pharmaceutical composition is formulated for oral administration.

Embodiment 37

A method of treating or preventing diabetes comprising the administration of the peptide hormone of embodiment 31.

Embodiment 38

A pharmaceutical composition comprising 6-α-ethyl-ursodeoxycholic acid (6-EUDCA) having the following structure,

63

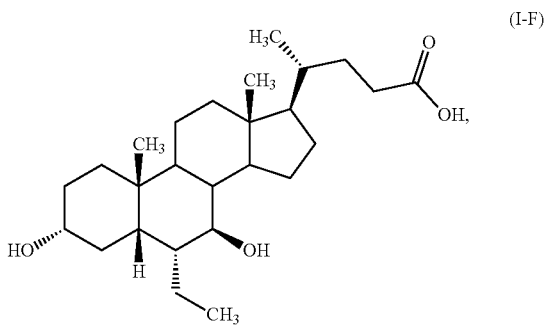 [SMILES: CC[C@H]1[C@H](O)C2C3CC[C@H]([C@H](C)CCC(=O)O)[C@@]3(C)CCC2[C@@]2(C)CC[C@@H](O)C[C@@H]12]

or a pharmaceutically acceptable salt thereof, and a pharmaceutically acceptable excipient.

Embodiment 39

A method of modulating farnesoid X receptor (FXR) activity, said method comprising contacting the farnesoid X receptor (FXR) with 6-α-ethyl-ursodeoxycholic acid (6-EUDCA) having the following structure,

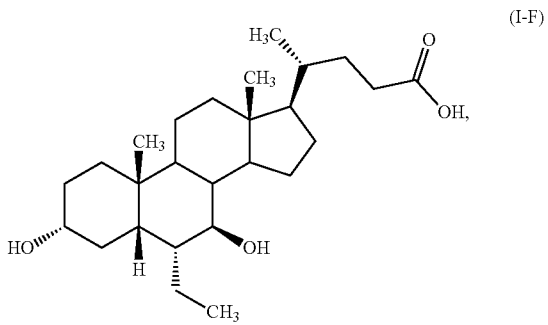 [SMILES: CC[C@H]1[C@H](O)C2C3CC[C@H]([C@H](C)CCC(=O)O)[C@@]3(C)CCC2[C@@]2(C)CC[C@@H](O)C[C@@H]12]

or a pharmaceutically acceptable salt thereof.

Embodiment 40

A method of treating a disorder or condition mediated by farnesoid X receptor (FXR) activity, said method comprising administering to a subject in need thereof an effective amount of 6-α-ethyl-ursodeoxycholic acid (6-EUDCA) having the following structure,

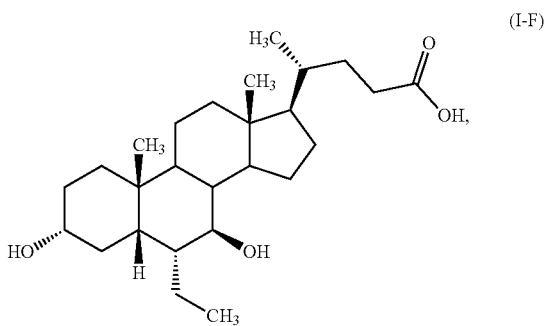 [SMILES: CC[C@H]1[C@H](O)C2C3CC[C@H]([C@H](C)CCC(=O)O)[C@@]3(C)CCC2[C@@]2(C)CC[C@@H](O)C[C@@H]12]

or a pharmaceutically acceptable salt thereof.

64

Embodiment 41

The method of embodiment 40, wherein said disorder or condition is cholestasis, diabetes, or liver disease.

Embodiment 42

The method of embodiment 41, wherein the liver disease is nonalcoholic steatohepatitis (NASH).

Embodiment 43

The method of embodiment 40, wherein said disorder or condition is cholesterol gallstone disease (CGD).

III. Examples

Abbreviations Used

FXR, Farnesoid X Receptor;
CDCA, chenodeoxycholic acid;
UDCA, Ursodeoxycholic acid;
6EUDCA, 6-αethyl-ursodeoxycholic acid;
qPCR, quantitative polymerase chain reaction;
TGR5, G-protein-coupled receptor.

General Procedures:

Organic reagents were purchased from commercial suppliers unless otherwise noted and were used without further purification. All solvents were analytical or reagent grade. All reactions were carried out in flame-dried glassware under argon or nitrogen. Melting points were determined and reported automatically by an optoelectronic sensor in open capillary tubes and were uncorrected. $^1$H NMR and $^{13}$C NMR spectra were measured at 500 MHz and 125 MHz respectively, and using $CDCl_3$ or $CD_3OD$ as the solvents and tetramethylsilane ($Me_4Si$) as the internal standard. Flash column chromatography was performed using Sigma-Aldrich silica gel 60 (200-400 mesh), carried out under moderate pressure by using columns of an appropriate size packed and eluted with appropriate eluents. Silica gel chromatography was performed on a Biotage flash column gradient pump system using 15 cm long columns. All reactions were monitored by TLC on precoated plates (silica gel HLF). TLC spots were visualized either by exposure to iodine vapors or by irradiation with UV light. Organic solvents were removed in vacuum by rotary evaporator. Elemental analyses were performed by Columbia Analytical Services, Inc. Tucson, Ariz.

Synthesis

3α-Hydroxy-7-keto-5β-cholan-24-oic acid (1)

To a suspension of chenodeoxycholic acid (CDCA, 1.0 g, 2.5 mmol) and silica gel (4 g, 200-400 mesh, Aldrich) in anhydrous $CHCl_3$ (2 mL) was added, portionwise, pyridinium chlorochromate (PCC, 0.81 g, 38 mmol) in 25 mL of $CH_2Cl_2$ and the reaction mixture was stirred at room temperature for 15-20 min. The mixture was filtered and the filtrate was washed with water (20 mL) and brine (20 mL). The organic layer was dried over $Na_2SO_4$ and concentrated. The resulting crude oil was purified by flash column chromatography ($CH_2Cl_2$: MeOH 95:5) to afford 1 as a solid (0.76 g, 78% yield), mp 201.2 OC (lit.[22] mp 201.1° C.). $^1$H NMR (500 MHz, $CD_3OD$) δ 3.51 (m, 1H), 2.94 (m, 1H), 2.52 (t, 1H), 2.30 (m, 2H), 2.19 (m, 6H), 1.70 (m, 2H), 1.43 (m, 4H), 1.31 (m, 6H), 1.19 (s, 3H), 1.12 (m, 4H), 0.92 (d, 3H), 0.66 (s, 3H). $^{13}$C NMR (125 MHz, CD$_3$OD) δ 212.7, 176.8, 70.1, 54.8, 49.2, 48.9, 47.7, 46.0, 44.9, 43.0, 42.4, 38.9, 36.8, 35.1, 34.9, 33.7, 31.0, 30.6, 29.2, 27.8, 24.3, 22.0, 21.4, 17.3, 10.7. Anal. Calcd for C$_{24}$H$_{38}$O$_4$: C, 73.81; H, 9.81. Found: C, 73.50; H, 9.63.

3α-Tetrahydropyranyloxy-7-keto-5β-cholan-24-oic acid (2)

To a solution of 1 (0.50 g, 1.3 mmol) in 16 mL of CHCl$_3$:Cl$_2$CH$_2$:Et$_2$O (1:1:2) were added p-toluensulfonic acid (0.06 g, 0.3 mmol) and 3,4-dihydro-2H-pyrane (0.41 g, 4.9 mmol). The reaction mixture was stirred at room temperature for 60 min. Water (20 mL) was added and the mixture was extracted with EtOAc (3×30 ml); the combined organic layers were washed with brine, dried over Na$_2$SO$_4$, and concentrated. The resulting crude oil was purified by flash column chromatography (CH$_2$Cl$_2$:Et$_2$O 1:2) to afford 2 as a white solid (0.47 g, 76% yield), mp 160.8° C. (lit.[26] mp 157-159° C.). Selected $^1$H NMR (600 MHz, CDCl$_3$) δ 4.73 (d, 1H), 3.86 (m, 1H), 3.59 (m, 1H), 3.46 (m, 1H), 2.82 (m, 1H), 1.17 (s, 3H), 0.92 (d, 3H), 0.63 (s, 3H). $^{13}$C NMR (125 MHz, CDCl$_3$) δ 212.3, 179.8, 96.4, 62.8, 62.1, 19.8, 18.1, 11.4. Anal. Calcd for C$_{29}$H$_{46}$O$_5$: C, 73.38; H, 9.77. Found: C, 73.30; H, 9.76.

3α-Hydroxy-6α-ethyl-7-keto-5β-cholan-24-oic acid (3)

To a solution of 2 (0.30 g, 0.63 mmol) in dry THF (20 mL) at −78° C. were added dropwise n-butyllithium (1.0 mL, 1.6 M solution in hexane, 1.6 mmol), HMPA (0.7 g, 4 mmoL) and LDA (2.0 mL, 1.8 M in THF/heptane/ethylbenzene, 3.6 mmol). The reaction mixture was stirred for 30 min. Iodoethane (2.0 g, 13 mmol) was slowly added and the reaction mixture was allowed to warm overnight to room temperature. After rotary evaporation, water and ether were added and the aqueous layer was acidified with 10% HCl and extracted with EtOAc (5×20 mL). The organic layers were washed with brine, dried over Na$_2$SO$_4$, and concentrated to give a yellow oil. After a short column (CH$_2$Cl$_2$:Et$_2$O 1:2), the crude semi-solid was dissolved in ethanol (5 mL) and pyridinium p-toluenesulfonate (15 mg, 0.06 mmol) was added. The reaction mixture was stirred at 55° C. for 4 h. After rotary evaporation, the product was passed through a short column (CH$_2$Cl$_2$:Et$_2$O 1:2) to obtain 3 as a semi-solid (0.08 g, 30%) that was used in the next step without further purification.

General Method for Meerwein-Ponndorf-Verley (MPV) Type Reduction

To a solution of aluminum foil (30 eq.) in anhydrous isopropanol (80 eq.) was added mercuric chloride (0.15 eq.). The reaction mixture was warmed up to reflux for 9-12 hours under an atmosphere of nitrogen until aluminum foil was completely dissolving into isopropanol. After the isopropoxide aluminum formed, it was used directly for the reduction of 3α-hydroxy-7-keto-5β-cholan-24-oic acid (1) and 3α-hydroxy-6α-ethyl-7-keto-5β-cholan-24-oic acid (3). To this solution, 7-keto analog (1 eq.) was added and the reaction mixture was heated to reflux for 3-5 hours under N$_2$ and checked by TLC. After cooling, the reaction mixture was dissolved in EtOAc (25 mL) and water was added (30 mL), the solution was acidified to pH 2 with 2N hydrochloric acid, and then extracted with EtOAc (3×25 mL). The combined organic layers were washed with water and brine, dried (Na$_2$SO$_4$), and evaporated under vacuum.

Usodeoxycholic acid (UDCA): yield: 82%. Crystallization by EtOAc: pet ether 1:1 gave a white crystal, mp 202.5° C. (203-204° C. (lit. Sigma)). Selected $^1$H NMR (600 MHz, CD$_3$OD) δ 3.49 (brs, 2H), 2.37 (m, 1H), 2.22 (m, 1H), 1.93 (m, 2H), 1.87 (m, 3H), 0.97 (s, 3H), 0.96 (d, 3H), 0.71 (s, 3H). $^{13}$C NMR (125 MHz, CD$_3$OD) δ 176.7, 70.7, 70.5, 56.1, 55.1, 20.9, 17.5, 11.0. Anal. Calcd for C$_{24}$H$_{40}$O$_4$: C, 73.43; H, 10.27. Found: C, 73.29; H, 9.94.

3α, 7β-Dihydroxy-6α-ethyl-5β-cholan-24-oic acid (6EUDCA): yield: 80%. Solidification by MeOH/CH$_2$Cl$_2$/pet ether gave a beige powder, mp 109.5° C. Selected $^1$H NMR (600 MHz, CDCl3): δ 3.50 (m, 1H), 3.36 (m, 1H), 2.25 (m, 1H), 2.15 (m, 1H), 0.91 (d, 3H), 0.88 (s, 3H), 0.77 (t, 3H), 0.64 (s, 3H). $^{13}$C NMR (125 MHz, CDCl3): δ 178.4, 75.2, 71.9, 55.8, 54.8, 43.7, 42.8, 41.2, 40.2, 39.6, 35.5, 34.4, 30.8, 30.7, 30.5, 28.3, 27.0, 23.5, 21.4, 20.8, 18.3, 12.0, 11.8. Anal. Calcd for C$_{26}$H$_{44}$O$_4$: C, 74.24; H, 10.54. Found: C, 74.00; H, 10.01.

Biology

Antibodies

Antibodies pAKT S473, pGSK3beta, total AKT and total GSK3beta used in the study for western blot analysis were obtained from Cell signaling (USA).

Cell Culture

HepG2 cells were purchased from American Type Culture Collection. The cells were cultured in Minimal Essential Medium (MEM) (Cellgro, Manassas, Va.) supplemented with 100 u/ml penicillin/streptomycin sulfate (Mediatech, Herndon, Va.) and 10% (v/v) heat-inactivated fetal boine serum (Irvine scientific, Santa Ana, Calif.). Primary hepatocytes were isolated from mouse liver tissues and cultured in Dulbecco's modified Eagle medium and F-12 (Cellgro, Manassas, Va.) supplemented with 100 U/ml penicillin G/streptomycin and 10% (v/v) heat-inactivated fetal bovine serum. Cells were cultured in insulin or serum free media for 16 hr before performing all experiments unless otherwise mentioned. Primary mouse hepatocytes were isolated as described from C57BL6/J mice by using collagenase type IV; 5×10$^5$ cells per well were plated in six-well collagen-coated plates and cultured in DMEM/Ham's F12 media.[32]

TR-FRET Assay

To assess the binding of UDCA and 6EUDCA we performed TR-FRET assay using DY246 as an hFXR fluorescent probe as described earlier (Reference 29). For this assay 30 nl of 10 mM testing chemical was transferred with a pintool into 15 μL of a mixture of GST-hFXR and Tb-anti-GST in a 384-well black plate, and then 5 μL of 40 nM DY246 was dispensed to give a final volume of 20 μL/well with 10 nM GST-hFXR, 1.5 nM Tb-anti-GST, UDCA (1000 μM, 300 μM or 100 μM) or 6EUDCA (100 μM, 30 μM or 10 μM) and 10 nM DY246. In addition, selected wells containing 5 μM GW4064 or DMSO were used as positive and negative controls, respectively. The final DMSO concentration was 0.23% in all wells. The plates were then spun down after a brief shake and incubated for either 15 or 25 min at room temperature. The TR-FRET signal was then collected for each well with an Envison plate reader using an excitation wavelength of 340 nm and emission wavelengths of 520 nm and 490 nm.

RNA Isolation and Quantitative Real-Time PCR

RNA was isolation, reverse transcription reactions and real time PCR were performed as described previously (Reference 33). SHP primers forward 5'-GCC CTG CAC TCT CGC TTT CT-3'; reverse 5'-CAA CTG GGC ACC GAG GCA ACA GTT G-3' were used to amplify using Sybr green master mix purchased from applied biosystems (Foster City, Calif.). Amplification of 36b4 with specific primers forward 5'-TGG AGT CTT TCT GGA GCC TT-3'; reverse 5'-TCC TGT TGC AGG TGT GCG AT-3' was used as internal control. Absolute mRNA expression was quantified using standard curve method. All primers used were Sybr green based synthesized by IDT. Sybr green was purchased from applied biosystems (Foster City, Calif.). Amplification of 36b4 was used as internal control. Absolute mRNA expression was quantified using standard curve method.

Western Blot Analysis

Western blot analysis was performed according to the methods described earlier (Reference 34). Different antibodies used in the study are mentioned in the methodology section. Briefly, serum starved HepG2 cells or mouse primary hepatocytes from flox/flox or fxr−/− mice cultured in collagen coated 6-well culture dishes were used to make total cell lysates. Proteins were resolved on SDS-PAGE gels and transferred on to nitrocellulose membrane and blotted with antibodies against phosphor AKT (S473) and pGSK3beta. The signal with secondary antibody was detected with either Odyssey 3.0 infrared scanner or ECL chemiluminiscence.

Example 1

To identify potent and high affinity FXR modulators that can act as targeted therapeutic agents, we designed and synthesized 6-αethyl-ursodeoxycholic acid (6EUDCA), an α-ethylated derivative of UDCA and identified 6EUDCA binds FXR better than UDCA via a non-genomic pathway.

6EUDCA is a novel derivative of CDCA whose preparation was reported in a 2011 patent (Reference 15). However that synthesis methodology was complicated, resulted in a low yield. We have previously provided proof-of-principle that 6EUDCA and other derivatives of UDCA can activate TGR5 (Reference 11), a G-protein-coupled bile acid receptor mediating cellular responses to bile acids.

We have converted the 6ECDCA to 6EUDCA by a stereoselective pathway. In this report, our initial chemistry focuses on the conversion of the readily-available starting material CDCA to the 6EUDCA by an improved and highly stereoselective cost-effective synthesis.

To convert CDCA to 6EUDCA smoothly, we first evaluated the synthetic procedures of UDCA. The existing methodologies for synthetic UDCA start from the major component of bile acids, cholic acid (CA) (Reference 16). In 1954, Kanajawa reported the first synthetic method for the preparation of UDCA from CA in 7-steps (<9% yield; Reference 17). This procedure is still used for the industrial production of UDCA. Several similar synthetic methods starting from CA, including the radical reduction in the last step with an alkaline metal (Na or K) in refluxing alcohol, have been reported recently (References 18-20). However, it is difficult to control these vigorous reaction conditions, and the use of concentrated metal bases under high pressure and temperature can easily lead to explosions.

With this in mind, several modifications have been reported. In 1980, Faba reported a UDCA synthesis that begins with CA. CA was converted to a methyl ester intermediate and oxidized by Jones reagent with the final step using Zn-EtOH to reduce 7-keto to get UDCA (Reference 21). In 1982, Iida and Chang reported an improved synthetic method that described the four possible 3, 7-dihydroxy acids (Reference 22). This strategy involved a key step for reducing 12-oxo tosylhydrazones. In addition, in 1981, Calzda reported a 6-step synthesis for producing UDCA starting from CA (Reference 23); this method employed aluminum alkoxide (Al(OiPr)$_3$/iPrOH) instead of alkaline metal in the final reduction step (29% yield). However, these procedures for producing UDCA and its analogs are long, costly, and complicated. Previously, we developed an improved synthetic route for large scale production of 6ECDCA, which is an epimer of 6EUDCA, using the cost-effective and readily-available starting material CDCA.[24] We noted the possibility of using a similar strategy for the synthesis of UDCA and its derivative 6EUDCA.

An improved facile synthesis of UDCA from the readily available starting material CDCA (FIG. 2) was achieved which resulted in about 60-64% overall yield. CDCA was converted to the derivative 1 according to our previously reported synthetic approach (Reference 24). In this synthetic step, the desired corresponding intermediate 1 from CDCA with pyridinium chlorochromate (PCC) was obtained in 82% yield, which is a partially regioselective oxidation. Thus, the selective installation of carbonyl functionality in the 7-position of CDCA is well done. In contrast to the current work, earlier work included a partial oxidation of CDCA (Reference 25), a laborious potassium chromate procedure,[19] and a modified synthetic route via CA (Reference 26). These methods were complicated and restricted, clearly suggesting the current regioselective oxidation methodology we improved is facile to carry out for the large scale production of UDCA.

UDCA and CDCA differ in the orientation of the hydroxyl group at the C7 position. In UDCA the hydroxyl is oriented equatorially (7β-OH), and in CDCA the hydroxyl is oriented axially (7α-OH). Intermediate 1 in FIG. 2 was converted smoothly to UDCA by Meerwein-Ponndorf-Verley (MPV) type reduction (Reference 27). In particular, by modification of published methods (Reference 11), the intermediate 1 was then reduced stereoselectively by Al-catalytic reduction with aluminum alkoxide (Al(OiPr)$_3$/iPrOH), giving the expected product UDCA with an 82% yield. Therefore, UDCA has been successfully synthesized in 2 steps from CDCA by an improved stereoselective procedure in 60-64% overall yield.

Figure 2:
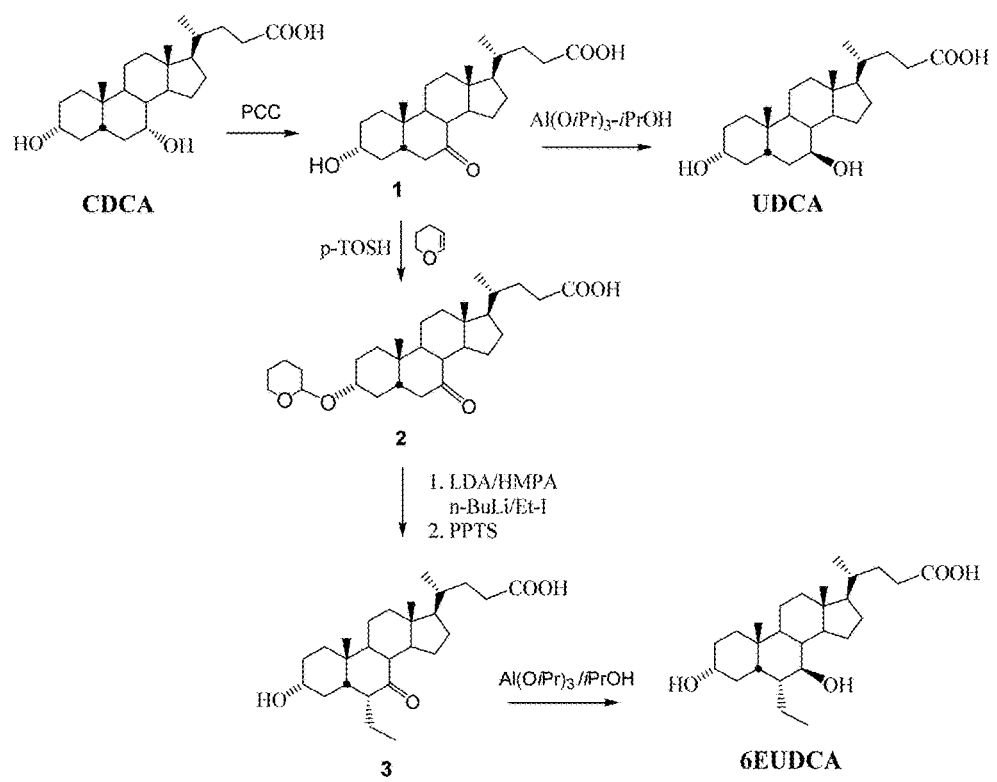
FIG. 2 shows a highly stereoselective synthesis of UDCA and 6EUDCA from CDCA.
Figure 3A:
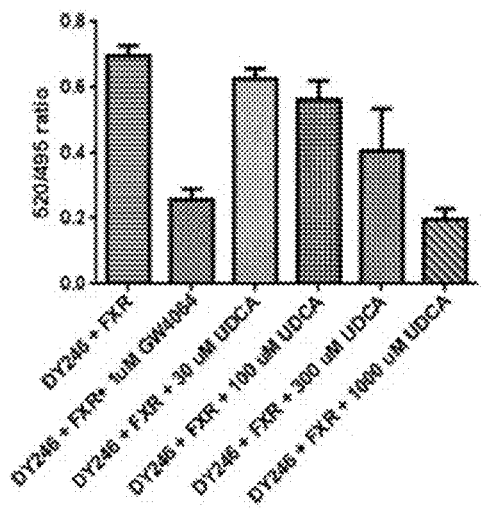
FIGS. 3A-3D show binding of UDCA and 6EUDCA to FXR in a TR-FRET assay. UDCA binds to FXR as indicated by the reduction in fluorescence signal of DY246 (Reference 30) at different time points (15 min and 25 min) with high concentrations (FIG. 3A and FIG. 3B). 6EUDCA binds strongly to FXR at concentrations as low as 10M, as indicated by reduced fluorescence signal of DY246 (FIG. 3C and FIG. 3D).
Figure 3B:
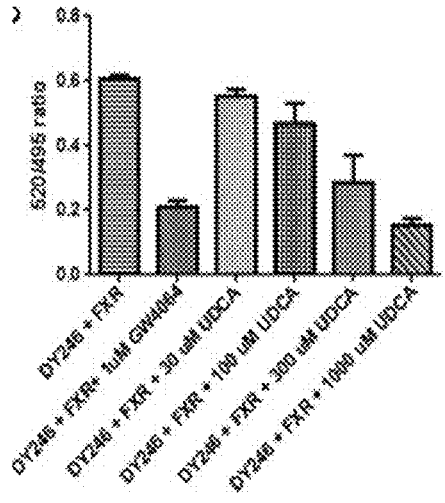
Figure 3C:
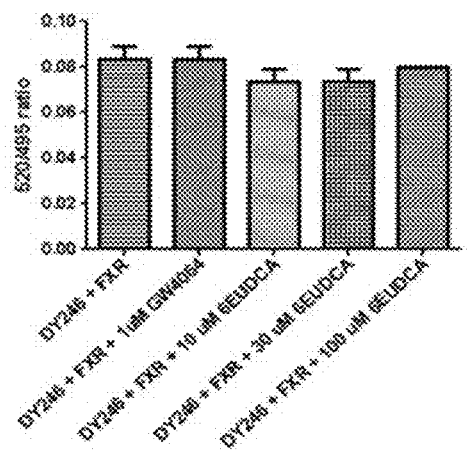
Figure 3D:
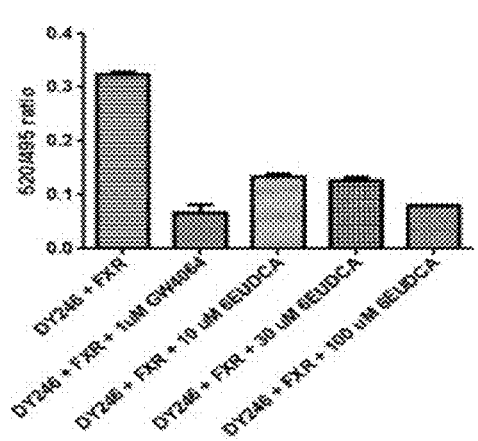

Prompted by production of UDCA from CDCA, we directed our efforts to the synthesis of 6EUDCA from CDCA, The synthesis of the protected 3-hydroxyl of 2 started with the previously reported 6ECDCA preparation (Reference 24). The critical steps in the synthesis of UDCA and 6EUDCA employ selective oxidation of CDCA and MPV reduction (Reference 27). In initial experiments, we examined the MPV reduction of compound 3 (Reference 28) which was reduced stereoselectively by reaction with aluminum alkoxide (Al(OiPr)$_3$/iPrOH) to afford 6EUDCA. The reaction scheme from CDCA to 6EUDCA occurs over 4 steps with a 15% overall yield (FIG. 2).

The determination of the C7 stereochemistry of 6EUDCA was made by $^1$H NMR using CD$_3$OD or CDCl$_3$ as a solvent. 6EUDCA and 6ECDCA are epimers, differing only in the configuration of the chiral carbon at C7 (Reference 29). The C3 and C7 methine proton peaks of 6EUDCA are easily identified.

Next we compared the biding affinities of synthesized 6EUDCA and UDCA to FXR using a time-resolved fluorescence resonance energy transfer binding assay (TR-FRET). Positive and negative controls are described in the Supporting Information. Both UDCA and 6EUDCA bind to FXR; however, UDCA binds FXR with a very low affinity and only at high concentrations. In contrast 6EUDCA binds FXR with higher affinity as indicated by the low concentrations of ligand that still produce signals in the TR-FRET assay (FIG. 3). Apparently, 6EUDCA is more potent in binding and activating FXR with greatly increased potency relative to UDCA. DY246 was chosen as a positive control in the TR-FRET assay because it is a derivative of GW4064, which is a potent FXR agonist. In addition, DY246 is a potent FXR agonist itself with an $EC_{50}$ of 550 nM and has successfully been used as a fluorescent probe in a high throughput screening campaign to identify FXR antagonists (Reference 30). These data suggest that 6EUDCA may be a better therapeutic ligand for FXR as compared to UDCA.

Figure 4:
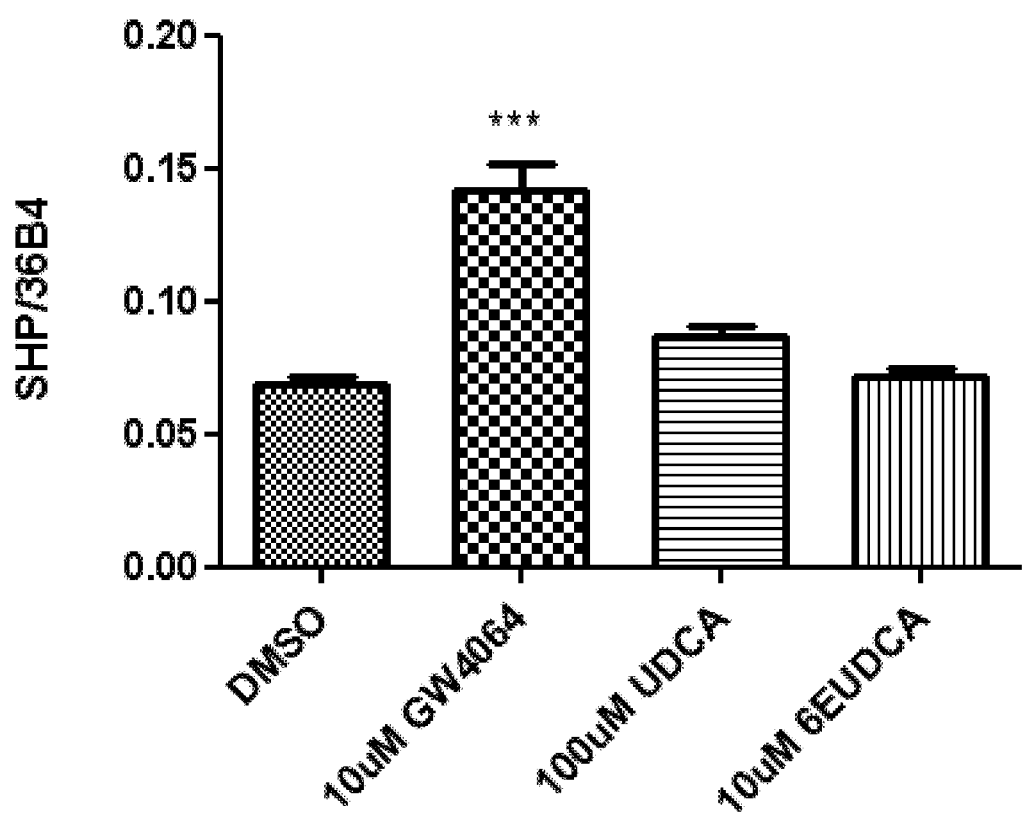
FIG. 4 shows the QPCR analysis of the FXR target gene SHP in liver cells.

Next, we investigated the biological effects of UDCA and 6EUDCA on the human liver cell line HepG2 and on primary mouse hepatocytes. Initially we tested whether UDCA or 6EUDCA could affect FXR in HepG2 cells. Our qPCR data indicate that neither UDCA nor 6EUDCA could induce the FXR target gene SHP (FIG. 4). GW4064, a known agonist of FXR, was used as a positive control in all our experiments (Reference 31). Serum starved HepG2 cells were treated either with DMSO, 10 M GW4046, 100 μM UDCA, or 10 M 6EUDCA overnight. Changes in the expression of SHP gene were analyzed and normalized with the internal standard 36b4. Data are presented as mean±S.D. ANOVA and Dunnett's multiple comparison tests were applied to determine the significance of the differences between DMSO and FXR ligands. Asterisks (***) indicate a significant difference in SHP expression (p<0.0001) compared to DMSO.

Figure 5A:
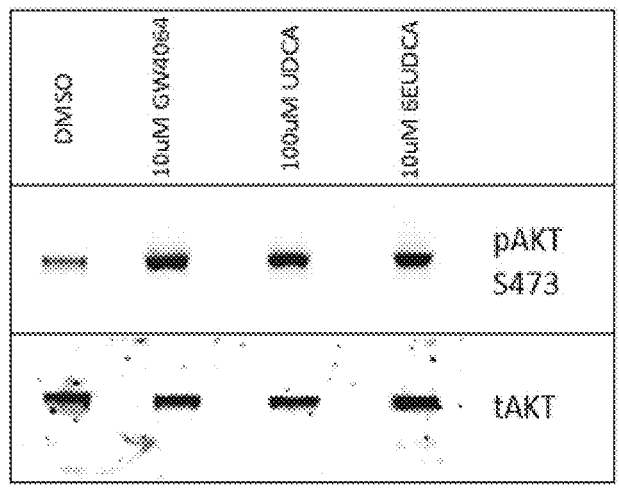
FIGS. 5A-5B show that UDCA and 6EUDCA can induce phosphorylation of AKT in liver cells.
Figure 5B:
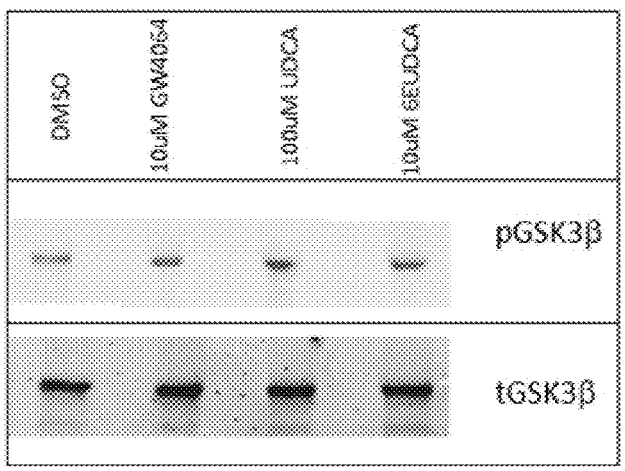

The UDCA result is consistent with previous literature suggesting that UDCA is not an agonist for FXR. Subsequently, based on previous studies in our laboratory we tested the effect of UDCA and 6EUDCA on AKT and its downstream target GSK3beta. Serum starved HepG2 cells were treated with or without UDCA or 6EUDCA for 10 min. Cell extracts were used to separate proteins by SDS-PAGE, and Western blot analysis was performed using specific antibodies against phosphorylated AKT and phosphorylated GSK3beta. Serum-starved HepG2 cell extracts were prepared after incubation with DMSO, GW4064, UDCA, or 6EUDCA for 10 min. Extracts were analyzed by Western blot using specific antibodies against pAKT S473 (left panel) or pGSK3beta (right panel). Both UDCA and 6EUDCA were effective in inducing AKT phosphorylation in HepG2 cells (FIG. 5).

Figure 6A:
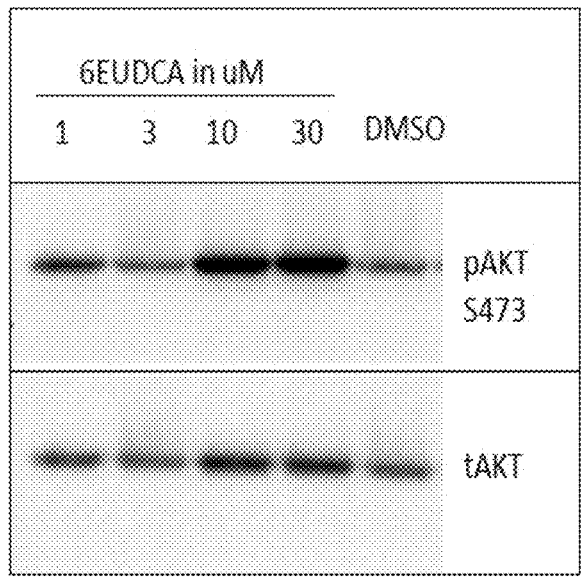
FIGS. 6A-6B show that induction of phosphorylation of AKT by 6EUDCA is concentration dependent in liver cells.
Figure 6B:
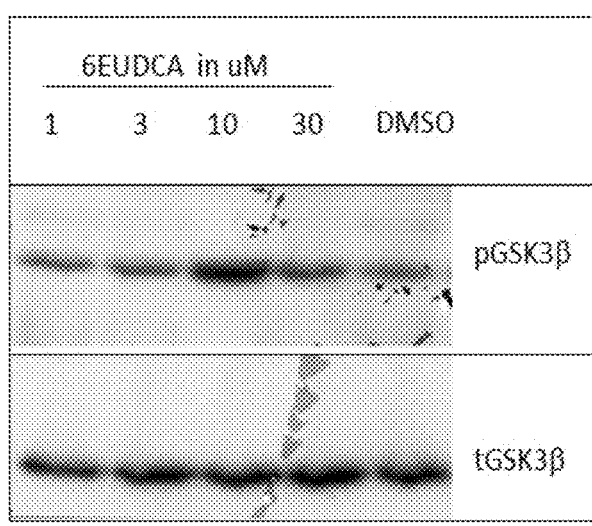
Figure 7A:
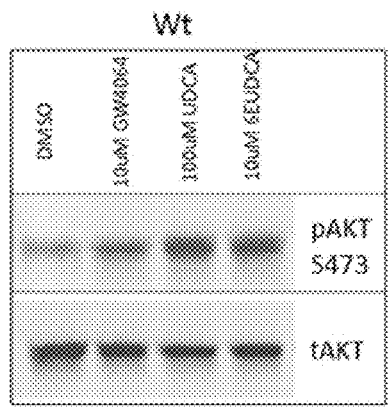
FIGS. 7A-7D show that phosphorylation of AKT and GSK beta is mediated by FXR in liver cells. Extracts were analyzed by Western blot using specific antibodies against pAKT S473 (FIG. 7A and FIG. 7B) or pGSK3beta (FIG. 7C and FIG. 7D).
Figure 7B:
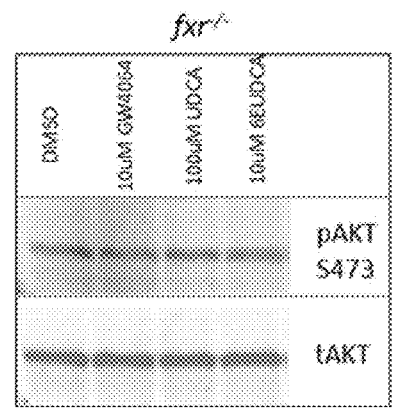
Figure 7C:
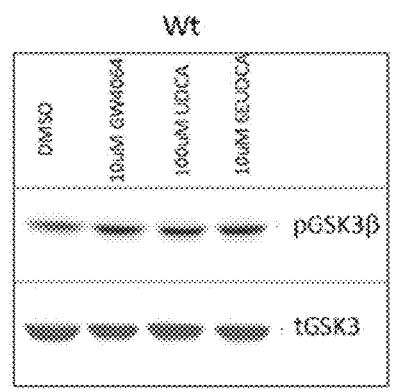
Figure 7D:
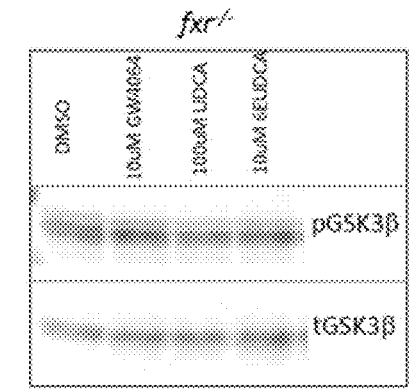

To further investigate the dose dependence of AKT phosphorylation, we treated HepG2 cells with increasing concentrations of 6EUDCA. Serum-starved HepG2 cell extracts were prepared after incubation with different concentrations of 6EUDCA (DMSO/0 M, 1 μM, 3 μM, 10 M or 30 M) for 10 min. Extracts were analyzed by Western blot using specific antibodies against pAKT S473 (left panel) or pGSK3beta (right panel). This data shows that much lower concentrations of 6EUDCA is required to induce AKT phosphorylation as compared to UDCA indicating a higher potency for 6EUDCA. Western blot analysis indicated that changes brought about in phosphorylation levels of AKT by 6EUDCA were dose dependent (FIG. 6).

We next tested if UDCA- and 6EUDCA-dependent phosphorylation of AKT may be mediated by FXR. Serum-starved mouse primary hepatocytes isolated from either wild-type or $fxr^{-/-}$ mice were treated with or without UDCA or 6EUDCA for 10 min. Cell extracts were prepared and immunoblotted for phosphorylated AKT or phosphorylated GSK3beta. Western blot analysis indicated that the UDCA and 6EUDCA induced phosphorylation of AKT in wild-type hepatocytes but not in fxr−/− hepatocytes (FIG. 7). This result strongly suggests that UDCA and 6EUDCA act via FXR in liver cells to induce phosphorylation of AKT. This result also indicates a new non-genomic function for FXR apart from its role as a transcription factor in liver cells.

Figure 8A:
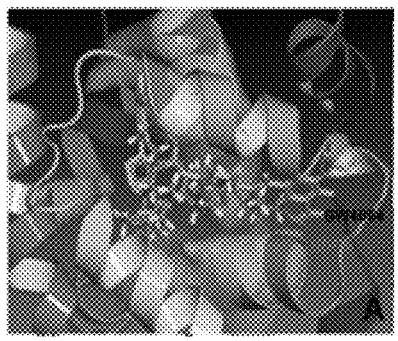
FIGS. 8A-8D show binding modes of 6EUDCA and UDCA to protein FXR.
Figure 8B:
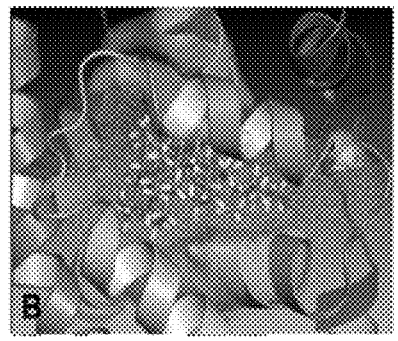

Finally, to explore the binding mode of 6EUDCA and UDCA to FXR, our in-house All-Around-Docking (AAD) methodology (Reference 32) was implemented to predict the best docking site and docking pose. AAD uses Glide software (Schrödinger) and allows a small molecule to search the whole surface of a target protein for the docking site with the lowest docking score. The structure of the FXR protein bound to GW4064 was used as the docking target (PDB ID: 3DCT) (Reference 33). Using this approach, 6EUDCA, UDCA and GW4064 were predicted to share the same FXR binding pocket (FIGS. 8A and 8B), which is formed by M265, M290, R331, H447, W469, etc. 6EUDCA contacts more closely with FXR surface than UDCA. For example, there are 10 residues are within 2 Å of 6EUDCA, which are M265, A291, H294, V325, M328, F329, R331, S332, H447 and W454. In contrast, there are only 3 residues (A291, R331 and S332) are within 2 Å of UDCA.

Figure 8C:
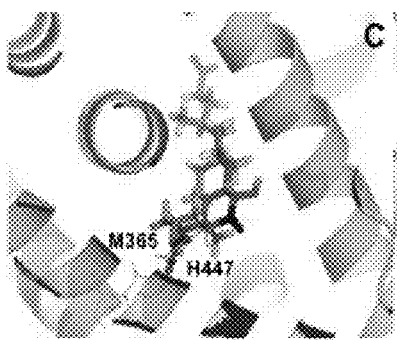
Figure 8D:
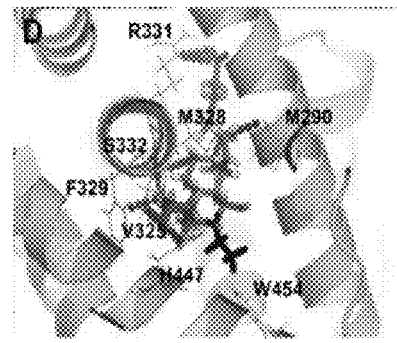

Our computational modes show that 6EUDCA forms a larger network of hydrogen bonds with FXR as compared to UDCA. As depicted in FIG. 8C, two hydrogen bonds are formed between the UDCA molecule and FXR protein. On the other hand, eight hydrogen bonds are formed between 6EUDCA and FXR (FIG. 8D). Furthermore, the 6EUDCA ethyl can form strong hydrophobic interaction with W454 residue as shown in FIG. 8D. The calculated binding energies predict that FXR associates more strongly with GW4064 (estimated −17.19 kcal/mol binding energy) than UDCA (estimated −9.24 kcal/mol) or 6EUDCA (−10.85 kcal/mol). Based on these results, 6EUDCA is predicted to bind more strongly than UDCA.

To investigate the ability of 6EUDCA to modulate biological events via FXR, we used cell-based studies in human HepG2 cell lines and mouse hepatocytes isolated from wild-type or FXR deficient ($fxr^{-/-}$) mice. We found that UDCA and 6EUDCA are selective, non-genomic modulators of the bile acid receptor FXR. Given the proposed role of FXR in the treatment of CGD, we identified 6EUDCA as a more potent and high affinity modulator for FXR than the parent FDA-approved drug UDCA. Computational studies identified a putative binding site for 6EUDCA in FXR and a potential explanation for the increased efficacy of 6EUDCA and its increased binding affinity relative to UDCA.

Several chemically or genetically modified insulin proteins have been developed that tune the pharmacokinetics of insulin activity for insulin therapy. Incorporation of an aliphatic domain to facilitate hydrophobic interactions and increase the duration of action of insulin has been demonstrated.

A strategy for increasing the half-life insulin in order to provide long acting insulin is by chemical conjugation of insulin to the compounds described herein to form derivatives such as INS-6EUDCA (FIG. 9). This could provide glucose control that is superior to native insulin, because 6EUDCA-conjugated heparin could be highly absorbed in the intestine without damaging the tissue structure of the mucous membrane. Moreover, 6EUDCA-conjugated insulin could be a new oral delivery carrier based on bile acid which could improve the oral bioavailability of human insulin and could enhance the absorption of poorly permeable macromolecules in the intestine. Therefore, we hypothesize that covalent coupling of the molecules described herein, e.g., 6EUDCA, to a specific site of insulin may improve the therapeutic profiles of insulin while maintaining its biological activity.

In summary, we have demonstrated that UDCA and its analog 6EUDCA bind to FXR but do not affect the basal transcriptional activity of the protein. 6EUDCA may be non-genomic selective.

REFERENCES (1) Shaffer, E. A. Epidemiology and risk factors for gallstone disease: has the paradigm changed in the 21st century. Curr Gastroenterol Rep 2005, 7, 132-140.
(2) Wang, H. H.; Portincasa, P.; de Bari, O.; Liu, K. J.; Garruti, G.; Neuschwander-Tetri, B. A.; Wang, D. Q. Prevention of cholesterol gallstones by inhibiting hepatic biosynthesis and intestinal absorption of cholesterol. *Eur J Clin Invest.* 2013, 43, 413-26.
(3) Salen, G.; Colalilo, A.; Verga, D.; Bagan, E.; Tint G. S.; Shefer S. Effect of high and low doses of ursodeoxycholic acid on gallstone dissolution in humans *Gastroenterology*, 1980, 78, 1412-1418.
(4) D'Amore, C.; Di Leva, F. S.; Sepe, V.; Renga, B.; Del Gaudio, C.; D'Auria, M. V.; Zampella, A.; Fiorucci, S.; Limongelli, V. Design, synthesis, and biological evaluation of potent dual agonists of nuclear and membrane bile acid receptors. J. Med. Chem. 2014, 57, 937-954.
(5) Moschetta, A.; Bookout A. L.; Mangelsdorf, D. J. Prevention of cholesterol gallstone disease by FXR agonists in a mouse model. *Nat Med* 2004, 10, 1352-1358.
(6) Pellicciari, R.; Fiuorucci, S.; Camaioni, E.; Clerici, C.; Costantino, G.; Maloney, P. R.; Morelli, A.; Parks, D. J.; Willson, T. M. 6α-Ethyl-Chenodeoxycholic Acid (6-ECDCA), a Potent and Selective FXR Agonist Endowed with Anticholestatic Activity. *J. Med. Chem.* 2002, 45, 3569-3572.
(7) Forman, B. M.; Goode, E.; Chen, J.; Oro, A. E.; Bradley, D. J.; Perlmann, T.; Noonan, D. J.; Burka, L. T.; McMorris, T.; Lamph, W. W.; Evans, R. M.; Weinberger, C. Identification of a nuclear receptor that is activated by farnesol metabolites, *Cell* 1995, 81, 687-693.
(8) Wang, H.; Chen, J.; Hollister, K.; Sower, L. C.; Forman, B. M. Endogenous bile acids are ligands for the nuclear receptor FXR/BAR, Mol. *Cell,* 1999, 3, 543-553.
(9) Watanabe, M.; Houten, S. M.; Mataki, C.; Christoffolete, M. A.; Kim, B. W.; Sato, H.; Messaddeq, N.; Harney, J. W.; Ezaki, O. T.; Kodama, T.; Schoonjans, K.; Bianco, A. C.; Auwerx, J. Bile acids induce energy expenditure by promoting intracellular thyroid hormone activation. *Nature* 2006, 439, 484-489.
(10) Heathcote, E. J. Management of primary biliary cirrhosis. The American Association for the Study of Liver Diseases practice guidelines. *Hepatology* 2000, 31, 1005-1013.
(11) Yu, D. D.; Sousa, K. M.; Mattern, D. L.; Vaidehi, N.; Forman, B. M.; Huang, W. et al. Stereoselective Synthesis, Biological Evaluation, and Modeling of Novel Bile Acid-Derived G-Protein Coupled Bile Acid Receptor 1 (GP-BAR1, TGR5) Agonists, *Bioorganic & Medicinal Chemistry* 2015, 23, 1613-1628.
(12) Sharma R, Prichard D, Majer F, Byrne A M, Kelleher D, Long A, Gilmer J F. Ursodeoxycholic acid amides as novel glucocorticoid receptor modulators. *J Med Chem.* 2011, 54, 122-30.
(13) Campana, G.; Pasini, P.; Roda, A.; Spampinato, S. Regulation of ileal bile acid-binding protein expression in Caco-2 cells by ursodeoxycholic acid: Role of the farnesoid X receptor, *Biochemical Pharmacology,* 2005, 61, 1755-1763.
(14) Wittenburg, H.; Lyons, M. A.; Li, R.; Churchill, G. A.; Carey, M. C.; Paigen, B. "FXR and ABCGs/ABCG8 as determinants of cholesterol gallstone formation fromquantitative trait locus mapping in mice," *Gastroenterology,* 2003, 125, 868-881.
(15) U.S. Pat. No. 39,435 A1, 2011.
(16) Liu, Z. Advance in methods for preparation of ursodeoxycholic acid, Yaoxue Tongbao. 1988, 23, 583-86, *Chem Abstr.* 1989, 110, 115167s.
(17) Kanajawa, T. *Proc. Japan Acad* 1954, 30, 391.
(18) Hofmann, A. F. Pharmacology of ursodeoxycholic acid, an enterohepatic drug. *Scand J. Gastroenterol,* 1994, 29, 1-15.
(19) Fieser, L. F.; Rajagopalan, S. Oxidation of steroid. III. Selective oxidation and acylations in bile acid series. *J Am Chem Soc* 1950, 72, 5530-6.
(20) Sammuelson, B. Preparation of ursodeoxycholic acid and 3α,7β,12α-trihydroxycholanic acid. *Acta Chem Scand* 1960, 14, 17-20.
(21) ES 489,661, 1980.
(22) Iida, T.; Chang, F. C. Potential Bile Acid metabolites. 6. Stereoisomeric 3,7-Dihydroxy-50-Cholanic Acids. *J. Org. Chem.* 1982, 47, 2969.
(23) ES 499,525, 1981.
(24) Yu, D.; Mattern, D. L.; Forman, B. M. An Improved Synthesis of 6α-Ethylchenodeoxycholic Acid (6ECDCA), a Potent and Selective Agonist for the Farnesoid X Receptor (FXR), *Steroids* 2012, 77, 1335.
(25) Piatkowski, W.; Mazurkiewicz, W. *Pol. J. Appl. Chem.* The oxidation technology of hydroxycholanic acids to the corresponding oxo-derivatives. 1999, 43, 85-93.
(26) Hsia, S. L.; Matschiner, J. T.; Mahowald, T. A.; Eliott, W. H.; Doisy, E. A.; Thayer, S. A.; Doisy, E. A. Bile acids. V. Chemical studies on new bile acids from the rat and the hog. *J. Biol. Chem.* 1957, 811-823.
(27) (a) Meerwein, H.; Schmidt, R. Halogenated alcohols. *Justus Liebigs Ann. Chem.* 1925, 444, 221. (b) Ponndorf, W. The reversible exchange of oxygen between aldehydes or ketones on the one hand and primary or secondary alcohols on the other hand. *Angew. Chem.* 1926, 39, 138. (c) Verley, M. *Bull. Soc. Chim. Fr.* 1925, 37, 871.
(28) Miyashita, N; Yoshkoshi, A; Grieco, P. A. Pyridinium p-toluenesulfonate. A mild and efficient catalyst for the tetrahydropyranylation of alcohols. *J. Org. Chem.* 1977, 42, 3772-3774.
(29) Bhattacharyya, P. K.; Bankawala, Y. G. Determination of chenodeoxycholic acid and ursodeoxycholic acid by nuclear magnetic resonance spectrometry. *Analytical Chem.,* 1978, 50, 1462-1465.
(30) Yu, D. D.; Lin, W.; Chen, T.; Forman, B. M. Development of Time Resolved Fluorescence Resonance Energy Transfer-based Assay for FXR Antagonist Discovery, *Bioorganic & Medicinal Chemistry,* 2013, 21, 4266-4278.
(31) Maloney, P. R.; Parks, D. J.; Haffner, C. D.; Fivush, A. M.; Chandra, G.; Plunket, K. D.; Creech, K. L.; Moore, L. B.; Wilson, J. G.; Lewis, M. C.; Jones, S. A.; Willson, T. M. Identification of a chemical tool for the orphan nuclear receptor FXR. *J. Med. Chem.* 2000, 43, 2971-2974.

(32) Nam, S.; Wen, W.; Schroeder, A.; Herrmann, A.; Yu, H.; Cheng, X.; Merz, K. H.; Eisenbrand, G.; Li, H.; Yuan, Y. C.; Jove, R. Dual inhibition of Janus and Src family kinases by novel indirubin derivative blocks constitutively-activated Stat3 signaling associated with apoptosis of human pancreatic cancer cells. *Mol Oncol.* 2013, 7, 369-78.

(33) Akwabi-Ameyaw, A.; Bass, J. Y.; Caldwell, R. D.; Caravella, J. A.; Chen, L.; Creech, K. L.; Deaton, D. N.; Jones, S. A.; Kaldor, I.; Liu, Y.; Madauss, K. P.; Marr, H. B.; McFadyen, R. B.; Miller, A. B.; III, F. N.; Parks, D. J.; Spearing, P. K.; Todd, D.; Williams, S. P.; Wisely, G. B. Conformationally constrained farnesoid X receptor (FXR) agonists: Naphthoic acid-based analogs of GW 4064. *Bioorg. Med. Chem. Lett.* 2008, 18, 4339-4343.

(34) Bissell, D. M; Guzelian, P. S. Phenotypic stability of adult rat hepatocytes in primary monolayer culture. *Ann N Y Acad Sci.* 1980, 349, 85-98.

(35) Li, T; Kong, X; Owsley, E; Ellis, E; Storm, S; Chiang, J. Y. Insulin regulation of cholesterol 7alpha-hydroxylase expression in human hepatocytes: roles of forkhead box O1 and sterol regulatory element-binding protein 1c. *J. Biol. Chem.* 2006, 281, 28745-18754.

(36) Andrali, S. S; Marz, P; Ozcan, S. Ataxin-10 interacts with O-GlcNAc transferase OGT in pancreatic beta cells. *Biochem Biophys Res Commun.* 2005, 337, 149-153.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of synthesizing a compound having the following structure,

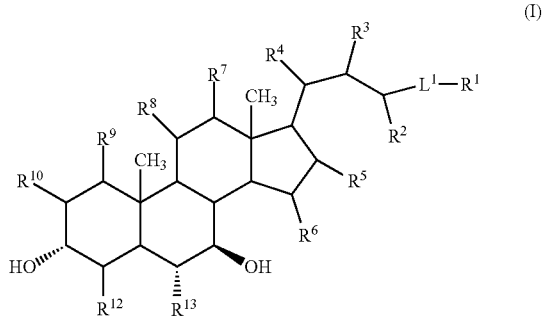

(I)

the method comprising,
(i) contacting a compound of formula (II)

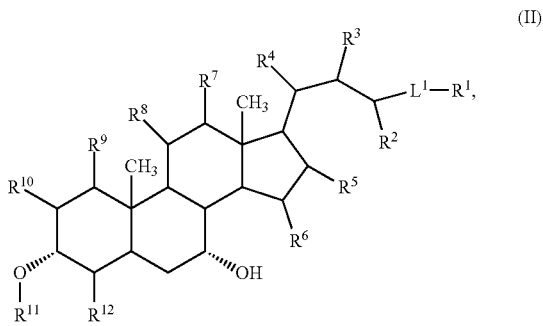

(II)

---

SEQUENCE LISTING

<160> NUMBER OF SEQ ID NOS: 1

<210> SEQ ID NO 1
<211> LENGTH: 110
<212> TYPE: PRT
<213> ORGANISM: Homo sapiens

<400> SEQUENCE: 1

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110 wherein R$^{11}$ is R$^{11A}$ or R$^{11B}$, with an oxidizing reagent to provide a compound of formula (III-A) or (III-B), (III-A)

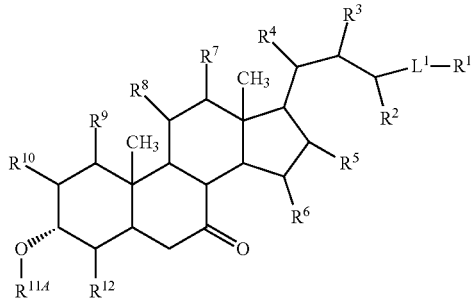

or (III-B)

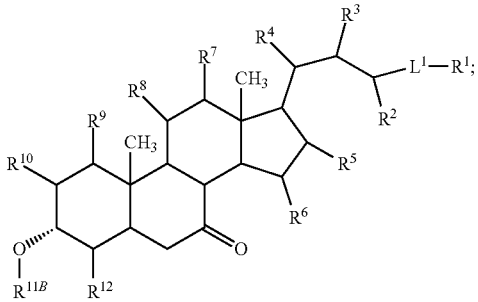

(ii) when the product of step (i) has a structure according to formula (III-A), contacting the compound of formula (III-A) with an alcohol protecting agent to provide a compound of formula (III-B);

(iii) contacting a compound of formula (III-B) with an alkylating agent in the presence of a sterically hindered base to provide a compound of formula (IV), (IV)

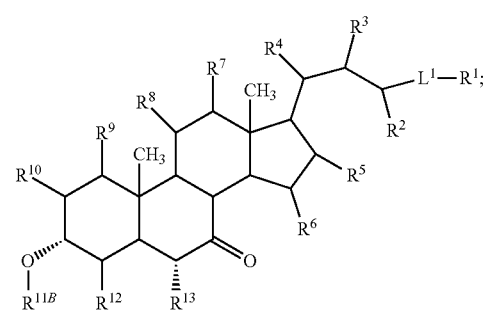

(iv) optionally contacting the compound of formula (IV) with an alcohol deprotecting agent to provide a compound of formula (IV-A), (IV-A)

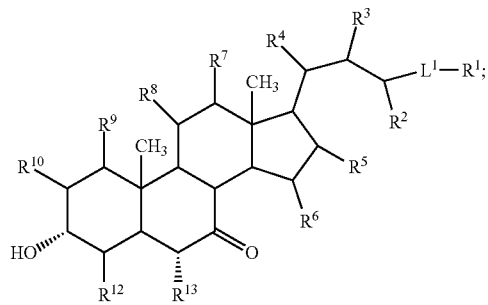

(v) treatment of the compound of formula (IV) or (IV-A) with a reducing agent to provide a compound of formula (I) or (I-A), (I)

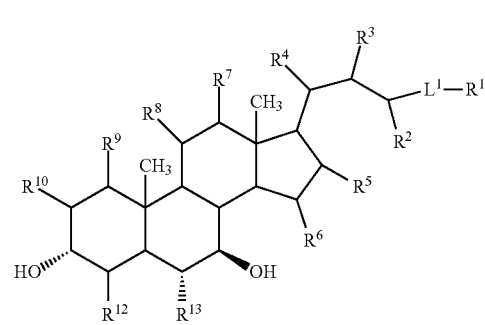

or (I-A)

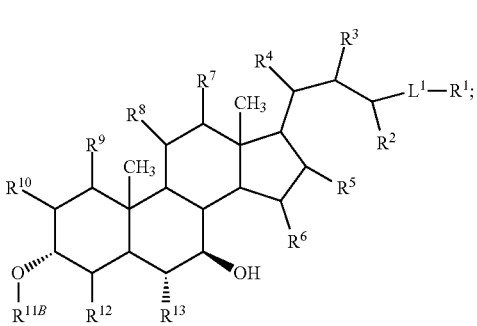

and (vi) when the product of step (v) has a structure according to formula (I-A), contacting the compound of formula with an alcohol deprotecting agent to provide a compound of formula (I-A);

wherein,

L$^1$ is —C(O)—, —C(O)O—, —C(O)NH—, or —CH$_2$—;

R$^1$ is hydrogen, halogen, —N$_3$, —CF$_3$, —CCl$_3$, —CBr$_3$, —CI$_3$, —CN, —CHO, —OR$^{1A}$, —NHR$^{1A}$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or a carboxylate protecting group;

$R^2$ is hydrogen or unsubstituted alkyl;
$R^3$ is hydrogen, unsubstituted alkyl, or —$OR^{3A}$;
$R^4$ is hydrogen, unsubstituted alkyl, or —$OR^{4A}$;
$R^5$ is hydrogen, unsubstituted alkyl, or —$OR^{5A}$;
$R^6$ is hydrogen, unsubstituted alkyl, or —$OR^{6A}$;
$R^7$ is hydrogen, unsubstituted alkyl, or —$OR^{7A}$;
$R^8$ is hydrogen, unsubstituted alkyl, or —$OR^{8A}$;
$R^9$ is hydrogen, unsubstituted alkyl, or —$OR^{9A}$;
$R^{10}$ is hydrogen, unsubstituted alkyl, or —$OR^{10A}$;
$R^{11A}$ is hydrogen;
$R^{11B}$ is an alcohol protecting group;
$R^{12}$ is hydrogen, unsubstituted alkyl, or —$OR^{12A}$;
$R^{13}$ is unsubstituted alkyl;
$R^{1A}, R^{3A}, R^{4A}, R^{5A}, R^{6A}, R^{7A}, R^{8A}, R^{9A}, R^{10A}, R^{12A}$ and $R^{13A}$ are independently hydrogen, unsubstituted alkyl, or an alcohol protecting group.

2. The method of claim 1, the method comprising, (i) contacting a compound of formula (II)

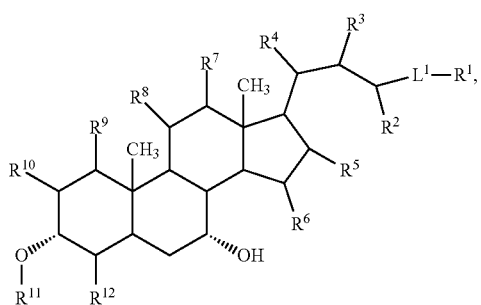

(II)

wherein $R^{11}$ is $R^{11A}$, with an oxidizing reagent to provide a compound of formula (III-A),

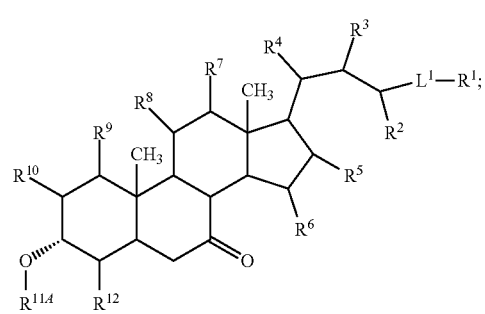

(III-A)

(ii) contacting the compound of formula (III-A) with an alcohol protecting agent to provide a compound of formula (III-B),

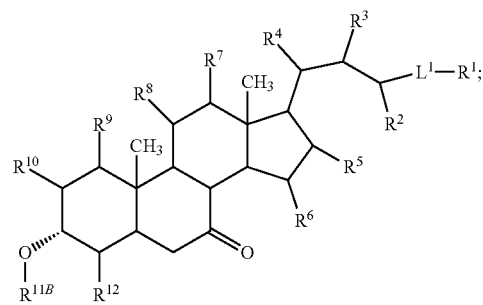

(III-B)

(iii) contacting a compound of formula (III-B) with an alkylating agent in the presence of a sterically hindered base to provide a compound of formula (IV),

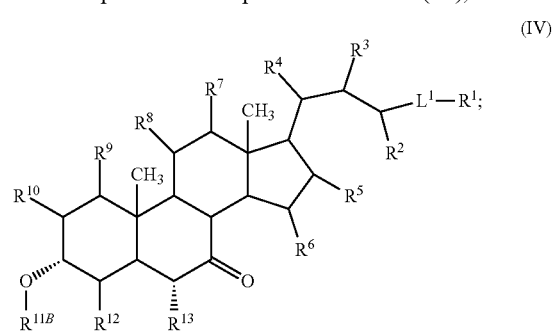

(IV)

(iv) contacting the compound of formula (IV) with an alcohol deprotecting agent to provide a compound of formula (IV-A),

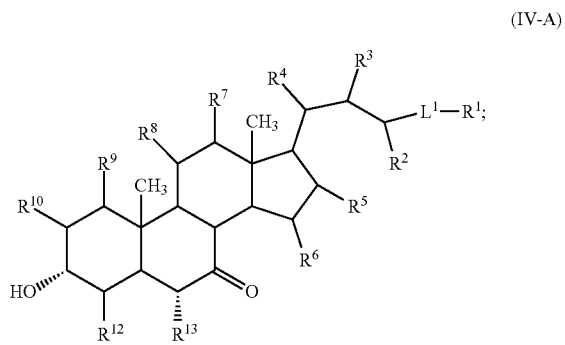

(IV-A)

(v) treatment of the compound of formula (IV-A) with a reducing agent to provide a compound of formula (I),

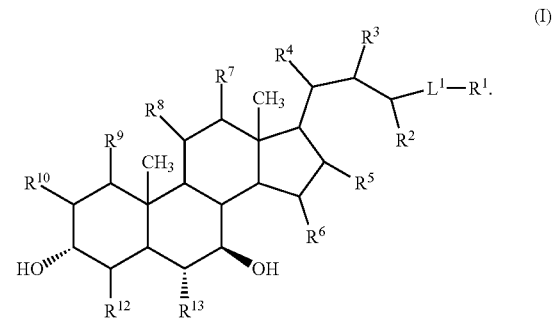

(I)

3. The method of claim 1, the method comprising,
(i) contacting a compound of formula (II)

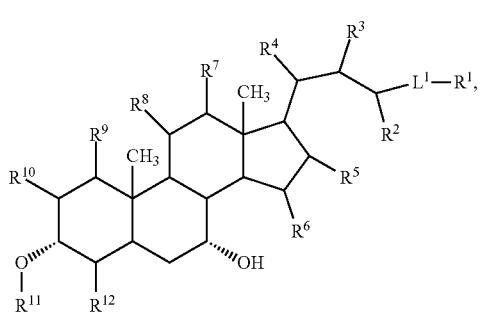
(II)

wherein $R^{11}$ is $R^{11B}$, with an oxidizing reagent to provide a compound of formula (III-B),

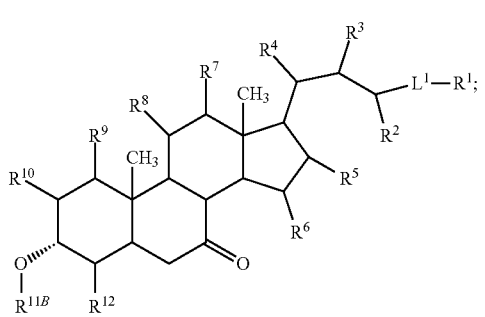
(III-B)

(ii) contacting a compound of formula (III-B) with an alkylating agent in the presence of a sterically hindered base to provide a compound of formula (IV),

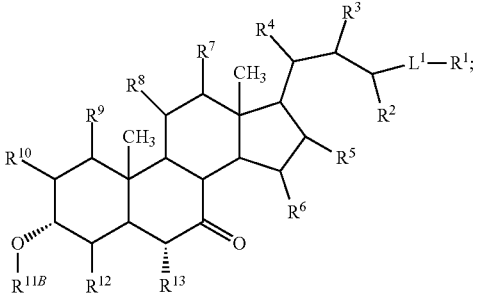
(IV)

(iii) contacting the compound of formula (IV) with an alcohol deprotecting agent to provide a compound of formula (IV-A),

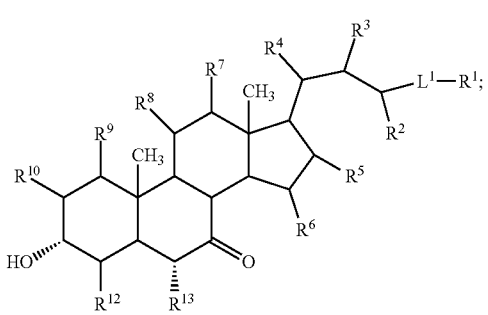
(IV-A)

(iv) treatment of the compound of formula (IV-A) with a reducing agent to provide a compound of formula (I)

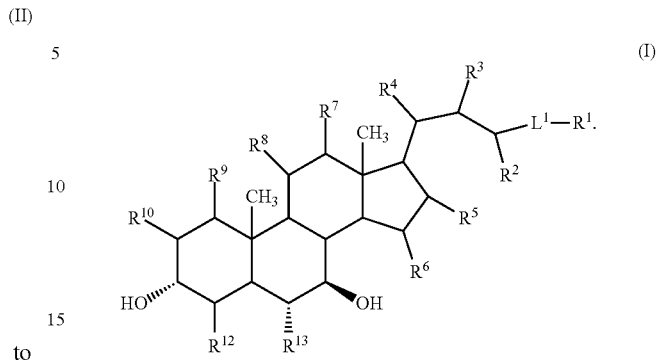
(I)

4. The method of claim 1, wherein $R^{11B}$ is substituted or unsubstituted alkyl, substituted or unsubstituted heteroalkyl, substituted or unsubstituted heterocycloalkyl, or —SiR$^{11C}$R$^{11D}$R$^{11E}$, wherein R$^{11C}$, R$^{11D}$, and R$^{11E}$ are independently substituted or unsubstituted alkyl or substituted or unsubstituted aryl.

5. The method of claim 4, wherein $R^{11B}$ is tetrahydropyranyl (THP).

6. The method of claim 1, wherein the compound of formula (I) has the following structure,

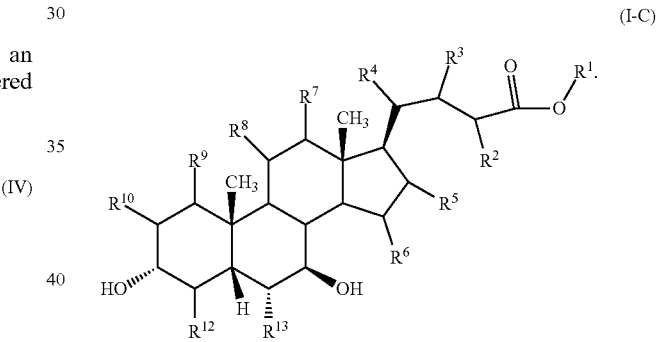
(I-C)

7. The method of claim 1, wherein the compound of formula (I) has the following structure,

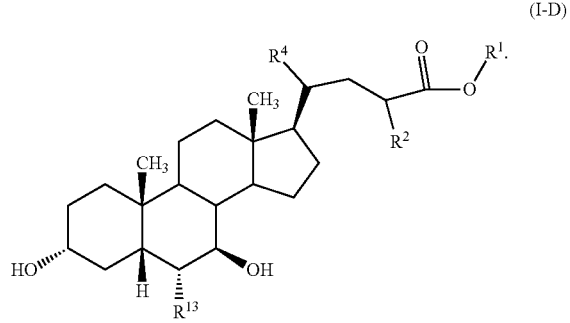
(I-D)

8. The method of claim 7, wherein
$R^1$ is hydrogen;
$R^2$ is hydrogen or unsubstituted alkyl; and
$R^4$ is hydrogen or unsubstituted alkyl.

9. The method of claim 1, wherein the compound of formula (I) has the following structure,

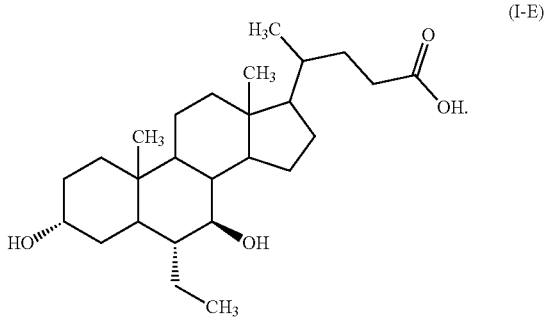 [SMILES: CC[C@@H]1C2C[C@H](O)CCC2(C)C2CCC3(C)C(C(C)CCC(=O)O)CCC3C2[C@H]1O]
(I-E)

10. The method of claim 9, wherein the compound of formula (I) is 6-α-ethyl-ursodeoxycholic acid (6-EUDCA) having the following structure,

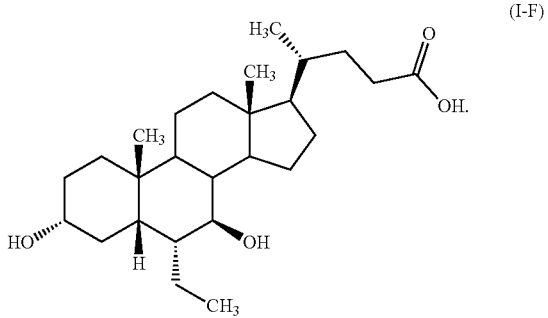 [SMILES: CC[C@H]1[C@H](O)C2C3CC[C@H]([C@H](C)CCC(=O)O)[C@@]3(C)CCC2[C@@]2(C)CC[C@@H](O)C[C@@H]12]
(I-F)

11. The method of claim 1, wherein the oxidizing reagent of step (a) is a chromium oxidant, a ruthenium oxidant, a manganese oxidant, an activated dimethylsulfoxide oxidant, or a hypervalent iodine oxidant.

12. The method of claim 11, wherein the oxidizing reagent is pyridinium chlorochromate (PCC).

13. The method of claim 1, wherein the alcohol oxidation proceeds with greater than about 5:1, 6:1, 7:1, 8:1, 9:1, or 10:1 regioselectivity.

14. The method of claim 1, wherein said sterically hindered base of step (iii) is lithium diisopropylamide (LDA), $(M^{+1})$HMDS, $(M^{+1})$tBuO, $(M^{+1})$TMP, $(M^{+1})$PhO, $(M^{+1})$MeO, $(M^{+1})$EtO, DBU, Dabco, N,N-dichlorohexylmethylamine, N,N-diisopropyl-2-ethylbutylamine, 2,6-di-tert-butyl-4-methylpyridine, pentamethylpiperidine, MTBD, PMDBD, TBD, or tri-tert-butylpyridine, wherein $(M^{+1})$ is Na, K, or Li.

15. The method of claim 14, wherein said sterically hindered base is lithium diisopropylamide (LDA).

16. The method of claim 1, wherein step (iii) comprises a second base.

17. The method of claim 16, wherein said base is an alkyllithium reagent.

18. The method of claim 1, wherein said alkylation agent of step (iii) is an alkyl halide.

19. The method of claim 18, wherein said alkylation agent is an alkyl iodide.

20. The method of claim 1, wherein step (iii) is performed in the presence of a polar aprotic solvent.

21. The method of claim 20, wherein said polar aprotic solvent is HMPA, HMPT, DMF, DMSO, MeCN, dioxane, methylpyrrolidone, DMPU, or a tetra-alkyl urea.

22. The method of claim 1, wherein the reducing agent of step (v) comprises an aluminum alkoxide and an alcohol.

23. The method of claim 22, wherein the reducing agent comprises aluminum isopropoxide and isopropyl alcohol.

24. The method of claim 1, wherein step (v) proceeds with greater than about 5:1, 6:1, 7:1, 8:1, 9:1, 10:1, 15:1, or 20:1 stereoselectivity.

* * * * *